(12) United States Patent
Fazekas De St Groth et al.

(10) Patent No.: US 9,291,623 B2
(45) Date of Patent: Mar. 22, 2016

(54) KIT FOR IDENTIFYING REGULATORY T CELLS

(75) Inventors: Barbara Denise Fazekas De St Groth, Glebe (AU); Anthony Dominic Kelleher, Bangor (AU); Alan Lee Landay, River Forest, IL (US); Sarah Christina Sasson, Bondi (AU); Nabila Seddiki, Newtown (AU); John James Zaunders, Kingsford (AU)

(73) Assignee: CENTENARY INSTITUTE OF CANCER MEDICINE AND CELL BIOLOGY, New South Wales (AU)

(*) Notice: Subject to any disclaimer, the term of this patent is extended or adjusted under 35 U.S.C. 154(b) by 106 days.

(21) Appl. No.: 13/087,910

(22) Filed: Apr. 15, 2011

(65) Prior Publication Data

US 2011/0318749 A1    Dec. 29, 2011

Related U.S. Application Data

(62) Division of application No. 11/989,933, filed as application No. PCT/AU2006/001080 on Jul. 31, 2006, now Pat. No. 7,947,464.

(30) Foreign Application Priority Data

Aug. 2, 2005  (AU) ................................ 2005904145

(51) Int. Cl.
```
C07K 16/28     (2006.01)
G01N 33/569    (2006.01)
C12N 5/0783    (2010.01)
```

(52) U.S. Cl.
CPC ........ *G01N 33/56966* (2013.01); *C12N 5/0636* (2013.01); *G01N 2333/70514* (2013.01); *G01N 2333/70596* (2013.01); *G01N 2800/52* (2013.01)

(58) Field of Classification Search
None
See application file for complete search history.

(56) References Cited

U.S. PATENT DOCUMENTS

| 4,281,061 | A | * | 7/1981 | Zuk et al. ........................ 435/7.9 |
| 5,859,205 | A | * | 1/1999 | Adair et al. .................... 530/387.3 |
| 5,977,322 | A | * | 11/1999 | Marks et al. .............. 530/388.85 |
| 2002/0099179 | A1 | * | 7/2002 | Jolliffe et al. .............. 530/387.3 |
| 2004/0146508 | A1 | * | 7/2004 | Hearing et al. ............. 424/144.1 |
| 2006/0099582 | A1 | * | 5/2006 | Papadopoulos et al. .......... 435/6 |

FOREIGN PATENT DOCUMENTS

WO    WO 02102853 A2  * 12/2002
WO    WO 2004083247 A1 * 9/2004

OTHER PUBLICATIONS

Managlia et al., Immunology. Mar. 2005;114(3):322-35.*
Goldsby et al., Immunology, W.H. Freeman and Company, 5th ed., 2002, pp. 282-284 and Appendix p. A-9.*
Napolitano et al., J Immunol 2003; 171:645-654.*
Specification sheet for the anti-human IL-7Rα antibody conjugated to PE commercially available from Beckman Coulter, IM1980U, p. 1 of 1, downloaded from https://www.beckmancoulter.com/wsrportal/page/itemDetails?itemNumber=IM1980U#2/10//0/25/1/0/asc/2/IM1980U//C_TECHNICALDOCS/0/0//1/ on Oct. 17, 2012.*
Santa Cruz Biotechnologies, Research Antibodies, 1998, IL-7R (C-20), p. 439.*
Onrust et al., Drugs Feb. 1999; 57 (2): 207-213.*
Chen et al., Experimental Hematology 31 (2003) 1019-1025.*
Watanabe et al., J. Exp. Med., vol. 187, No. 3, Feb. 2, 1998, 389-402.*
Okada et al., Am J Physiol Gastrointest Liver Physiol 288:G745-G754, 2005. First published Nov. 18, 2004.*
Strom et al., Therapeutic Immunology edited by Austen et al., Blackwell Science, Cambridge, MA, 1996; pp. 451-456.*
*AstraZeneca LP v. Apotex Inc.*, 97 USPQ2d 1029 (Fed. Cir. 2010), pp. 1-47.*
In re Ngai, 70 USPQ2d 1862 (Fed. Cir. 2004), pp. 1-7.*
In re Kao, 98 USPQ2d 1799 (Fed. Cir. 2011), pp. 1-29.*
Franchimont et al. (The Journal of Immunology, 2002, 168: 2212-2218).*
Janeway et al. (Immunobiology, 5th edition, Garland Publishing, 2001, pp. 636-637).*
Goldsby et al. (Immunology, 5th Ed., W.H. Freeman and Co., pp. 334-335).*
Klein et al. (Immunology, 2nd Ed., Blackwell Science, 1997, pp. 642-644).*
Popescu et al. (American Journal of Transplantation 2003; 3: 1369-1377).*
Fry et al. (J Immunol 2005; 174:6571-6576).*
Fry et al. (Blood. 2003; 101:2294-2299).*
Setoguchi et al., JEM, vol. 201, No. 5, Mar. 7, 2005 723-735.*
Fuller et al., The Journal of Immunology, 2005, 174: 5926-5930.*
Paiardini, M., et al., "Loss of CD127 Expression Defines an Expansion of Effector CD8$^{30}$ T Cells in HIV-Infected Individuals," The Journal Of Immunology, 2005, pp. 2900-2909, 0022-1767/05, The American Association of Immunologists, Inc.
Caton, A. J., et al., "CD4$^+$ CD25$^+$ Regulatory T Cell Selection," Annals New York Academy of Sciences, 2004, pp. 101-114, vol. 1029, New York Academy of Sciences.
Seddiki, N., et al., "Expression of interleukin (IL)-2 and IL-7 receptors discriminates between human regulatory and activated T cells," JEM, Jul. 10, 2006, pp. 1693-1700, vol. 203, No. 7, The Rockefeller University Press, www.jem.org/cgi/doi/10.1084/jem.20060468.
L.S. Ou et al., "T regulatory cells in atopic dermatitis and subversion of their activity by superantigens," J Allergy Clin Immunol, vol. 113, No. 4, Apr. 2004.
C Karagiannidis et al., "Glucocorticoids upregulate FOXP3 expression and regulatory T cells in asthma," J Allergy Clin Immunol, vol. 114, No. 6, Dec. 2004.
K. Wood et al., "Regulatory T Cells in Transplantation Tolerance," Nature Reviews, Immunology; vol. 3, Mar. 2003.
T. Cupedo et al., "Development and activation of regulatory T cells in the human fetus," Eur. J. Immunol. 2005. 35: 383-390.

(Continued)

*Primary Examiner* — Zachary Skelding
(74) *Attorney, Agent, or Firm* — McDermott Will & Emery LLP

(57) ABSTRACT

The present invention relates to methods and kits for identifying, quantifying and isolating regulatory T cells, to methods and kits for diagnosing or monitoring autoimmune diseases, immunoinflammatory diseases, allergic diseases, predispositions thereto, infectious diseases, cancer, cancer treatment and/or organ transplantation based on regulatory T cell quantity, to methods and kits for predicting responses to therapy for autoimmune diseases, immunoinflammatory diseases, allergic diseases, predispositions thereto, infectious diseases, cancer and/or organ transplantation based on regulatory T cell quantity, and to methods and kits for therapy using isolated regulatory T cells.

9 Claims, 36 Drawing Sheets

(56) References Cited

OTHER PUBLICATIONS

N.E. Aerts et al., "Activated T cells complicate the identification of regulatory T cells in rheumatoid arthritis," Cellular Immunology 251 (2008) 109-115.
W. Liu et al., "CD127 expression inversely correlates with Fox P3 and suppressive function of human CD4+ T reg calls," The Journal of Experimental Medicine, vol. 203, No. 7, Jul. 10, 2006, 1701-1711.
A.. Kukreja et al.,"Multiple immuno-regulatory defects in type-1 diabetes," The Journal of Clinical Investigation, Jan. 2002, vol. 109, No. 1.
D. Cao et al., "Isolation and functional characteristics of regulatory $CD25^{bright}CD4^+$ T cells from the target organ of patients with rheumatoid arthritis," Eur. J. Immunol. 2003. 33:215-223.
J.C. Crispin et al., "Quantification of regulatory T cells in patients with systemic lupus erythematosus," Journal of Autoimmunity 21 (2003) 273-276.
J. Maul et al., "Peripheral and Intestinal Regulatory $CD4+CD25^{high}$ T Cells in Inflammatory Bowel Disease," Gastroenterology 2005; 128; 1868-1878.
L.A. Ormandy et al., "Increased Populations of Regulatory T Cells in Peripheral Blood of Patients with Hepatocellular Carcinoma," Cencer Res 2005; 65: (6). Mar. 15, 2005.
Cozzo, C., et al., "Cutting Edge: Self-Peptides Drive the Peripheral Expansion of CD4+ CD25+ Regulatory T Cells", Track Proliferation in GFP+ Cells! Cell Proliferation Dye eFluor® 670, The Journal of Immunology, 2003, pp. 5678-5682, 171, The American Association of Immunologists, Inc.
Alpdogan, O., et al., "IL-7 Administration Enhances Peripheral T Cell Reconstitution after Allogenic Hematopoietic Stem Cell Transplantation (HSCT) through Increased Homeostatic Profileration and Anti-Apoptotic Effects", Experimental Transplantation I: Immune Reconstitution, Stem Cells and Mobilization, p. 107a.
Seddiki, N., et al., "A New Gating Strategy to Identify Human Regulatory T Cells", Tissue Antigens, Nov. 2005, p. 537, vol. 66 No. 5, Blackwell Munksgaard.
Baecher-Allan, et al., Semin Immunol. Apr. 2004; 16(2) 89-98.
Sereti, I. et al. "In Vivo Expansion of CD4+CD445RO–CD25+ T Cells Expressing FoxP3 in IL-2-treated HIV-Infected Patients". Journal of Clinical Investigation. Jul. 2005. vol. 115. No. 7. pp. 1839-1847.
European Search Report issued in European Patent Application No. 06760937.0 dated Jul. 12, 2012.
C.J. Campbell and P. Ghazal, "Molecular Signatures for Diagnosis of Infection: Application of Microarray Technology," J. of Applied Microbiology 2004, 96:18-23.
Y. Soen et al., "Detection and Characterization of Cellular Immune Responses Using Peptide-MHC Microarrays," PLoS Biology 2003, 1(3):429-438.
G. Hudelist et al., "Use of High-Throughput Arrays for Profiling Differentially Expressed Proteins in Normal and Malignant Tissues," Anti-Cancer Drugs: Review Papers 2005, 16(7):683-689.
J. Avouac et al., "Diagnostic and Predictive Value of Anti-Cyclic Citrullinated Protein Antibodies in Rheumatoid Arthritis: A Systematic Literature Review," Ann Rheum Dis 2006, 65:845-851.
K. Wood and S. Sakaguchi, "Regulatory Cells in Transplantation Tolerance," Nature Reviews Immunology Mar. 2003, 3:199-210.
C. Piccirillo and E. Shevach, "Naturally-Occurring CD4+CD25+ Immunoregulatory T Cells: Central Players in the Arena of Peripheral Tolerance," Seminars in Immunology 2004, 16:81-88.
W. Chen et al., "Conversion of Peripheral CD4+CD25– Naive T Cells to CD4+CD25+ Regulatory T Cells by TGF-β Induction of Transcription Factor Foxp3," J. of Experimental Medicine, 198(12):1875-1886 (Dec. 15, 2003).
J. Huehn et al., "Migration Rules: Functional Properties of Naive and Effector/Memory-Like Regulatory T Cell Subsets," CTMI 2005, 293: 89-114.
N. Seddiki et al., "Expression of Interleukin (IL)-2 and IL-7 Receptors Discriminates Between Human Regulatory and Activated T Cells," J. of Exp Med, 203(7):1693-1700 (Jul. 10, 2006).

* cited by examiner

Figure 29
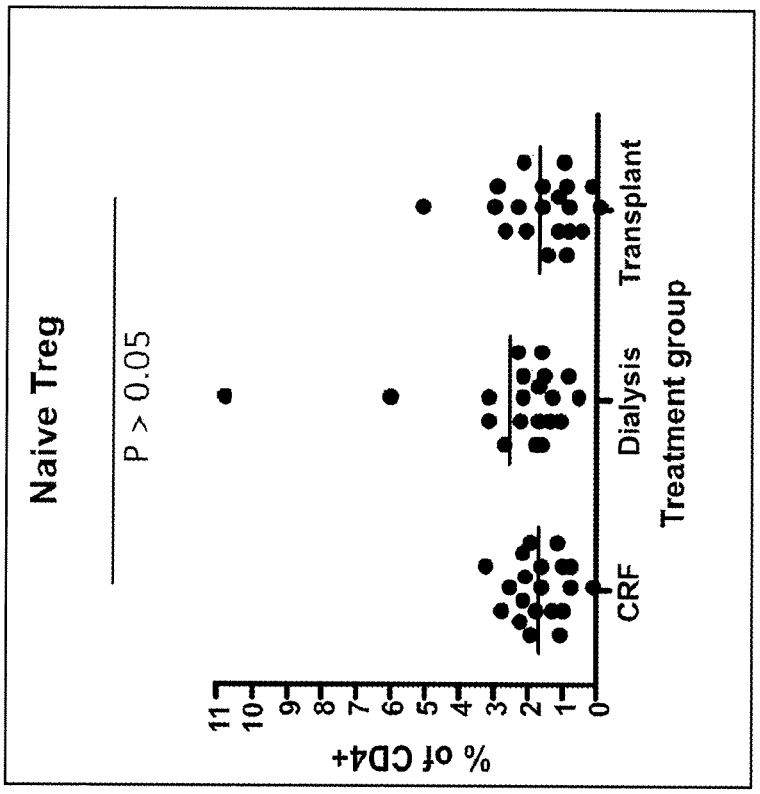
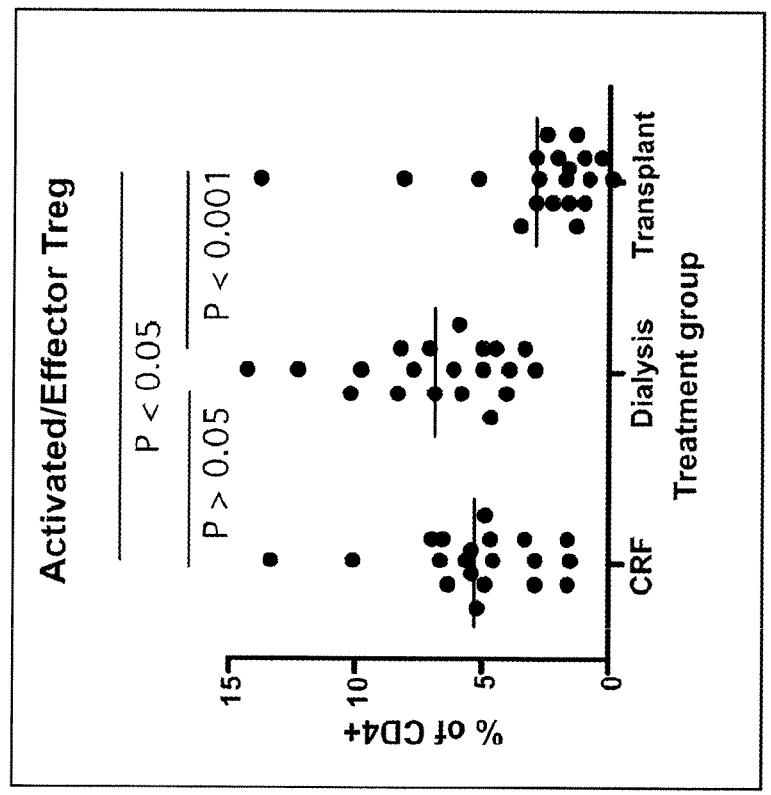

SEQUENCE LISTING

```
<160> NUMBER OF SEQ ID NOS: 8

<210> SEQ ID NO 1
<211> LENGTH: 21
<212> TYPE: DNA
<213> ORGANISM: Artificial
<220> FEATURE:
<223> OTHER INFORMATION: Synthetic sequence

<400> SEQUENCE: 1
ggcaaatggt gtctgcaagt g                                                   21

<210> SEQ ID NO 2
<211> LENGTH: 21
<212> TYPE: DNA
<213> ORGANISM: Artificial
<220> FEATURE:
<223> OTHER INFORMATION: Synthetic sequence

<400> SEQUENCE: 2
ggatgatgcc acagatgaag c                                                   21

<210> SEQ ID NO 3
<211> LENGTH: 25
<212> TYPE: DNA
<213> ORGANISM: Artificial
<220> FEATURE:
<223> OTHER INFORMATION: Synthetic Sequence

<400> SEQUENCE: 3
aactgtcaga ccaccacaac cacac                                               25

<210> SEQ ID NO 4
<211> LENGTH: 26
<212> TYPE: DNA
<213> ORGANISM: Artificial
<220> FEATURE:
<223> OTHER INFORMATION: Synthetic sequence

<400> SEQUENCE: 4
ggatgccttc cttcttcata gtcagg                                              26

<210> SEQ ID NO 5
<211> LENGTH: 24
<212> TYPE: DNA
<213> ORGANISM: Artificial
<220> FEATURE:
<223> OTHER INFORMATION: Synthetic sequence

<400> SEQUENCE: 5
cactacagga tgtttgtgga cgtg                                                24

<210> SEQ ID NO 6
<211> LENGTH: 24
<212> TYPE: DNA
<213> ORGANISM: Artificial
<220> FEATURE:
```

```
<223> OTHER INFORMATION: Synthetic sequence

<400> SEQUENCE: 6
ccccttgttg tttgtgagct ttag                                              24

<210> SEQ ID NO 7
<211> LENGTH: 26
<212> TYPE: DNA
<213> ORGANISM: Artificial
<220> FEATURE:
<223> OTHER INFORMATION: Synthetic sequence

<400> SEQUENCE: 7
tcgacaacgg ctccggcatg tgcaag                                            26

<210> SEQ ID NO 8
<211> LENGTH: 25
<212> TYPE: DNA
<213> ORGANISM: Artificial
<220> FEATURE:
<223> OTHER INFORMATION: Synthetic sequence

<400> SEQUENCE: 8
agccacacgc agctcattgt agaag                                             25
```

KIT FOR IDENTIFYING REGULATORY T CELLS

RELATED APPLICATIONS

This application is a Divisional of U.S. patent application Ser. No. 11/989,933, filed on Sep. 12, 2008, now U.S. Pat. No. 7,947,464 which is a U.S. National Phase under 35 U.S.C. §371 of International Application No. PCT/AU2006/001080, filed on Jul. 31, 2006, which in turn claims the benefit of Australian Application No. 2005904145, filed on Aug. 2, 2005, the disclosures of which Applications are incorporated by reference herein.

TECHNICAL FIELD

The present invention relates to methods and kits for identifying, quantifying and isolating regulatory T cells, to methods and kits for diagnosing or monitoring autoimmune diseases, immunoinflammatory diseases, allergic diseases, predispositions thereto, infectious diseases, cancer, cancer treatment and/or organ transplantation, based on regulatory T cell quantity, to methods and kits for predicting responses to therapy for autoimmune diseases, immunoinflammatory diseases, allergic diseases, predispositions thereto, infectious diseases, cancer and/or organ transplantation based on regulatory T cell quantity, and to methods and kits for therapy using isolated regulatory T cells.

BACKGROUND OF THE INVENTION

The identification of specific types of cells present in a biological sample comprises a fundamentally important aspect of scientific, diagnostic and medical endeavour. The means by which such identification can be achieved often involves ascertaining the type of molecules expressed on the surface of cells. Such cell surface expression patterns can be determined using standard methods known to those skilled in the art, typically involving exposure of cells to antibodies that are specific for certain cell surface molecules. Antibodies used for this purpose can be conjugated either directly or indirectly with a fluorochrome that emits a signal upon excitation with light of a certain wavelength. In this way, the presence and quantification of particular cell populations in a biological sample can be determined.

Such techniques have found particular application in the field of immunology, where different populations of immune cells can be identified in a biological sample based upon their pattern of cell surface expression. For example, it is known that many lymphocytes express CD45 on their surface, and that a particular population of lymphocytes known as T cells can also express various other cell surface molecules including CD4 and CD25 depending upon their level of activation and development.

$CD4^+$ T cells comprise a heterogeneous population of T cells which are of fundamental importance in both the generation of immune responses and the suppression of autoimmune diseases. A distinct subpopulation of $CD4^+$ T cells also express CD25 and the transcription factor Foxp3. This subpopulation, loosely defined as regulatory T cells (Treg), plays a pivotal role in maintaining self tolerance (1). While the best evidence for the importance of Treg comes from mouse models, an increasing number of reports have outlined disturbances in Treg number and/or function in human patients with a wide variety of autoimmune (2-8), immunoinflammatory (9) and allergic diseases (10, 11), in addition to the very severe IPEX (immune dysregulation, polyendocrinopathy, enteropathy, and X-linked inheritance) syndrome in which the master regulator Foxp3 transcription factor itself is defective (12). Disturbances of Treg numbers have also been reported in cancers such as hepatocellular carcinoma (13) and head and neck cancer (14).

Hence, there is a dear need for a means of accurately identifying and quantifying Treg populations within in a biological sample. However, it has proven difficult to accurately distinguish Treg from $CD25^+$ activated and memory T cells, particularly in human peripheral blood in which up to 20% of antigen-experienced $CD4^+$ T cells also express CD25 (15). Such confusion in determining the precise identity of T cell populations has resulted in several studies reporting ambiguous results. For example, some studies have demonstrated an apparent reduction in Treg numbers in autoimmune conditions (2, 3, 8, 16), while others have shown normal or even increased numbers of $CD4^+CD25^+$ T cells (17-20).

The inventors have shown that a subpopulation of adult human naive $CD4^+CD25^+$ Treg cells derived from the thymus can be distinguished from the large population of $CD25^+$ antigen-experienced conventional T cells on the basis of expression of $CD45RA^+/RO^-$ (21). This naïve Treg population is reduced in young patients with inflammatory bowel disease (IBD), consistent with the existence of a primary deficiency in Treg production in these patients (22). However testing by the inventors with 38 different monoclonal antibodies failed to provide any means of separating human $CD45RA^-RO^+$ Treg from activated/memory $CD45RA^-/RO^+$ T cells (21). Many of these monoclonal antibodies had previously been claimed to provide an accurate means of identification of $CD45RA^-/RO^+$ Treg (15, 23). It is therefore apparent that there is a need for improved methods of identifying Treg populations.

As both antigen-experienced $CD4^+$ T cells and $CD4^+$ Treg can also express CD25, conventional methods of identifying Treg on the basis of CD4/CD25 status are inadequate, leading to the potential for misinterpretation of data and incorrect associations of particular T cell populations with particular disease states. Indeed, at least part of the controversy surrounding the question of whether patients with allergic, autoimmune and immunoinflammatory diseases have primary deficiencies in Treg number or function stems from the difficulty in accurate identification of Treg. The range of constitutive CD25 expression by human Treg overlaps that of antigen-experienced activated/memory $CD4^+$ cells. In addition, Foxp3, although crucial for the development of Treg, is also expressed by activated T cells, and thus fails to provide clear separation of Treg and activated/memory $CD4^+$ cells (24). Hence, there is clearly a need for an improved method of accurately identifying and quantifying Treg populations.

The present invention is predicated on the surprising and unexpected finding by the inventors that Treg populations can be accurately defined by assessing the level of CD127 expressed on the surface of said populations.

SUMMARY OF THE INVENTION

According to a first aspect of the present invention there is provided a method for identifying a regulatory T cell or a population of regulatory T cells, the method comprising analyzing at least one cell within a primate biological sample to determine a level of cellular CD127, CD4 and CD25 expression, wherein $CD127^{low}CD4^+CD25^+$ expression is indicative of a regulatory T cell or a population of regulatory T cells.

The step of analyzing may further comprise determining a level of cellular expression for at least one additional cellular polypeptide or polynucleotide. The at least one additional cellular polypeptide or polynucleotide may be cell surface-associated or intracellular. The at least one additional cellular polypeptide or polynucleotide may comprise CD45RA, CD45RO, Foxp3, CTLA-4 and/or CD95.

The primate biological sample may comprise a cell line or a bodily fluid or tissue. The bodily fluid or tissue may comprise blood, lymph, thymus, lymph node, spleen or tonsil. The primate biological sample may comprise at least one isolated lymphocyte. The primate biological sample may comprise at least one T cell.

The step of analyzing may comprise an immunoassay. The immunoassay may comprise an enzyme-linked immunoassay or a radioimmunoassay. Additionally or alternatively, the step of analyzing may comprise flow cytometry. Additionally or alternatively, the flow cytometric analysis may comprise fluorescence activated cell sorting.

Additionally or alternatively, the level of cellular expression may be measured by polymerase chain reaction. The polymerase chain reaction may be quantitative real time polymerase chain reaction. Optionally the quantitative real time polymerase chain reaction may be carried out after fluorescence activated cell sorting.

In one embodiment the method comprises the steps of:
(a) obtaining a human biological sample;
(b) contacting at least one cell within the primate biological sample with antibodies directed towards cell surface CD127, CD4 and CD25;
(c) subjecting the at least one cell to flow cytometry; and
(d) analyzing the flow cytometry signal for $CD127^{low}CD4^+CD25^+$ expression
wherein $CD127^{low}CD4^+CD25^+$ expression is indicative of a regulatory T cell or a population of regulatory T cells.

The method may be used for isolating regulatory T cells.

The method may be used for diagnosing or monitoring autoimmune diseases, immunoinflammatory diseases, allergic diseases, predispositions thereto, infectious diseases, cancer, cancer treatment and/or organ transplantation.

The method may be used for predicting responses to therapy for autoimmune diseases, immunoinflammatory diseases, allergic diseases, predispositions thereto, infectious diseases, cancer and/or organ transplantation.

According to a second aspect of the present invention there is provided a method for identifying a regulatory T cell or a population of regulatory T cells, the method comprising analyzing at least one cell within a primate biological sample to determine a level of cellular CD127 expression, wherein the at least one cell within the sample has previously been assayed for CD4 and/or CD25 expression and found to be $CD4^+$ and/or $CD25^+$, and wherein $CD127^{low}CD4^+CD25^+$ expression is indicative of a regulatory T cell or a population of regulatory T cells.

Where the at least one cell has previously been assayed for CD4 expression, the step of analyzing further comprises determining a level of cellular CD25 expression.

Where the at least one cell has previously been assayed for CD25 expression, the step of analyzing further comprises determining a level of cellular CD4 expression.

The step of analyzing may further comprise determining a level of cellular expression for at least one additional cellular polypeptide or polynucleotide. The at least one additional cellular polypeptide or polynucleotide may be cell surface-associated or intracellular. The at least one additional cellular polypeptide or polynucleotide may comprise CD45RA, CD45RO, Foxp3, CTLA-4 and/or CD95.

The primate biological sample may comprise a cell line or a bodily fluid or tissue. The bodily fluid or tissue may comprise blood, lymph, thymus, lymph node, spleen or tonsil. The primate biological sample may comprise at least one isolated lymphocyte. The primate biological sample may comprise at least one T cell. The primate biological sample may comprise at least one $CD4^+$ T cell, at least one $CD25^+$ T cell or at least one $CD4^+CD25^+$ T cell.

The method may be used for isolating regulatory T cells.

The method may be used for diagnosing or monitoring autoimmune diseases, immunoinflammatory diseases, allergic diseases, predispositions thereto, infectious diseases, cancer, cancer treatment and/or organ transplantation.

The method may be used for predicting responses to therapy for autoimmune diseases, immunoinflammatory diseases, allergic diseases, predispositions thereto, infectious diseases, cancer and/or organ transplantation.

According to a third aspect of the present invention there is provided a kit for identifying in a primate subject a regulatory T cell or a population of regulatory T cells, the kit comprising at least one agent for determining a level of cellular expression of at least CD127.

The at least one agent may be selected from at least one anti-CD127 antibody and/or at least one oligonucleotide specific for CD127.

The kit may further comprise at least one agent for determining in a primate subject a level of cellular expression of at least one additional cellular polypeptide or polynucleotide. The at least one additional cellular polypeptide or polynucleotide may be selected from the group consisting of: CD4, CD25, CD45RA, CD45RO, Foxp3, CTLA-4 and/or CD95.

The kit may be used for isolating regulatory T cells.

The kit may be used for diagnosing or monitoring autoimmune diseases, immunoinflammatory diseases, allergic diseases, predispositions thereto, infectious diseases, cancer, cancer treatment and/or organ transplantation.

The kit may be used for predicting responses to therapy for autoimmune diseases, immunoinflammatory diseases, allergic diseases, predispositions thereto, infectious diseases, cancer and/or organ transplantation.

According to a fourth aspect of the present invention there is provided a kit for quantifying in a primate subject a population of regulatory T cells, the kit comprising at least one agent for determining a level of cellular expression of at least CD127.

The at least one agent may be selected from at least one anti-CD127 antibody and/or at least one oligonucleotide specific for CD127.

The kit may further comprise at least one agent for determining in a primate subject a level of cellular expression of at least one additional cellular polypeptide or polynucleotide. The at least one additional cellular polypeptide or polynucleotide may be selected from the group consisting of: CD4, CD25, CD45RA, CD45RO, Foxp3, CTLA-4 and/or CD95.

According to a fifth aspect of the present invention there is provided a method for quantifying the amount of regulatory T cells in a primate biological sample, the method comprising analyzing cells in the sample to determine a level of cellular CD127, CD4 and CD25 expression, wherein the quantity of $CD127^{low}CD4^+CD25^+$ cells in the sample is indicative of the quantity of regulatory T cells in the sample.

The step of analyzing may further comprise determining a level of cellular expression for at least one additional cellular polypeptide or polynucleotide. The at least one additional cellular polypeptide or polynucleotide may be cell surface-associated or intracellular. The at least one additional cellular polypeptide or polynucleotide may comprise CD45RA, CD45RO, Foxp3, CTLA-4 and/or CD95.

The primate biological sample may comprise a cell line or a bodily fluid or tissue. The bodily fluid or tissue may comprise blood, lymph, thymus, lymph node, spleen or tonsil. The primate biological sample may comprise at least one isolated lymphocyte. The primate biological sample may comprise at least one T cell.

The step of analyzing may comprise an immunoassay. The immunoassay may comprise an enzyme-linked immunoassay or a radioimmunoassay. Additionally or alternatively, the step of analyzing may comprise flow cytometry. Additionally or alternatively, the flow cytometric analysis may comprise fluorescence activated cell sorting.

Additionally or alternatively, the level of cellular expression may be measured by polymerase chain reaction. The polymerase chain reaction may be quantitative real time polymerase chain reaction. Optionally the quantitative real time polymerase chain reaction may be carried out after fluorescence activated cell sorting.

According to a sixth aspect of the present invention there is provided a method for quantifying the amount of regulatory T cells in a primate biological sample, the method comprising analyzing cells in the sample to determine a level of cellular CD127 expression, wherein the cells have previously been assayed for CD4 and/or CD25 expression and found to be $CD4^+$ and/or $CD25^+$, and wherein the quantity of $CD127^{low}CD4^+CD25^+$ cells in the sample is indicative of the quantity of regulatory T cells in the sample.

Where the cells have previously been assayed for CD4 expression, the step of analyzing further comprises determining a level of cellular CD25 expression.

Where the cells have previously been assayed for CD25 expression, the step of analyzing further comprises determining a level of cellular CD4 expression.

The step of analyzing may further comprise determining a level of cellular expression for at least one additional cellular polypeptide or polynucleotide. The at least one additional cellular polypeptide or polynucleotide may be cell surface-associated or intracellular. The at least one additional cellular polypeptide or polynucleotide may comprise CD45RA, CD45RO, Foxp3, CTIA-4 and/or CD95.

The primate biological sample may comprise a cell line or a bodily fluid or tissue. The bodily fluid or tissue may comprise blood, lymph, thymus, lymph node, spleen or tonsil. The primate biological sample may comprise at least one isolated lymphocyte. The primate biological sample may comprise at least one T cell. The primate biological sample may comprise at least one $CD4^+$ T cell, at least one $CD25^+$ T cell or at least one $CD4^+CD25^+$ T cell.

According to a seventh aspect of the present invention there is provided a method for diagnosing in a primate subject the over-production or under-production of regulatory T cells, the method comprising:

(a) obtaining a biological sample from said subject; and
(b) analyzing cells in the sample to determine a level of cellular CD127, CD4 and CD25 expression wherein a low quantity of $CD127^{low}CD4^+CD25^+$ cells in the sample is indicative of under-production of regulatory T cells in the subject, and a high quantity of $CD127^{low}CD4^+ CD25^+$ cells in the sample is indicative of over-production of regulatory T cells in the subject. An under-production of regulatory T cells may be associated with inflammatory bowel disease, or a predisposition thereto. An over-production of regulatory T cells may be associated with cancer or a viral infection. The cancer may be hepatocellular carcinoma. The viral infection may be HIV.

The method may include comparing the quantity of $CD127^{low}CD4^+CD25^+$ cells in the sample obtained from the primate subject with the quantity of $CD127^{low}CD4^+CD25^+$ cells at least one control sample. Typically a control sample may be a sample from a primate subject with no autoimmune, immunoinflammatory or allergic diseases, predispositions thereto, or other diseases that are associated with a change in the quantity of regulatory T cells.

According to an eighth aspect of the present invention there is provided a method for diagnosing in a primate subject a disease, the method comprising:

(a) obtaining a biological sample from said subject; and
(b) analyzing cells in the sample to determine a level of cellular CD127, CD4 and CD25 expression wherein a low quantity of $CD127^{low}CD4^+CD25^+$ cells in the sample is indicative of a disease in the subject. The disease may be inflammatory bowel disease, systemic lupus erythematosus, psoriatic arthritis, juvenile idiopathic arthritis, juvenile diabetes, Kawasaki disease or any other disease that is associated with a change in the quantity of regulatory T cells.

The method may include comparing the quantity of $CD127^{low}CD4^+CD25^+$ cells in the sample obtained from the primate subject with the quantity of $CD127^{low}CD4^+CD25^+$ cells in at least one control sample. Typically a control sample may be a sample from a primate subject with no autoimmune, immunoinflammatory or allergic diseases, predispositions thereto, or other diseases that are associated with a change in the quantity of regulatory T cells.

According to a ninth aspect of the present invention there is provided a method for monitoring the quantity of regulatory T cells in a primate subject during the course of a disease state, infection or therapy, the method comprising:

(a) obtaining a biological sample from said subject; and
(b) analyzing cells in the sample to determine a level of cellular CD127, CD4 and CD25 expression wherein the quantity of $CD127^{low}CD4^+CD25^+$ cells in the sample is indicative of the quantity of regulatory T cells in the sample, The disease state or infection may be selected from the group comprising autoimmune, immunoinflammatory or allergic diseases, or predispositions thereto, infectious diseases or cancer.

The therapy may be chemotherapy.

The method may include comparing the quantity of $CD127^{low}CD4^+CD25^+$ cells in the sample obtained from the primate subject with the quantity of $CD127^{low}CD4^+CD25^+$ cells in at least one control sample. Typically a control sample may be a sample from a primate subject with no autoimmune, immunoinflammatory or allergic diseases, or predispositions thereto, infectious diseases or cancer, or other diseases that are associated with a change in the quantity of regulatory T cells.

According to a tenth aspect of the present invention there is provided a method for predicting a response to therapy for a disease state or infection in a primate subject based on the quantity of regulatory T cells in the subject, the method comprising:

(a) obtaining a biological sample from said subject; and
(b) analyzing cells in the sample to determine a level of cellular CD127, CD4 and CD25 expression wherein the quantity of $CD127^{low}CD4^+CD25^+$ cells in the sample is indicative of the quantity of regulatory T cells in the sample, The disease state or infection may be selected from the group comprising autoimmune, immunoinflammatory or allergic diseases, or predispositions thereto, infectious diseases or cancer.

The therapy may be chemotherapy.

The method may include comparing the quantity of $CD127^{low}CD4^+CD25^+$ cells in the sample obtained from the primate subject with the quantity of $CD127^{low}CD4^+CD25^+$ cells in at least one control sample. Typically a control sample may be a sample from a primate subject with no autoimmune, immunoinflammatory or allergic diseases, or predispositions thereto, infectious diseases or cancer, or other diseases that are associated with a change in the quantity of regulatory T cells.

According to an eleventh aspect of the present invention there is provided a kit for use in the diagnosis of:

(a) the over-production or under-production of regulatory T cells in a primate subject;

(b) an autoimmune, immunoinflammatory or allergic disease, or predisposition thereto in a primate subject; and/or (c) a disease that is associated with a change in the quantity of regulatory T cells in a primate subject wherein said kit comprises at least one agent for analyzing a level of cellular expression of at least CD127.

The at least one agent may be selected from at least one anti-CD127 antibody and/or at least one oligonucleotide specific for CD127.

The kit may further comprise at least one agent for determining a level of cellular expression of at least one additional cellular polypeptide or polynucleotide. The at least one additional cellular polypeptide or polynucleotide may be selected from the group consisting of: CD4, CD25, CD45RA, CD45RO, Foxp3, CTLA-4 and/or CD95.

According to a twelfth aspect of the present invention there is provided a kit for use in monitoring the quantity of regulatory T cells in a primate subject during the course of a disease state, infection or therapy, wherein said kit comprises at least one agent for analyzing a level of cellular expression of at least CD127.

The at least one agent may be selected from at least one anti-CD127 antibody and/or at least one oligonucleotide specific for CD127.

The disease state or infection may be selected from the group comprising autoimmune, immunoinflammatory or allergic diseases, or predispositions thereto, infectious diseases or cancer.

The therapy may be chemotherapy.

The kit may further comprise at least one agent for determining a level of cellular expression of at least one additional cellular polypeptide or polynucleotide. The at least one additional cellular polypeptide or polynucleotide may be selected from the group consisting of: CD4, CD25, CD45RA, CD45RO, Foxp3, CTLA-4 and/or CD95.

According to a thirteenth aspect of the present invention there is provided a kit for use in predicting a response to therapy for a disease state or infection in a primate subject based on the quantity of regulatory T cells in the subject, wherein said kit comprises at least one agent for analyzing a level of cellular expression of at least CD127.

The at least one agent may be selected from at least one anti-CD127 antibody and/or at least one oligonucleotide specific for CD127.

The disease state or infection may be selected from the group comprising autoimmune, immunoinflammatory or allergic diseases, or predispositions thereto, infectious diseases or cancer.

The therapy may be chemotherapy.

The kit may further comprise at least one agent for determining a level of cellular expression of at least one additional cellular polypeptide or polynucleotide. The at least one additional cellular polypeptide or polynucleotide may be selected from the group consisting of: CD4, CD25, CD45RA, CD45RO, Foxp3, CTLA-4 and/or CD95.

According to a fourteenth aspect of the present invention there is provided a method for isolating a regulatory T cell or a population of regulatory T cells, the method comprising:

(a) analyzing at least one cell within a primate biological sample to determine a level of cellular CD127, CD4 and CD25 expression, wherein $CD127^{low}CD4^+CD25^+$ expression is indicative of a regulatory T cell or a population of regulatory T cells; and (b) isolating said at least one cell, wherein said at least one cell is $CD127^{low}CD4^+CD25^+$.

The step of analyzing may further comprise determining a level of cellular expression for at least one additional cellular polypeptide or polynucleotide. The at least one additional cellular polypeptide or polynucleotide may be cell surface-associated or intracellular. The at least one additional cellular polypeptide or polynucleotide may comprise CD45RA, CD45RO, Foxp3, CTLA-4 and/or CD95.

The primate biological sample may comprise a cell line or a bodily fluid or tissue. The bodily fluid or tissue may comprise blood, lymph, thymus, lymph node, spleen or tonsil. The primate biological sample may comprise at least one isolated lymphocyte. The primate biological sample may comprise at least one T cell.

The step of analyzing may comprise flow cytometry. Additionally or alternatively, the flow cytometric analysis may comprise fluorescence activated cell sorting.

In one embodiment the method comprises the steps of:

(a) obtaining a primate biological sample;

(b) contacting at least one cell within the primate biological sample with antibodies directed towards cell surface CD127, CD4 and CD25;

(c) subjecting the at least one cell to flow cytometry;

(d) analyzing the flow cytometry for $CD127^{low}CD4^+CD25^+$ expression; and (f) isolating $CD127^{low}CD4^+CD25^+$ cells by fluorescence activated cell sorting wherein $CD127^{low}CD4^+CD25^+$ expression is indicative of a regulatory T cell or a population of regulatory T cells.

According to a fifteenth aspect of the present invention there is provided a method for isolating a regulatory T cell or a population of regulatory T cells, the method comprising:

(a) analyzing at least one cell within a primate biological sample to determine a level of cellular CD127 expression, wherein the at least one cell within the sample has previously been assayed for CD4 and/or CD25 expression and found to be $CD4^+$ and/or $CD25^+$, and wherein $CD127^{low}CD4^+CD25^+$ expression is indicative of a regulatory T cell or a population of regulatory T cells; and (b) isolating said at least one cell, wherein said at least one cell is $CD127^{low}CD4^+CD25^+$.

Where the at least one cell has previously been assayed for CD4 expression, the step of analyzing further comprises determining a level of cellular CD25 expression.

Where the at least one cell has previously been assayed for CD25 expression, the step of analyzing further comprises determining a level of cellular CD4 expression.

The step of analyzing may further comprise determining a level of cellular expression for at least one additional cellular polypeptide or polynucleotide. The at least one additional cellular polypeptide or polynucleotide may be cell surface-associated or intracellular. The at least one additional cellular polypeptide or polynucleotide may comprise CD45RA, CD45RO, Foxp3, CTLA-4 and/or CD95.

The primate biological sample may comprise a cell line or a bodily fluid or tissue. The bodily fluid or tissue may comprise blood, lymph, thymus, lymph node, spleen or tonsil. The primate biological sample may comprise at least one isolated lymphocyte. The primate biological sample may comprise at least one T cell. The primate biological sample may comprise at least one CD4+ T cell, at least one CD25+ T cell or at least one CD4+CD25+ T cell.

According to a sixteenth aspect of the present invention there is provided at least one regulatory T cell when isolated by the method of the fourteenth or fifteenth aspects.

According to a seventeenth aspect of the present invention there is provided a method for regulatory T cell therapy using at least one regulatory T cell when isolated by the method of the fourteenth or fifteenth aspects.

DEFINITIONS

In the context of this specification, the term "comprising" means "including principally, but not necessarily solely". Furthermore, variations of the word "comprising", such as "comprise" and "comprises", have correspondingly varied meanings.

The term "expression" as used herein refers interchangeably to expression of a gene or gene product, including the encoded polypeptide or protein. Expression of a gene product may be determined, for example, by immunoassay using an antibody(ies) that bind with the polypeptide. Alternatively, expression of a gene may be determined by, for example, measurement of mRNA (messenger RNA) levels.

As used herein the term "polypeptide" means a polymer made up of amino acids linked together by peptide bonds. Accordingly, the term "polypeptide" includes within its scope a full length protein and fragments thereof.

As used herein the term "polynucleotide" means a nucleic acid made up of nucleotide residues linked together by a phosphodiester backbone. Accordingly, a polynucleotide includes within its scope DNA, RNA and in particular messenger RNA (mRNA).

As used herein the term "oligonucleotide" means a single-stranded nucleic acid capable of acting as a point of initiation of template-directed nucleic acid synthesis. An oligonucleotide is a single-stranded nucleic acid typically ranging in length from 2 to about 500 bases. The precise length of an oligonucleotide will vary according to the particular application, but typically ranges from 15 to 30 nucleotides. An oligonucleotide need not reflect the exact sequence of the template but must be sufficiently complimentary to hybridize to the template, thereby facilitating preferential amplification of a target sequence. Thus, a reference to an oligonucleotide as being "specific" for a particular gene or gene product, such as mRNA, includes within its scope an oligonucleotide that comprises a complementarity of sequence sufficient to preferentially hybridize to the template, without necessarily reflecting the exact sequence of the target polynucleotide.

As used herein the term "Treg" refers to regulatory T cells, either singular or plural.

As used herein, the terms "low" or "lo" are used interchangeably and refer to a level of expression of a particular molecule or polynucleotide, such as CD127, CD4 or CD25, by a particular cell or population of cells within a sample that is low when compared to the level of expression of that molecule or polynucleotide by the population of cells comprising the whole of the sample being analyzed. For example, the term "CD127$^{low}$" refers to a level of expression of CD127 by a particular cell or population of cells within the sample that is low when compared to the level of expression of CD127 by the population of cells comprising the whole of the sample being analysed. More particularly, the term "low" may refer to a distinct population of cells that express a particular molecule at a level that is lower than that expressed by one or more other distinct populations within a sample.

Similarly, the terms "high" or "bright" are used interchangeably and have a corresponding meaning. The term "int" may refer to a distinct population of cells that express a particular molecule at a level that is between that expressed by two or more other distinct populations within a sample. That is, the level of expression is lower than that expressed by one other distinct population of cells and higher than that expressed by another distinct population of cells.

As used herein, the term "+" when used in relation to levels of expression of a particular molecule or polynucleotide, refers to a level of expression of a particular molecule or polynucleotide, such as CD127, CD4 or CD25, by a particular cell or population of cells within a sample that is high or intermediate when compared to the level of expression of that molecule or polynucleotide by the population of cells comprising the whole of the sample being analyzed. For example, the term "CD4+" refers to a level of expression of CD4 by a particular cell or population of cells within the sample that is relatively high or intermediate when compared to the level of expression of CD4 by the population of cells comprising the whole of the sample being analysed.

As used herein, the term "−" when used in relation to levels of expression of a particular molecule or polynucleotide, refers to a level of expression of a particular molecule or polynucleotide, such as CD127, CD4 or CD25, by a particular cell or population of cells within a sample that is low when compared to the level of expression of that molecule or polynucleotide by the population of cells comprising the whole of the sample being analysed. For example, the term "CD4−" refers to a level of expression of CD4 by a particular cell or population of cells within a sample that is low when compared to the level of expression of CD4 by the population of cells comprising the whole of the sample being analysed.

As used herein, the terms "low" or "lo" may refer to a quantity of particular cells in a biological sample, such as CD127$^{low}$CD4+CD25+ cells, that is low when compared to the quantity of cells comprising the whole of the sample being analyzed. Additionally or alternatively, the term "low" may refer to a quantity of particular cells in a sample, such as CD127$^{low}$CD4+CD25+ cells, the proportion of which in relation to the whole of the sample being analyzed, is low when compared to a control sample. Typically a control sample may be a sample from a subject with no autoimmune, immunoinflammatory or allergic diseases, or predisposition thereto. The terms "high" or "bright" may have corresponding meanings.

BRIEF DESCRIPTION OF THE DRAWINGS

Embodiments of the present invention will now be described, by way of example only, with reference to the accompanying drawings:

FIG. 29: Comparison of circulating activated versus naïve Treg in patients with chronic renal failure (CRF), CRF on dialysis, and renal transplant. Transplant patients have significantly fewer CD45RA⁻ Treg as a result of treatment with immunosuppressive drugs.

BEST MODE OF PERFORMING THE INVENTION

Figure 1B:
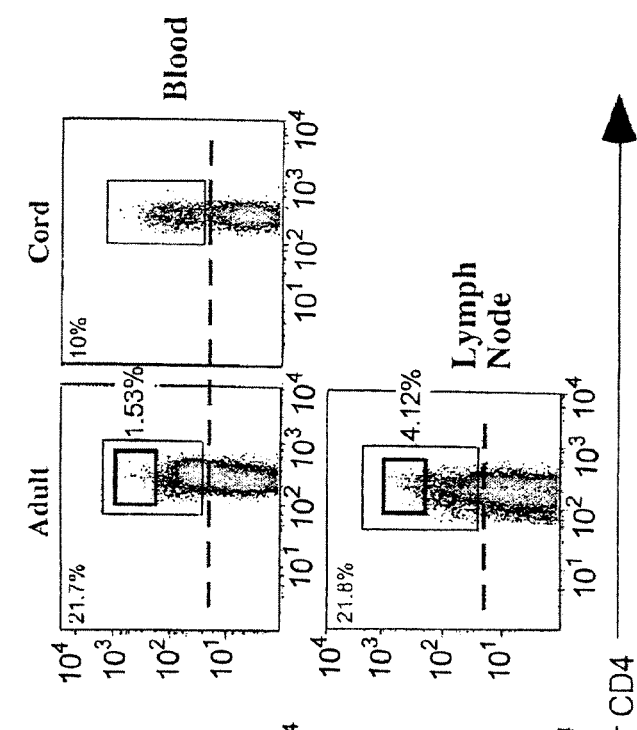
FIG. 1: Comparison of cell surface expression of CD4 versus CD25 in human and mouse peripheral blood leukocytes and lymph node cells by flow cytometry. Peripheral blood leukocytes and lymph node (LN) cells were stained using monoclonal antibodies to CD4 and CD25, and gated for live cells expressing CD4. (a) In mice, the number of conventional activated CD4+ T cells expressing CD25 is low, compared to the number of regulatory CD4+CD25+ cells, even when a large number of CD4+ T cells are actively proliferating ("stimulated" plots). (b) In adult human peripheral blood, up to 20-30% of CD4+ T cells express CD25, and many of these cells appear to be effector and memory cells resulting from encounter with foreign antigens. In contrast, the human cord blood profile resembles that of mice. The adult human lymph node profile is similar to that of adult human peripheral blood. (c) Comparison of expression of CD38, CD44, CD62L, OX40 and CTLA-4 between mouse and human peripheral blood CD4$^+$ T cells. Cells are gated for live cells expressing CD4. The expression pattern for human cells cannot be accurately predicted on the basis of the murine data. (d) Staining for 8 markers failed to distinguish human peripheral blood CD4$^+$CD25$^{high}$ T cells from activated/memory T cells. Peripheral blood leukocytes were stained for expression of CD4, CD25 and either HLA-DR, CD71, CCR7, CD45RA, CD27, CD58, CD95 or CD45RO. Profiles are gated for live cells expressing CD4. While CD45RA, CD45RO, CD58 and CD95 all revealed a second population of CD45RA$^+$ CD4$^+$ T cells, each of these antibodies failed to distinguish between CD45RO$^+$ CD4$^+$ Treg and conventional activated/memory T cells expressing CD25.

By testing a large panel of monoclonal antibodies directed towards surface molecules expressed by human CD4⁺ T cells, the inventors have shown using flow cytometry, fluorescence activated cell sorting (FACS) and real time quantitative PCR (RT-qPCR) that expression of CD127 splits human CD4⁺ CD25⁺CD45RO⁺ T cells into two populations with characteristics of Treg and activated/memory cells, respectively. Gating for expression of CD127 also allows for more clarity in separation of CD4⁺CD25⁺CD45RA⁺ Treg from activated conventional T cells that have not yet converted to expression of CD45RO. This surprising and unexpected finding appears in contrast to prior testing by the inventors of 38 other markers, many of which segregate Treg effectively in murine samples, but which failed to provide separation of CD4⁺ CD25⁺CD45RO⁺ Treg and CD4⁺CD25⁺CD45RO⁺ activated/memory cells (FIG. 1 and ref 20). Further, whilst prior studies have suggested a low level of expression of CD127 on the surface of murine regulatory T cells (25, 26), markers typically show distinctly different expression patterns between murine and human T cell samples (see FIG. 1C), thereby rendering extrapolation between species unpredictable. Moreover, and contrary to the accepted view, the inventors have demonstrated that the published difference in expression of CD127 between murine CD4+Treg and non-Treg is clearly insufficient for accurate gating of the two populations using CD127 alone, and further, that the use of CD25 and CD127 to co-stain murine CD4+ T cells has no advantage over the use of CD25 alone in terms of distinguishing between Treg and non-Treg (25, 26).

The present invention therefore relates generally to a strategy to isolate Treg from CD25⁺ conventional CD4⁺ T cells in primates on the basis of expression of CD127. As exemplified herein, cell surface staining for expression of CD127 could be applied in conjunction with gating for CD4 and CD25, or with the addition of gating for CD45 isoforms. The validity of the gating strategy was confirmed by three methods. Firstly, in vitro suppression assays indicated that CD127 expression split CD4⁺CD25⁺ T cells into two populations, with the CD127$^{lo}$ cells having suppressive activity whereas the CD127$^{hi}$ cells did not. Secondly, staining with antibodies directed to FoxP3 indicated that there was a correlation of more than 85% between CD25⁺CD127$^{lo}$ cells and CD25⁺ FoxP3⁺ cells within the CD4⁺ T cell population in multiple samples derived from human peripheral lymphoid tissues. Thirdly, RT-qPCR indicated high levels of Foxp3 mRNA expression in samples considered to represent Treg populations. Using this strategy, the present inventors have demonstrated that the CD127$^{low}$CD4⁺CD25⁺ Treg within either CD45RA positive or negative cells expressed at least 10-fold more Foxp3 mRNA than CD127$^{hi}$CD4⁺CD25⁺ T cells matched for expression of CD45 isoform.

The present invention therefore provides methods for identifying a regulatory T cell or population of regulatory T cells, for quantifying the amount of regulatory T cells and for separating viable regulatory T cells for further study or use in therapy. The methods may comprise assaying for the level of cellular CD127, CD4 and/or CD25 expression, wherein CD127$^{low}$CD4⁺CD25⁺ expression is indicative of a regulatory T cell or a population of regulatory T cells.

The methods may be used for isolating regulatory T cells. The isolated regulatory T cells may be used for a variety of purposes, including but not limited to, cell culture to amplify numbers of regulatory T cells for adoptive T cell transfer or autologous T cell transfer, which may or may not involve selecting particular T cell subsets from the amplified or pre-amplified cell culture. The isolated regulatory T cells may also be stored for therapy of a subject at a later date.

The methods may be used for diagnosing or monitoring autoimmune diseases, immunoinflammatory diseases, allergic diseases, predispositions thereto, infectious diseases, cancer, cancer treatment and/or organ transplantation.

The methods may be used for predicting responses to therapy for autoimmune diseases, immunoinflammatory diseases, allergic diseases, predispositions thereto, infectious diseases cancer and/or organ transplantation.

Those skilled in the art will readily appreciate that the inventive methods may be varied to account for the precise nature of the biological sample being assayed. For example, where the biological sample comprises a population of T cells not previously assayed for expression of any proteins or polynucleotides, the methods may comprise assaying for at least CD127, CD4 and CD25 expression. However, where the biological sample comprises a population of T cells that have previously been assayed for CD4 and/or CD25 expression, the methods may comprise assaying only for CD127 and CD25, or CD127 and CD4, respectively. In all cases, the inventive methods may be used in conjunction with other methods to further confirm the identity or quantity of regulatory T cells, for example, by assaying for the level of cellular expression of other proteins or polynucleotides, such as CD45RA, CD45RO, Foxp3, CTLA-4 and/or CD95.

Those skilled in the art will also readily appreciate that the inventive methods may be used in conjunction with other methods to further confirm the identity or quantity of regulatory T cells, for example, by assaying for the level of cellular expression of other proteins or polynucleotides, such as CD45RA, CD45RO, Foxp3, CTLA-4 and/or CD95.

In addition, the inventors have applied the CD4/CD25/CD45RA/CD127 gating strategy to 38 patients with inflammatory bowel disease (IBD) in comparison with 43 controls. The high degree of variability within conventionally gated CD25⁺CD4⁺ Treg, which is particularly apparent in patients suffering from immunoinflammatory conditions, was reduced by identification of contaminating CD127$^{hi}$CD4⁺ CD25⁺ cells, particularly in patients with ulcerative colitis. Use of the CD4/CD25/CD45RA/CD127 staining and gating strategy for comparison of IBD patients and normal controls showed that not only were a larger number of cells identified as Treg, but the patients consistently showed a decrease in the CD45RA+ subset of Treg. This decrease was particularly evident in patients between 15 and 30 years of age, corresponding to the peak age of onset of IBD. Use of the CD127 cell surface staining strategy removed much of the inter-patient variability that previously resulted from contamination of the CD25 gate with activated cells, and allowed an accurate estimate of the true numbers of regulatory T cells directly ex vivo.

Moreover, the inventors have compared Treg number and function between cord blood samples, young adults and elderly peripheral blood, and demonstrated using CD127 staining that Treg functional activity remains unaltered during the shift from CD45RA expression to expression of a CD45RO+ RA− phenotype.

Further experimental support for the use of CD127 in identifying Treg has also been demonstrated by the inventors using various other disease models, including Alzheimer's disease, severe atopic eczema, asthma, Sjogren's syndrome, HIV and melanoma, thereby demonstrating the use of CD127 in diagnosing a range of disease states.

Importantly, the inventors have also measured circulating Treg number in renal transplant patients verses those in chronic renal failure, with or without dialysis, based on identification of Treg using CD127, thereby further demonstrating the use of CD127 in monitoring responsiveness to therapy.

In particular, the inventors have applied the CD4/CD25/CD45RA/CD127 gating strategy to peripheral blood leukocytes from 18 patients with primary Sjogren's syndrome and 17 age and sex matched controls, and have demonstrated an increase in both naive and total Treg numbers in the primary Sjogren's syndrome group, independent of age. In 9 asthma patients who were skin prick test positive and who secreted interleukin-5 in response to stimulation with house dust mite antigen in vitro, the percentage of naive Tregs was significantly increased. The use of the CD4/CD25//CD127 strategy in 6 patients with severe atopic eczema and 7 controls indicated a 2.5-fold increase in total Treg cells. Primary Sjogren's syndrome, atopic eczema and atopic asthma all involve abnormal production of antibodies to specific substances. Thus immunopathologic diseases related to antibody production may therefore be associated with abnormally high numbers of Treg cells, particularly naïve Treg cells.

Additionally, the inventors have applied the CD4/CD25/CD45RO/CD127 gating strategy to peripheral blood leukocytes from patients infected with HIV. Four groups of patients were examined—those with primary infection (seroconverters) and those with chronic disease, subdivided into groups receiving no treatment, treatment with anti-retroviral agents, and those treated with anti-retroviral agents who developed immune reconstitution disease (IRD). The number of CD45RO+ Treg was increased in patients with IRD, and this may be related to the disease pathology. In addition, naïve Tregs were over-represented in patients with acute primary disease. Thus the method can be used to define abnormalities in Treg numbers in infectious diseases.

In recipients of renal transplants undergoing immunosuppressive therapy, the CD4/CD25/CD45RA/CD127 gating strategy showed that the number of CD45RA− Treg was significantly decreased whereas the number of CD45RA+ was not. Thus the method can be used to monitor Treg numbers in patients undergoing transplantation and immunosuppressive therapy.

In patients with melanoma, the CD4/CD25/CD127 gating strategy was applied to follow Treg numbers throughout the course of vaccination trials.

The same antibody combination was also used to quantify Tregs in non-human primates such as macaques, thereby demonstrating the applicability of the methods disclosed herein not only to humans but also to other primates.

The present invention therefore further provides methods for diagnosing in a subject the over- or under-production of regulatory T cells, wherein the amount of cells in a biological sample expressing $CD127^{low}CD4^+CD25^+$ is indicative of the over-production or under-production of regulatory T cells in the subject.

The present invention additionally provides methods for diagnosing in a subject an autoimmune, immunoinflammatory or allergic disease, or a disease that is associated with a change in the quantity of regulatory T cells, or a predisposition thereto, the methods comprising analysing a biological sample from the subject to determine the amount of cells in a biological sample expressing $CD127^{low}CD4^+CD25^+$, wherein a low amount of $CD127^{low}CD4^+ CD25^+$ cells in the sample is indicative of an autoimmune, immunoinflammatory or allergic disease, or a disease that is associated with a change in the quantity of regulatory T cells, or a predisposition thereto.

The present invention also provides for methods for monitoring the quantity of regulatory T cells in a subject during the course of a disease state, infection or therapy, the method comprising obtaining a biological sample from said subject, and analyzing cells in the sample to determine a level of cellular CD127, CD4 and CD25 expression, wherein the quantity of $CD127^{low}CD4^+CD25^+$ cells in the sample is indicative of the quantity of regulatory T cells in the sample, The present invention further provides for methods for predicting a response to therapy for a disease state or infection in a subject based on the quantity of regulatory T cells in the subject, the method comprising obtaining a biological sample from said subject, and analyzing cells in the sample to determine a level of cellular CD127, CD4 and CD25 expression, wherein the quantity of $CD127^{low}CD4^+CD25^+$ cells in the sample is indicative of the quantity of regulatory T cells in the sample, The present invention moreover provides for kits for identifying a regulatory T cell or population of regulatory T cells, comprising an agent(s) for analyzing at least one cell within a biological sample to determine a level of cellular expression of at least CD127. The kits may comprise further agents to further confirm the identity of regulatory T cells, for example, by assaying for the level of cellular expression of other cellular proteins or polynucleotides, such as CD45RA, CD45RO, Foxp3, CTLA-4 and/or CD95. The kits may also be varied to account for the precise nature of the biological sample being assayed. For example, the biological sample may comprise a population of T cells that either have or have not been previously assayed for CD4 and/or CD25 expression.

The kits may be used for isolating regulatory T cells. The isolated regulatory T cells may be used for a variety of purposes, including but not limited to, cell culture to amplify numbers of regulatory T cells for adoptive T cell transfer or autologous T cell transfer, which may or may not involve selecting particular T cell subsets from the amplified or pre-amplified cell culture. The isolated regulatory T cells may also be stored for therapy of a subject at a later date.

The kits may be used for diagnosing or monitoring autoimmune diseases, immunoinflammatory diseases, allergic diseases, predispositions thereto, infectious diseases, cancer, cancer treatment and/or organ transplantation.

The kits may be used for predicting responses to therapy for autoimmune diseases, immunoinflammatory diseases, allergic diseases, predispositions thereto, infectious diseases, cancer and/or organ transplantation.

The present invention therefore also provides for kits for use in diagnosing the over-production or under-production of regulatory T cells, an autoimmune, immunoinflammatory or allergic disease, a disease that is associated with a change in the quantity of regulatory T cells or a predisposition to an autoimmune, immunoinflammatory or allergic disease, or a disease that is associated with a change in the quantity of regulatory T cells, the kit comprising an agent(s) for analyzing expression of at least CD127 in at least one cell within a biological sample.

The present invention also provides for kits for use in monitoring the quantity of regulatory T cells in a subject during the course of a disease state, infection or therapy, wherein said kit comprises at least one agent for analyzing a level of cellular expression of at least CD127.

The present invention moreover provides for kits for use in predicting a response to therapy for a disease state or infection in a subject based on the quantity of regulatory T cells in the subject, wherein said kit comprises at least one agent for analyzing a level of cellular expression of at least CD127.

The present invention further provides methods for isolating a regulatory T cell or a population of regulatory T cells, the method comprising analyzing at least one cell within a biological sample to determine a level of cellular CD127, CD4 and CD25 expression, wherein $CD127^{low}CD4^+CD25^+$ expression is indicative of a regulatory T cell or a population of regulatory T cells, and isolating said at least one cell, wherein said at least one cell is $CD127^{low}CD4^+CD25^+$.

The step of analyzing may further comprise determining a level of cellular expression for at least one additional cellular polypeptide or polynucleotide. The at least one additional cellular polypeptides or polynucleotides may be cell surface-associated or intracellular. The at least one additional cellular polypeptide or polynucleotide may comprise CD45RA, CD45RO, Foxp3, CTLA-4 and/or CD95.

Persons of skill in the art will recognize that isolated regulatory T cells may be used for a variety of applications, including but not limited to in vitro manipulations such as expansion of Treg numbers, transfection and/or transformation. Other applications for isolated Treg may include infusion of Treg into subjects for therapy for diseases involving under- or aberrant expression of endogenous Treg. It will therefore be apparent that isolated Treg may be used for autologous Treg transfer and/or adoptive transfer of Treg as part of such therapies.

It will further be recognized by persons of skill in the art that isolated Treg may also be used for definition of Treg transcriptomes, mRNA profiling or in the preparation of antibodies for Treg identification and/or functional inhibition.

The present invention additionally provides methods for isolating a regulatory T cell or a population of regulatory T cells, the method comprising analyzing at least one cell within a biological sample to determine a level of cellular CD127 expression, wherein the at least one cell within the sample has previously been assayed for CD4 and/or CD25 expression and found to be CD4+ and/or CD25+, and wherein $CD127^{low}CD4^+CD25^+$ expression is indicative of a regulatory T cell or a population of regulatory T cells, and isolating said at least one cell, wherein said at least one cell is $CD127^{low}CD4^+CD25^+$. Where the at least one cell has previously been assayed for CD4 expression, the step of analyzing further comprises determining a level of cellular CD25 expression. Where the at least one cell has previously been assayed for CD25 expression, the step of analyzing further comprises determining a level of cellular CD4 expression.

The step of analyzing may further comprise determining a level of cellular expression for at least one additional cellular polypeptide or polynucleotide. The at least one additional cellular polypeptide or polynucleotide may be cell surface-associated or intracellular. The at least one additional cellular polypeptide or polynucleotide may comprise CD45RA, CD45RO, Foxp3, CTLA-4 and/or CD95.

The present invention additionally provides at least one regulatory T cell when isolated by the methods disclosed herein.

The present invention further provides for methods for regulatory T cell therapy using at least one regulatory T cell when isolated by the methods disclosed herein.

Those skilled in the art will appreciate that regulatory T cells may be identified, quantified and/or isolated in a variety of cell lines or bodily fluids or tissues, including but not limited to blood, lymph or thymus.

Particular embodiments of the invention provide the use of one or more antibodies raised against CD127, CD4, CD25, Foxp3, CTLA-4 and/or CD95 either free or in association with other molecules, for the detection of CD127, CD4, CD25, Foxp3, CTLA-4 and/or CD95 expression and the determination of Treg levels. The antibodies may be polyclonal or monoclonal and may be raised by the use of CD127, CD4, CD25, Foxp3, CTLA-4 and/or CD95 or an antigenic fragment or portion thereof as an antigen. Antibody binding may be detected by virtue of a detectable label on the primary CD127, CD4, CD25, Foxp3, CTLA-4 and/or CD95 antibody. Alternatively, the anti-CD127, -CD4, -CD25, -Foxp3, -CTLA-4 and/or -CD95 antibody may be detected by virtue of its binding with a secondary antibody or reagent that is appropriately labeled to enable detection. A variety of methods are known in the art for detecting binding in an immunoassay and are within the scope of the present invention. For example determinations of CD127, CD4, CD25, Foxp3, CTLA-4 and/or CD95 levels can be accomplished by any one of a number of techniques known in the art including, for example enzyme-linked immunosorbent assays (ELISA); sandwich immunoassays, immunoradiometric assays (IRMA), radioimmunoassays (RIA), immunoelectrophoresis assays, in situ immunoassays, immunodiffusion assays, immunofluorescence assays, Western blots, ligand-binding assays, and the like. Alternatively, determination of CD127, CD4, CD25, Foxp3, CTLA-4 and/or CD95 levels can be accomplished using anti-CD127, -CD4, -CD25, -Foxp3, CTLA-4 and/or CD95 antibodies as described above by flow cytometry, which may or may not involve fluorescence activated cell sorting (FACS).

Antibodies suitable for use in the methods of the present invention can be raised against CD127 using techniques known to those in the art. Suitable antibodies include, but are not limited to polyclonal, monoclonal, chimeric, humanised, single chain, Fab fragments, and a Fab expression library.

Suitable antibodies may be prepared from discrete regions or fragments of a CD127, CD4, CD25, Foxp3, CTLA-4 and/ or CD95 polypeptide. An antigenic CD127, CD4, CD25, Foxp3, CTLA-4 and/or CD95 polypeptide contains at least about 5, and typically at least about 10, amino acids.

Methods for the generation of suitable antibodies will be readily appreciated by those skilled in the art. For example, an anti-CD127, -CD4, -CD25, -Foxp3, -CTLA-4 and/or -CD95 monoclonal antibody, typically containing Fab portions, may be prepared using the hybridoma technology described in Antibodies-A Laboratory Manual, Harlow and Lane, eds., Cold Spring Harbor Laboratory, N.Y. (1988). In essence, in the preparation of monoclonal antibodies directed toward HbA1, fragment or analogue thereof, any technique that provides for the production of antibody molecules by continuous cell lines in culture may be used. These include the hybridoma technique originally developed by Kohler et al., Nature, 256: 495-497 (1975), as well as the trioma technique, the human B-cell hybridoma technique [Kozbor et al., Immunology Today, 4:72 (1983)], and the EBV-hybridoma technique to produce human monoclonal antibodies [Cole et al., in Monoclonal Antibodies and Cancer Therapy, pp. 77-96, Alan R. Liss, Inc., (1985)]. Immortal, antibody-producing cell lines can be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies and T-cell Hybridomas" (1981); Kennett et al., "Monoclonal Antibodies" (1980).

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques.

Similarly, there are various procedures known in the art which may be used for the production of polyclonal antibodies, or fragments or analogues thereof. For the production of polyclonal antibodies, various host animals can be immunized by injection with a CD127, CD4, CD25, Foxp3, CTLA-4 and/or CD95 polypeptide, or a fragment or analogue thereof, including but not limited to rabbits, mice, rats, sheep, goats, etc. Further, a CD127, CD4, CD25, Foxp3, CTLA-4 and/or CD95 polypeptide or fragment or analogue thereof can be conjugated to an immunogenic carrier, e.g., bovine serum albumin (BSA) or keyhole limpet hemocyanin (KLH). Also, various adjuvants may be used to increase the immunological response, including but not limited to Freund's (complete and incomplete), mineral gels such as aluminium hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

Screening for the desired antibody can also be accomplished by a variety of techniques known in the art. Assays for immunospecific binding of antibodies may include, but are not limited to, radioimmunoassays, ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, and immunoelectrophoresis assays, and the like (see, for example, Ausubel et al., eds, 1994, Current Protocols in Molecular Biology, Vol. 1, John Wiley & Sons, Inc., New York).

Additionally or alternatively, determinations of CD127, CD4, CD25, Foxp3, CTLA-4 and/or CD95 levels can be accomplished by polymerase chain reaction (PCR), including real-time quantitative PCR, wherein primers specific for polynucleotides encoding CD127, CD4, CD25, Foxp3, CTLA-4 and/or CD95 can be easily designed by a person skilled in the art for use in such PCRs.

Typically, according to methods of the invention the analysis of polynucleotide expression is carried out by PCR amplification. Amplified products may be further analysed by nucleic acid sequencing. PCR amplification may be conducted on polynucleotides extracted from cells, or alternatively sequences may be amplified directly without the need for prior polynucleotide purification steps.

The methods and reagents for use in PCR amplification reactions, subsequent fragment resolution, and nucleic acid sequencing are well known to those skilled in the art. In each case, suitable protocols and reagents will largely depend on individual circumstances. Guidance may be obtained from a variety of sources, such as for example Sambrook et al., *Molecular Cloning: A Laboratory Manual*, Cold Spring Harbor, N.Y., 1989, and Ausubel et al., *Current Protocols in Molecular Biology*, Greene Publ. Assoc. and Wiley-Intersciences, 1992. A person skilled in the art would readily appreciate that various parameters of these procedures may be altered without affecting the ability to achieve the desired product. For example, in the case of PCR amplification, the salt concentration may be varied or the time and/or temperature of one or more of the denaturation, annealing and extension steps may be varied. Similarly, the amount of polynucleotide used as a template may also be varied depending on the amount of polynucleotide available or the optimal amount of template required for efficient amplification.

The oligonucleotides for use in the methods and kits of the present invention are typically oligonucleotides of, generally, 15 to 30 bases in length. Such oligonucleotides can be prepared by any suitable method, including, for example, direct chemical synthesis or cloning and restriction of appropriate sequences. Not all bases in the oligonucleotide need reflect the sequence of the template molecule to which the oligonucleotide will hybridize, the oligonucleotide need only contain sufficient complementary bases to enable the oligonucleotide to hybridize to the template. An oligonucleotide may also include mismatch bases at one or more positions, being bases that are not complementary to bases in the template, but rather are designed to incorporate changes into the polynucleotide upon base extension or amplification. An oligonucleotide may include additional bases, for example in the form of a restriction enzyme recognition sequence at the 5' end, to facilitate cloning of the amplified polynucleotide.

Methods of the invention for determining Treg levels may include the step of comparing the level of Treg in a sample obtained from the subject of interest, for example an individual suspected of suffering from, or having a predisposition to, an autoimmune, immunoinflammatory or allergic diseases, or a disease that is associated with a change in the quantity of Treg, with the level of Treg from one or more control samples. Typically the control sample may be a sample from a subject with normal levels of Treg.

The present invention also provides kits for the determination of the level of Treg, wherein the kits facilitate the employment of methods of the invention. Typically, kits for carrying out a method of the invention contain all the necessary reagents to carry out the method. For example, in one embodiment the kit may comprise a first container containing an antibody raised against CD127, CD4, CD25, Foxp3, CTLA-4 and/or CD95 and a second container containing a conjugate comprising a binding partner of the antibody, together with a detectable label.

Typically, the kits described above will also comprise one or more other containers, containing for example, wash reagents, and/or other reagents capable of quantitatively detecting the presence of bound antibodies. Preferably, the detection reagents include labelled (secondary) antibodies or, where the antibody raised against CD127, CD4, CD25, Foxp3, CTLA-4 and/or CD95 is itself labelled, the compartments comprise antibody binding reagents capable of reacting with the labelled antibody.

In the context of the present invention, a compartmentalised kit includes any kit in which reagents are contained in separate containers, and may include small glass containers, plastic containers or strips of plastic or paper. Such containers may allow the efficient transfer of reagents from one compartment to another compartment whilst avoiding cross-contamination of the samples and reagents, and the addition of agents or solutions of each container from one compartment to another in a quantitative fashion. Such kits may also include a container which will accept the test sample, a container which contains the antibody(s) used in the assay, containers which contain wash reagents (such as phosphate buffered saline, Tris-buffers, and like), and containers which contain the detection reagent.

Typically, a kit of the present invention will also include instructions for using the kit components to conduct the appropriate methods.

Methods and kits of the present invention are equally applicable to any animal, including humans and other animals, for example including non-human primate, equine, bovine, ovine, caprine, leporine, avian, feline and canine species. Accordingly, for application to different species, a single kit of the invention may be applicable, or alternatively different kits, for example containing reagents specific for each individual species, may be required.

Methods and kits of the present invention find application in any circumstance in which it is desirable to determine Treg levels. The invention also finds application in the diagnosis of Treg under-expression or over-expression and the diagnosis of conditions of Treg under-expression or over-expression, or predispositions thereto, such as allergic diseases, autoimmune diseases, autoimmune diseases associated with immunodeficiency, diseases caused by inappropriate immune responses to environmental antigens, inflammatory bowel disease, inflammatory disease with immune involvement, infectious diseases in which the immune response itself causes disease, transplantation diseases, cancer and viral infections.

Similarly, the methods and kits of the present invention may also be applied to the testing and screening of animals, including but not limited to primates and other species contemplated herein.

The present invention will now be further described in greater detail by reference to the following specific examples, which should not be construed as in any way limiting the scope of the invention.

EXAMPLES

General Methods

Samples

Peripheral blood was obtained from healthy adult donors and patients with inflammatory bowel disease (Centenary Institute and the Royal Prince Alfred Hospital, Camperdown, NSW, Australia). Buffy coats were obtained from the Australian Red Cross Blood Service (Sydney, NSW, Australia). Cord blood samples from Nepean Hospital, Penrith, NSW, Australia, were obtained from umbilical cord veins immediately after delivery of the placenta. The neonates were fullterm and had no hematologic abnormalities or infectious complications. Normal thymus specimens were from children ages 1 to 7 months undergoing corrective cardiac surgery at the Children's Hospital, Westmead, NSW, Australia. The study was carried out with the approval of the Central and Western Sydney Area Health Services and the Royal Alexandra Hospital for Children Ethics Committee.

All other human peripheral blood samples were obtained with full patient consent and the approval of the appropriate Ethics Committees. The macaque study was performed with the approval of the University of Melbourne and CSIRO Livestock Industries Animal Experimentation and Ethics Committees.

Isolation of CD4 T Cells from Specimens

Peripheral blood, buffy coat and cord blood mononuclear cells were prepared by centrifugation over Ficoll-Paque gradients (Lymphoprep, Nycomed, Oslo, Norway).

The fresh operative specimens of thymus were dissociated by teasing through an 80-gauge stainless steel mesh and dispersing clumps by gentle pipeting. Lymph nodes were identified in operative specimens of bowel, dissected away from the bowel wall and dissociated by teasing through an 80-gauge stainless steel mesh and dispersing clumps by gentle pipeting. All single cell suspensions were stored frozen in liquid nitrogen and stained in batches for flow cytometric analysis.

Antibodies and Flow Cytometry

Anti-CD4, anti-CD25 and anti-CD45RO monoclonal antibodies (mAbs) (clones OKT4, 7GB6 and UCHTL-1 respectively) were labelled with Alexa488 (Molecular Probes, Oreg., USA) and FITC (Sigma) by standard protocols. The following mouse mAbs with specificity for human molecules were used in this study: biotin-, Alexa488-, FITC-, PE-, PerCp or PECy5-conjugated anti-CD3, -CD4, -CD5, -CD8, -CD38, -CD40L, -CD44, -CD45RA, -CD45RO, -CD54, -CD56, -CD57, -CD58, -CD62L, -CD69, -CD71, -CD74, -CD84, -CD95, -CD95L, -CD103, -CD122, -CD134, -CD152, -HLA-DR, CXCR4, CXCR5 (PharMingen, San Diego, Calif.), -CD21, -CD23, -CD25, -GITR (BD Biosciences, San Jose, Calif.), -CD27 (Ancell, Bayport, Minn.), -CD28, -CD30 (Miltenyi Biotec GmbH, Gladbach, Germany), -CD70, -CD127, -CD244 (Immunotech, Marseille, France), -CD148, -CD150 (DNAX Research Institute, Palo Alto, Calif.), CD11a (Caltag, Burlingame, Calif.) and Fox P3 (eBioscience or Biolegend). Biotin conjugates were developed with streptavidin conjugated with Alexa594 (Molecular Probes) or PerCp (PharMingen). PE- and FITC-conjugated anti-mouse mAbs (Southern Biotechnology, Birmingham, Ala.) were used detected unconjugated anti-CCR7 (PharMingen).

Single cell suspensions were washed with PBS containing 5% FCS and 5 mM sodium azide (FACS wash). Aliquots of $5 \times 10^5$ cells were stained in 96-well round-bottom PVC microtiter plates (ICN, Costa Mesa, Calif.) in FACS wash. The cells were washed and fixed in 1% formaldehyde if required. Intracellular staining was performed after fixation in 2% paraformaldehyde, followed by permeabilization and staining in buffer containing 0.1% saponin. Staining for FoxP3 was performed according to the manufacturer's instructions. A total of $1 \times 10^5$ events, gated for lymphocytes on the basis of forward and side scatter profiles, were collected using a FACSCalibur™ (Becton Dickinson, Mountain View, Calif.) or FACSVantage™ (BD Biosciences). Analysis was performed using the FlowJo program (Treestar, San Carlos, Calif.).

Fluorescence Activated Cell Sorting

Buffy coat mononuclear cells ($5 \times 10^8$) were stained with a combination of CD4-FITC, CD25-APC, CD127-PE and CD45RA-biotin monoclonal antibodies developed with streptavidin-Alexa594 or streptavidin-PerCP. Positive selection with anti-FITC beads (Miltenyi Biotech GmbH) was performed using an AutoMacs™ (Miltenyi Biotech) prior to sorting. Thymocytes (5×10⁸) were stained with a combination of CD4-PE-Cy5.5, CD3-PE, CD8-APC CD25-Alexa488, and CD45RA-biotin mAbs. Sorting was performed using a FACSVantage™ or FACSAria™ cell sorter.

Real Time qPCR

Total RNA was extracted from 1 to 5×10⁵ sorted cells after lysing in Trizol (Invitrogen, Life Technologies) for RNA extraction. The entire sample was reverse transcribed using Superscript II reverse-transcriptase and oligo(dT)$_{2-18}$ primer (Invitrogen) in a final volume of 20 µl. For real time quantitative PCR (RT qPCR), the reaction mixture (18 µl) contained 20 cDNA, 10 µl of Platinum SYBR Green SuperMix UDG (Invitrogen) and 0.25 pmoles forward and reverse primer. qPCR was performed on a Rotor-Gene 3000 system (Corbett research). Primers were designed so that amplicons spanned intron/exon boundaries to minimize amplification of genomic DNA. The primer sequences were as follows: Foxp3 sense, GGCAAATGGTGTCTGCAAGTG (SEQ ID NO: 1) and antisense, GGATGATGCCACAGATGAAGC (SEQ ID NO: 2). Primer sequences for other genes were: GATA3 sense AACTGTCAGACCACCACAACCACAC (SEQ ID NO: 3); GATA3 antisense GGATGCCTTCCTTCTTCATAGTCAGG (SEQ ID NO: 4); T-bet sense CACTACAGGATGTTTGTGGACGTG (SEQ ID NO: 5); T-bet antisense CCCCTTGTTGTTTGTGAGCTTTAG (SEQ ID NO: 6). Primers were supplied by Invitrogen. For β-actin, the primers were as follows: sense TCGACAACGGCTCCGGCATGTGCAAG (SEQ ID NO: 7) and antisense AGCCACACGCAGCTCATTGTAGAAG (SEQ ID NO: 8) (Sigma Genosys, Australia).

RT-qPCR for Foxp3, T-bet and GATA-3 was performed under the following conditions: stage 1: 94° C. for 5 min; stage 2: 94° for 20 s, 58° C. for 20 s and 72° C. for 20 s. An additional step at 75° C. for 15 s was added to reduce the primer dimer background. 45 cycles of amplification were carried out. The relative expression of Foxp3, T-bet and GATA-3 was determined by normalization to β-actin.

In Vitro Suppression Assays

In vitro suppression assays were performed in 96-well round bottom well plates in medium consisting of RPMI 1640 supplemented with 5% heat inactivated FCS, 2 mM L-Glutamine, 100U/ml penicillin and 100 µg/ml streptomycin. All wells contained 5×10⁴ APCs, 2×10⁴ responder cells (sorted CD4⁺CD25⁻CD45RA⁺ or CD4⁺CD25⁺ cells) and 0.25 µg/ml anti-CD3 (UCHT-1 or Hit3a, PharMingen). The number of putative suppressor cells added to each well was either 2×10⁴, 0.5×10⁴, 2×10³ or nil, giving final suppressor to responder ratios of 1:1, 0:251, 0.1:1, or 0:1 respectively. In control cultures, responders were added instead of suppressors. For CFSE assays, responders were labeled with CFSE and cell division was determined after 72 hours using flow cytometry. Percent proliferation was calculated relative to the mean number of divided cells in control wells containing only responder cells. For thymidine assays, preliminary experiments in which cultures were pulsed after 3, 4 or 5 days of culture indicated that the degree of suppression was stable over that period, so all subsequent cultures were pulsed with ³HTdR at 72 hours and harvested 16 hours later, to allow direct comparison of CFSE and thymidine assays.

Cytokines (IFN-γ, IL-4, IL-5, IL-10) were measured using OptEIA kits (BD) according to the manufacturer's instructions. Transwell assays were performed in 24-well plates as described previously (15).

Example 1

Figure 1A:
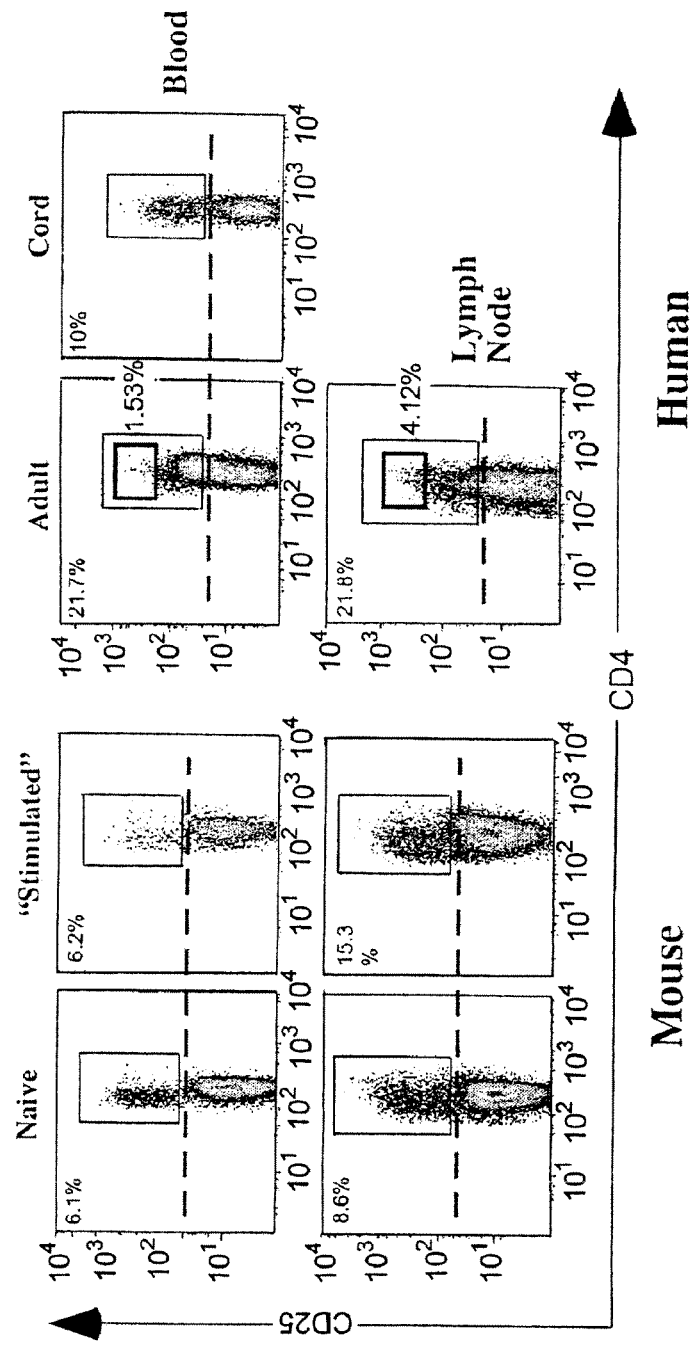
Figure 1C:
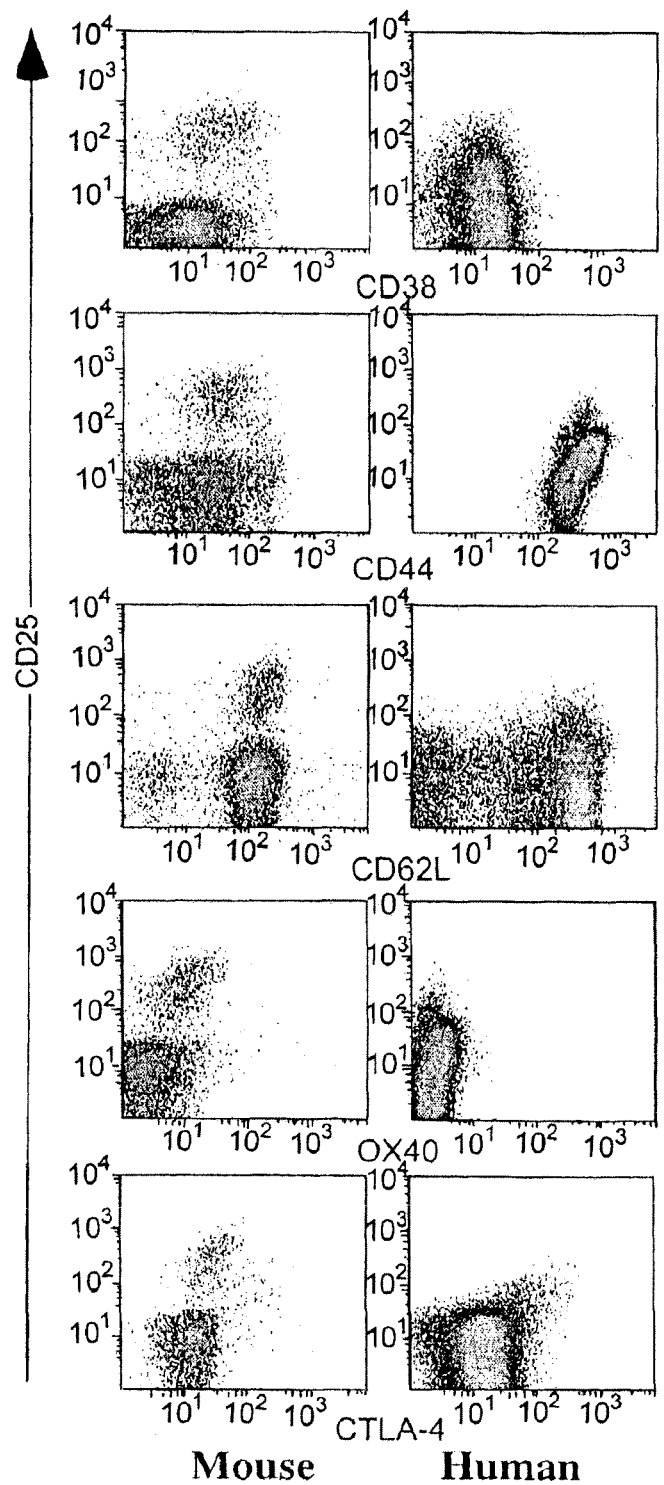
Figure 1D:
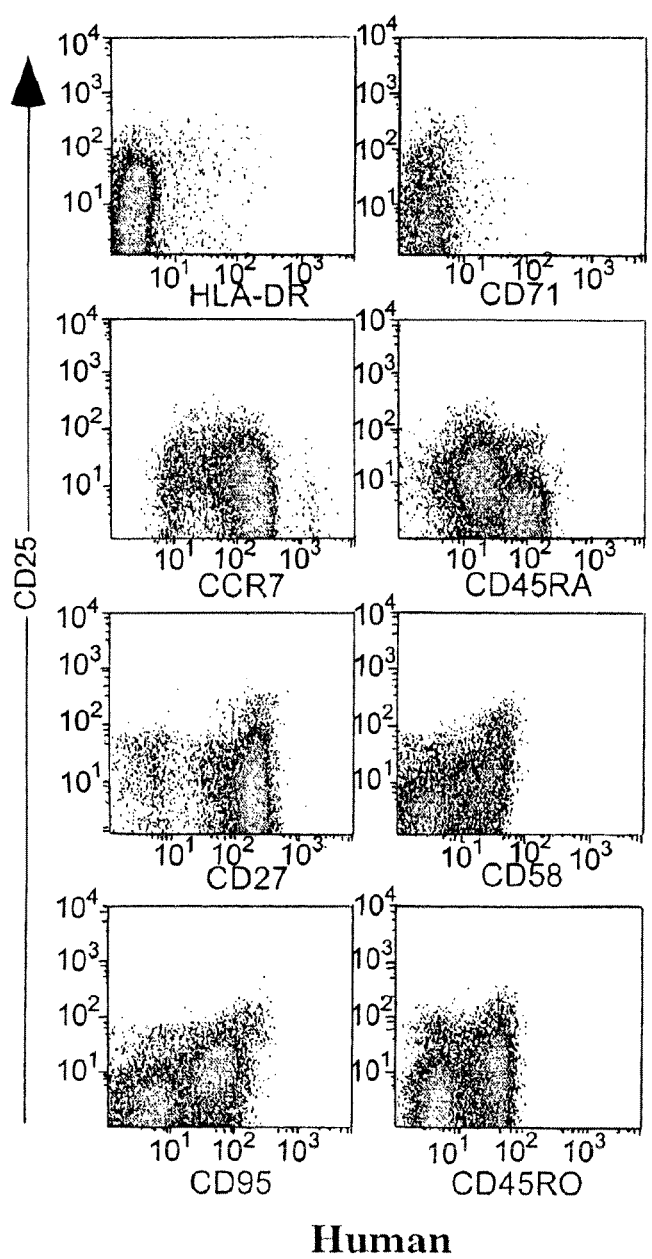

CD25 Expression by Human and Mouse CD4⁺ T Cells and Alternative Strategies for their Identification and Isolation FIGS. 1A and B illustrate the difference in expression of CD25 by mouse and human CD4⁺ T cells. In murine peripheral blood, a distinct population of 6% CD25-expressing cells is clearly distinguishable from the negative population (FIG. 1A). A similar profile of expression by 10% of CD4⁺ T cells is seen in human cord blood. However, the profile for adult blood CD4⁺ T cells is quite different, with only the 1-2% of cells expressing the highest levels of CD25 being distinguishable as a separate subpopulation, while the level of expression on the other 98% of cells ranges from intermediate to truly negative. Setting a gate at the level indicated by the cord blood profile (dotted line, FIG. 1B) transects the majority population of CD4⁺ T cells in adult peripheral blood. A similar gating dilemma is posed by human but not mouse lymph node. The major contributor to the species difference is the intermediate level of expression on a large proportion of human peripheral blood CD4⁺ T cells, which correspond to antigen-experienced "conventional" CD4⁺ cells. Even in mice in which a large fraction of CD4⁺ T cells is actively dividing (FIG. 1A "stimulated", which illustrates a homeostatically dividing population reconstituting RAG⁻ᐟ⁻ animals), the average level of CD25 expression on conventional activated T cells does not interfere markedly with identification of CD25⁺ Treg. The physiological significance of expression of high affinity IL-2 receptors on the majority of human antigen-experienced "conventional" CD4⁺ T cells remains unclear.

One further aspect of the staining pattern demonstrated in FIGS. 1A and B is that a distinct population of CD25$^{bright}$ cells in human adult blood shows a slight decrease in the expression of CD4. This decrease is also apparent in the entire population of CD25⁺ Treg in mice. Unfortunately the decrease is not large enough to allow its use in a gating strategy to distinguish Treg from antigen-experienced conventional T cells. However our studies in mouse models have indicated that, like constitutive expression of CD25, decreased expression of CD4 represents a highly stable phenotypic marker of Treg. In contrast, conventional T cells upregulate CD4 expression upon activation in vivo.

Figure 10:
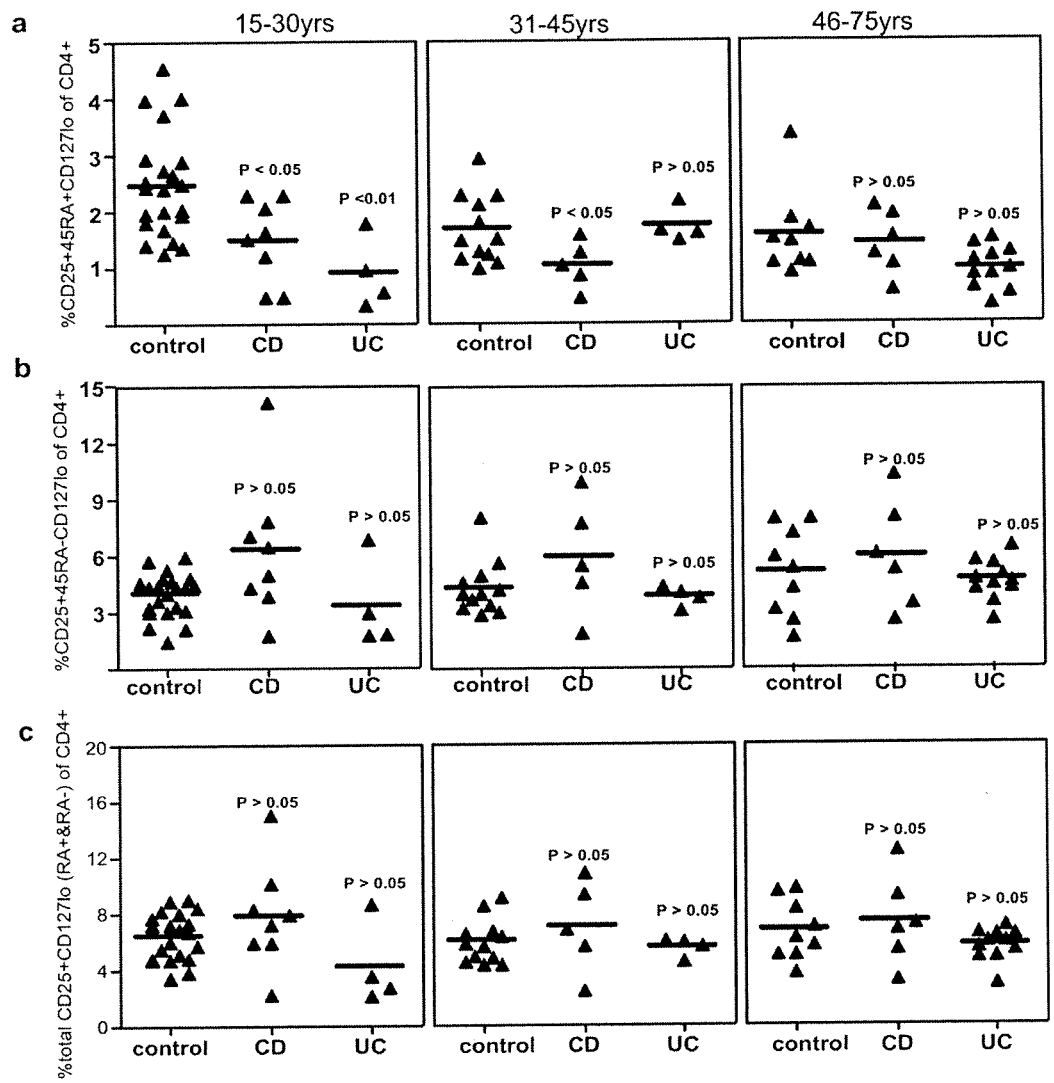
FIG. 10: Comparisons of Treg percentages in controls, CD and UC patients, divided into 3 age cohorts. Data are derived from the analysis presented in FIG. 7c. (a) CD4$^+$CD25$^+$CD45RA$^+$CD127$^{lo}$ cells (gate F, FIG. 7c) as a percentage of total CD4$^+$ T cells. (b) CD4$^+$CD25$^+$CD45RA$^-$CD127$^{lo}$ cells (gate E, FIG. 7c) as a percentage of total CD4$^+$ T cells. (c) Total CD4$^+$CD25$^+$CD127$^{lo}$ cells (data derived by adding individual data from gates E and F, FIG. 7c) as a percentage of total CD4$^+$ T cells. Nonparametric Kruskal-Wallis and Dunn's Multiple Comparison tests were applied to compare the median values of CD and UC to control groups. P-values <0.05 were considered significant.

Testing of 39 markers was undertaken in order to determine ability to identify subpopulations within CD4⁺ cells expressing CD25 at intermediate to high levels (CD25$^{int-hi}$, as identified by the dotted line in FIG. 1). To test whether markers that are useful in mice could accurately distinguish Treg in humans, the staining patterns for mouse and human were compared (FIG. 10). The data indicate that prediction of human patterns on the basis of mouse data is not possible. Further human markers were tested on adult blood. Expression of CD45RA identified a population of "naïve" Treg, which are present in thymus, cord blood, adult blood, lymph node and thymus. However within the CD45RA⁻RO⁺ population, none of the markers was differentially expressed by Treg and antigen-experienced cells (FIG. 1D), apart from CD127 (FIG. 2). Unlike CD45RO, CD58 and CD95, the level of CD127 expression in Treg was lower than that of naïve T cells, whereas expression in antigen-experienced cells was higher. Thus the profile of CD127 versus CD25 cells resembled that of CD4 versus CD25, but the range of CD127 expression was greater, allowing separation of human adult blood Treg by flow cytometric sorting. Particularly interesting was the cord blood profile, in which what appeared a single population in FIG. 1 was clearly separated into 2 populations after staining for expression of CD127.

Example 2

Expression of CD127 Distinguishes Between 2 Populations of Human CD25$^+$CD4$^+$ T Cells The capacity of CD127 expression to distinguish two populations of CD25$^+$CD4$^+$ T cells in a variety of lymphoid tissues was tested by staining samples of normal adult blood, lymph node, cord blood and thymus with mAbs to CD4, CD25 and CD127.

Figure 2A:
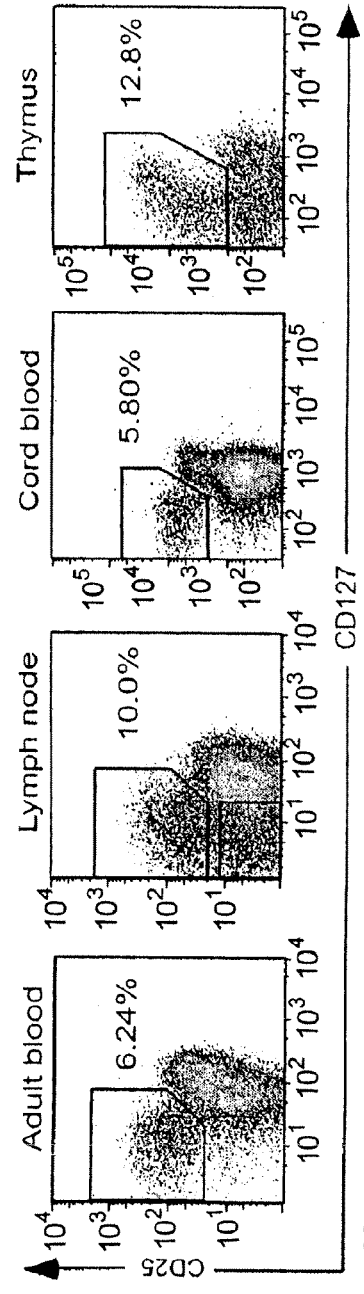
FIG. 2: Expression of CD127 and FoxP3 in adult blood, lymph node, cord blood and thymus. (a) Plots are gated for CD4$^+$CD8$^-$ T cells. CD25$^+$CD127$^{lo}$ cells are boxed and the % of cells in the box is shown. In the lymph node sample, CD25$^-$CD127$^{lo}$ cells are also boxed. (b) Plots are gated for CD4$^+$CD8$^-$ T cells. FoxP3$^+$CD127$^{lo}$ cells are boxed and the % of cells in the box is shown. (c) Correlation between FoxP3$^+$CD25$^+$ and CD25$^+$CD127$^{lo}$ phenotypes in peripheral blood. Gating of CD4$^+$ cells for each subset is shown, followed by the distribution of gated cells according to the reciprocal subset. (d) Correlation between FoxP3$^+$ and CD25$^+$CD127$^{lo}$ phenotypes in thymus.

Adult blood contained a population of CD25$^+$CD127$^{lo}$ cells distinct from the majority population of CD127$^{hi}$ cells (FIG. 2a). In addition to the CD25$^+$CD127$^{lo}$ population, lymph nodes also contained a significant number of CD25$^+$ CD127$^{hi}$ T cells, which were prominent in blood from a minority of normal adults (not shown). In cord blood, staining with anti-CD127 revealed that the CD25$^+$ population was not homogeneous, as previously claimed (27), but rather consisted of a mixture of CD25$^+$CD127$^{lo}$ and CD25$^+$CD127$^{hi}$ cells. In thymus, where antigen-experienced cells expressing CD25 are absent, cells with the highest levels of CD25 retained intermediate expression of CD127 (FIG. 2a).

Example 3

Figure 2B:
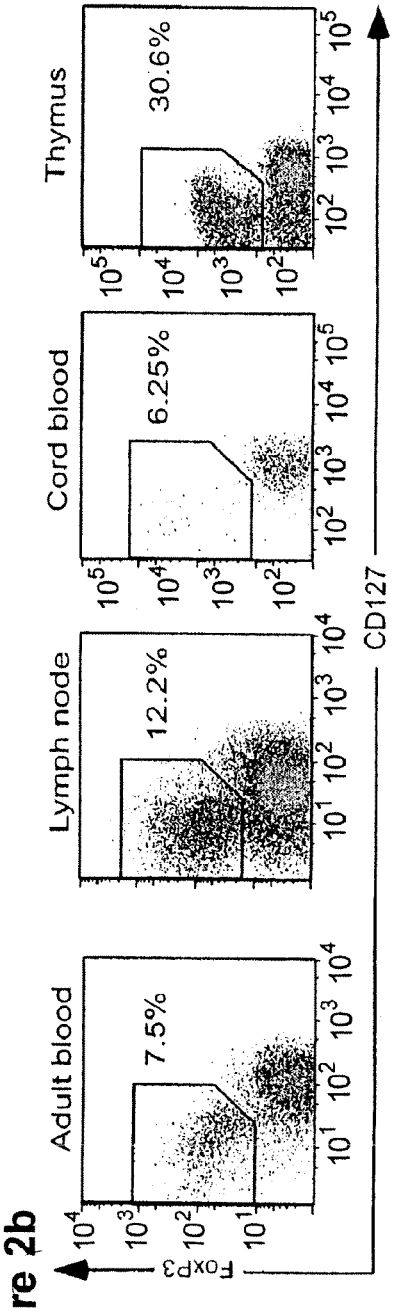
Figure 2C:
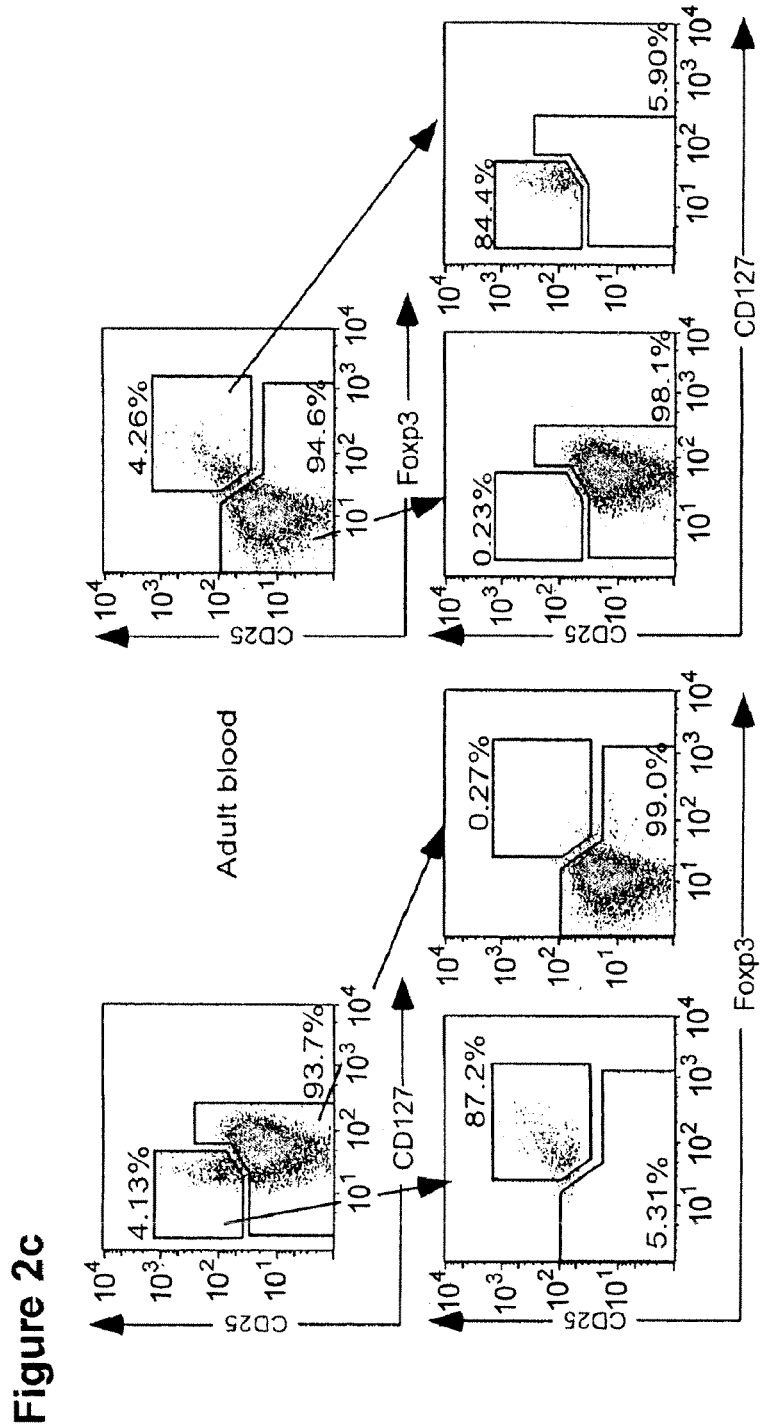
Figure 2D:
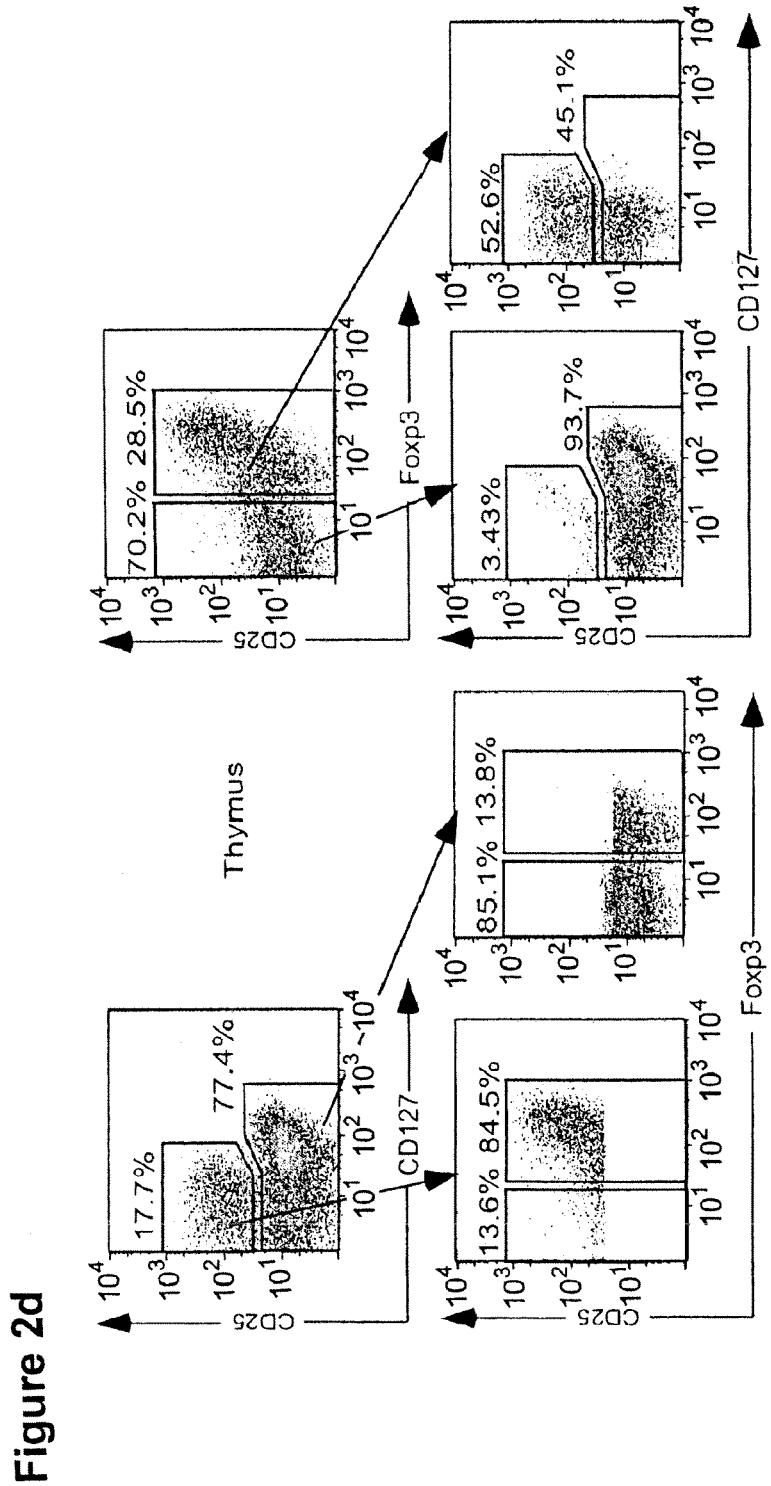

Inverse Correlation Between Expression of FoxP3 and CD127 in CD4$^+$CD25$^+$ T Cells To measure expression of Foxp3 protein within the CD25+CD127$^{lo}$ population, cells from adult and cord blood, lymph node and thymus were co-stained with mAbs to Foxp3 and CD127 (FIG. 2b). In blood and lymph node, the population of FoxP3$^+$ cells was CD127$^{lo}$ and similar in size to that of CD25$^+$ CD127$^{lo}$ cells in FIG. 2a. By contrast, the thymic FoxP3$^+$ population was considerably larger than the CD25$^+$CD127$^{lo}$ population. In peripheral blood, 87% of CD4$^+$CD127$^{lo}$ cells (gated as in FIG. 2c, top left panel) fell within the CD25$^+$ Foxp3$^+$ gate (FIG. 2c, bottom left panel), and conversely 84% of CD25$^+$Foxp3$^+$ cells were detected within the CD44$^+$ CD127$^{lo}$ gate (FIG. 2c, right panels). In thymic CD4$^+$CD8$^+$ T cells, however, 45% of Foxp3$^+$ cells were CD25$^-$ (FIG. 2d, bottom right panel), so that CD25$^+$CD127$^{lo}$ cells comprised a significantly smaller population than Foxp3$^+$ cells. Nonetheless, all thymic CD4$^+$CD8$^-$Foxp3$^+$ cells were CD127$^{lo}$. Thus the expression of CD25, CD127 and FoxP3 differed between thymus and peripheral blood.

Example 4

Correlation Between Expression of FoxP3 and CD127$^{lo}$ Phenotype

Figure 3A:
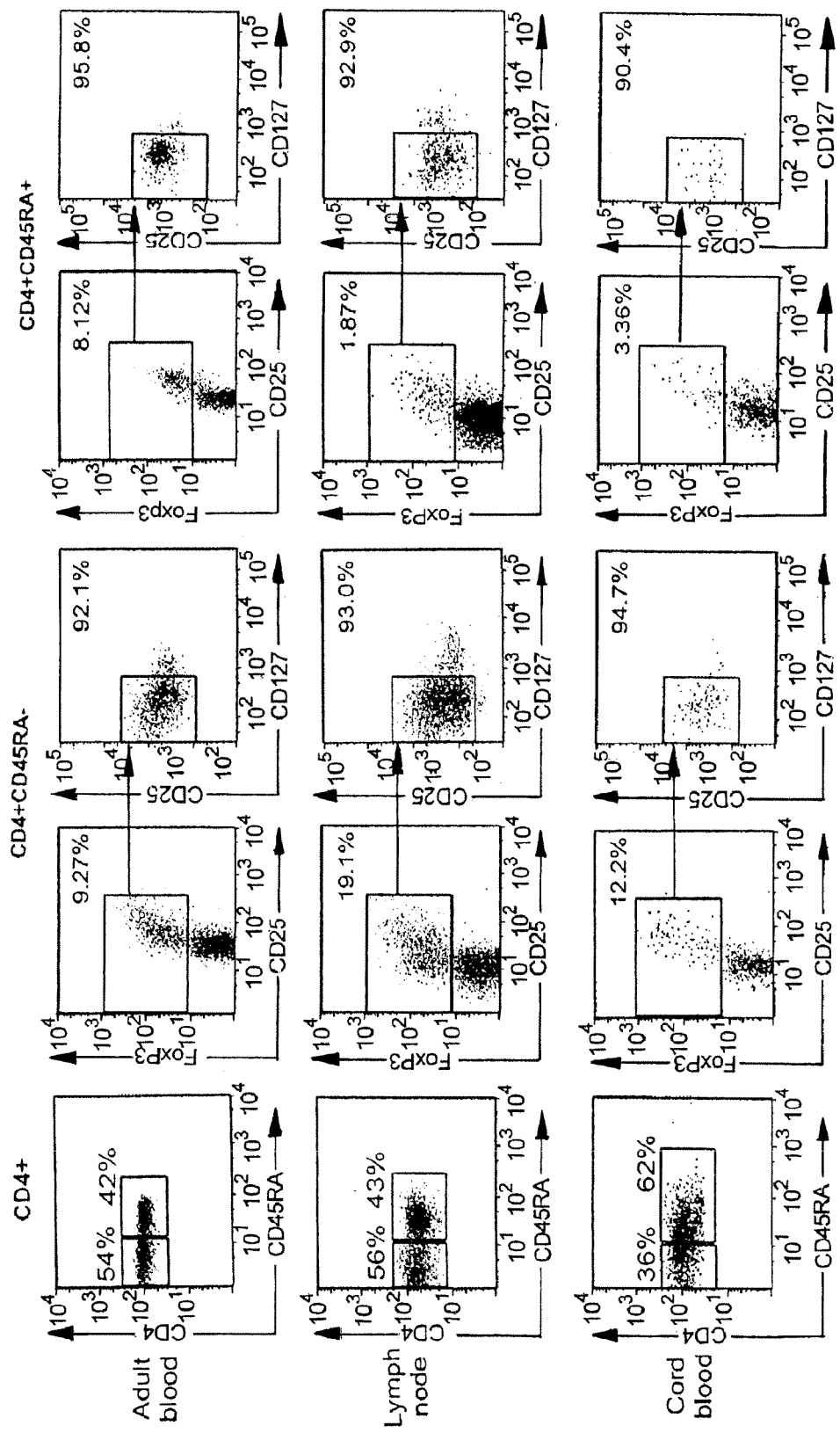
FIG. 3: Correlation between expression of FoxP3 and CD127$^{lo}$ phenotype. (a) Leukocytes from adult blood, lymph node and cord blood were gated into CD3$^+$CD4$^+$CD45RA$^+$ and CD45RA$^-$ populations. FoxP3$^+$ cells are boxed and the % of cells in the box is shown, together with expression of CD25 vs CD127 within the FoxP3$^+$ gate. (b) Correlation between the percentages of CD25$^+$CD127$^{lo}$ and CD25$^+$FoxP3$^+$ cells within CD4$^+$CD45RA$^+$ and CD45RA$^-$ populations in 9 peripheral blood samples from healthy volunteers.

To test whether a subset of naïve CD4$^+$CD45RA$^+$CD25$^+$ cells with regulatory activity also had a FoxP3$^+$CD127$^{lo}$ phenotype, the inventors stained adult blood, lymph node and cord blood cells with mAbs to CD3, CD4, CD45RA, CD25, CD127 and FoxP3 (FIG. 3a). CD3$^+$CD4$^+$ cells were separated into CD45RA$^-$ and CD45RA$^+$ subsets, and the percentage of CD25$^+$CD127$^{lo}$ cells within the Foxp3$^+$ gate was calculated. In all tissues, over 90% of total Foxp3$^+$ cells were CD25$^+$CD127$^{lo}$, while the remaining cells were CD25$^{int}$CD127$^{hi}$. Moreover the proportion of CD127$^{hi}$ cells was similar within the CD45RA$^-$ and CD45RA$^+$Foxp3$^+$ subsets.

Figure 3B:
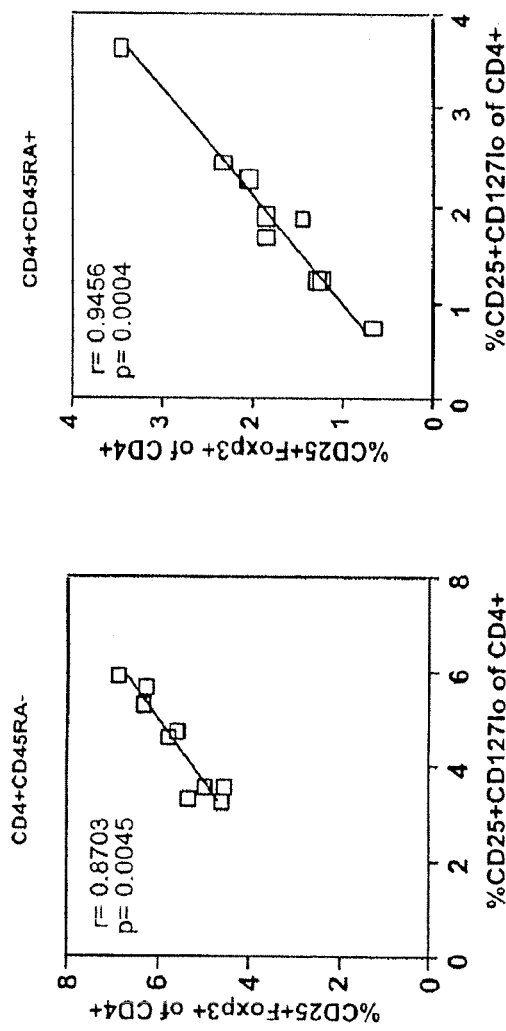

To determine the strength of the correlation between the percentage of cells within CD25$^+$CD127$^{lo}$ and CD25$^+$ FoxP3$^+$ populations, peripheral blood samples from 9 healthy volunteers were analysed (FIG. 3b). In both CD45RA$^-$ and CD45RA$^+$ subsets, the cell numbers within the two gates were very similar, indicating that the number of CD25$^+$ CD127$^{lo}$ cells correlates strongly with the number of CD25$^+$ FoxP3$^+$ cells in peripheral blood.

Example 5

Figure 4:
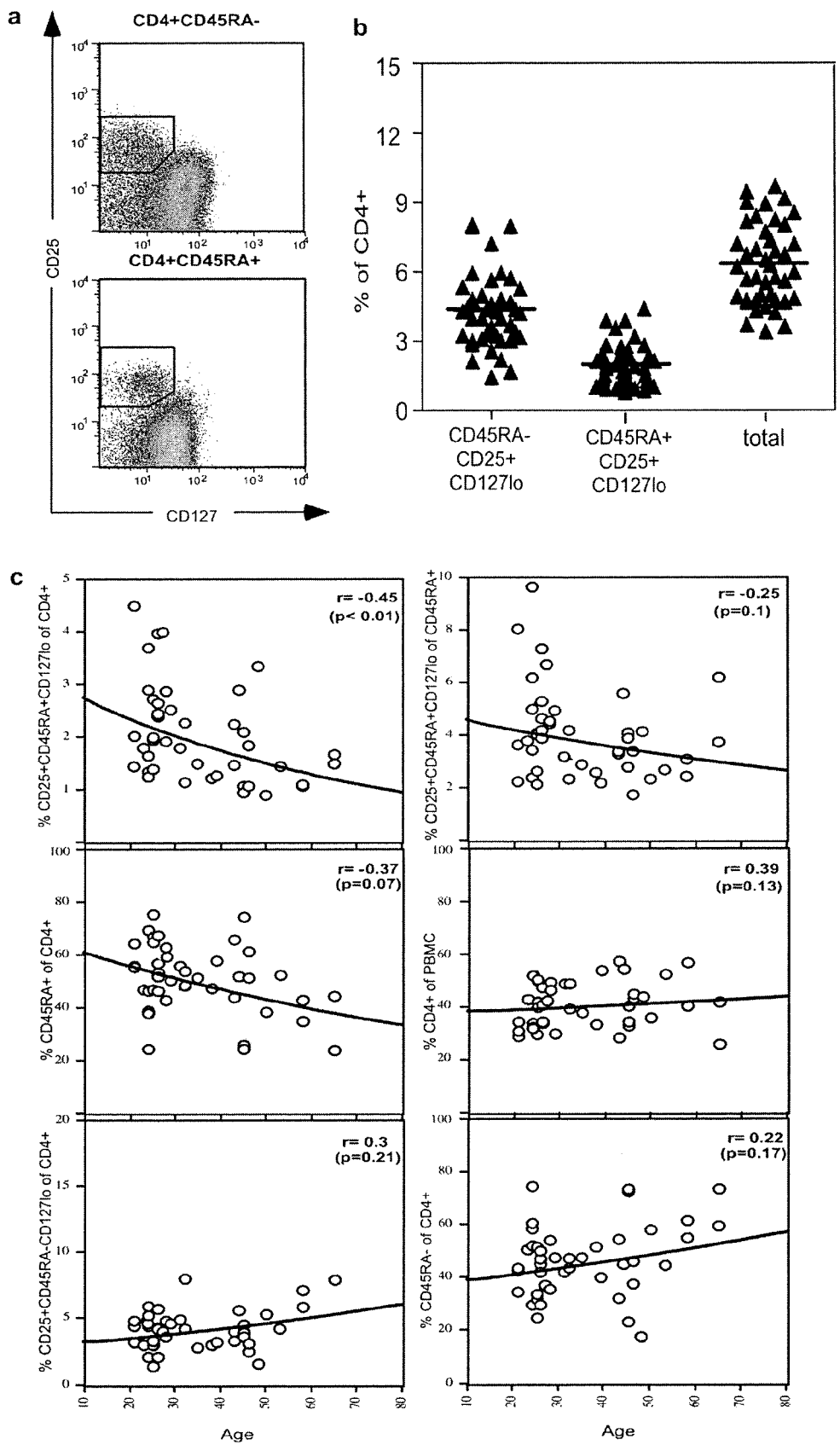
FIG. 4: Percentages of CD4$^+$CD25$^+$CD127$^{lo}$ cells in peripheral blood from 43 healthy volunteers. (a) Gating strategy for CD4$^+$ cells subdivided into CD45RA$^-$ and CD45RA$^+$ subpopulations. Boxes indicate the placement of the analysis gates for each cell population. (b) CD45RA$^-$ and CD45RA$^+$ CD25$^+$CD127$^{lo}$ cells, expressed as a percentage of total CD4$^+$ T cells. Total Treg percentages were derived by adding together the values for CD45RA$^-$ and CD45RA$^+$ Treg subsets. Horizontal bars represent the group means. (c) Relationship between various CD4$^+$ T cell subpopulations and age.

CD4$^+$CD25$^+$CD127$^{lo}$ Cell Numbers in Peripheral Blood of Healthy Volunteers To define normal levels of circulating CD4$^+$CD25$^+$ CD127$^{lo}$ cells, peripheral blood samples from a cohort of 43 healthy volunteers were examined (FIG. 4). The mean number (+/−SEM) of CD45RA$^-$CD25$^+$CD127$^{lo}$ cells as a percentage of CD4$^+$ T cells was 4.29+/−0.24, while the percentage of CD45RA$^+$CD25$^+$CD127$^{lo}$ cells was 2.05+/−0.14, giving a total of 6.35+/−0.26% of CD4$^+$ T cells (FIG. 4b). This was consistent with a figure of 6.42+/−0.50% of CD4$^+$ T cells in murine blood that was previously observed by the inventors (Tan and Fazekas de St Groth, unpublished data), and contrasts with the conventional estimate of 1-2% in human peripheral blood (19). Moreover the ratio of effector/memory to naïve Treg (FIG. 4a) was similar to the 2:1 ratio of effector to naive Treg that the inventors have previously determined for mice (Higgins and Fazekas de St Groth, unpublished data).

The inventors then demonstrated using CD4/CD25/CD45RA staining that the number of naïve Treg in peripheral blood declines as a function of age, suggestive of an effect of thymic involution (FIG. 4C). This decline was only partially attributable to the previously described loss of CD45RA$^+$ T cells with age. In contrast, the percentage of CD45RA$^-$ Treg was relatively stable throughout life, as was the percentage of CD4$^+$ T cells within peripheral blood leukocytes.

Example 6

Figure 5:
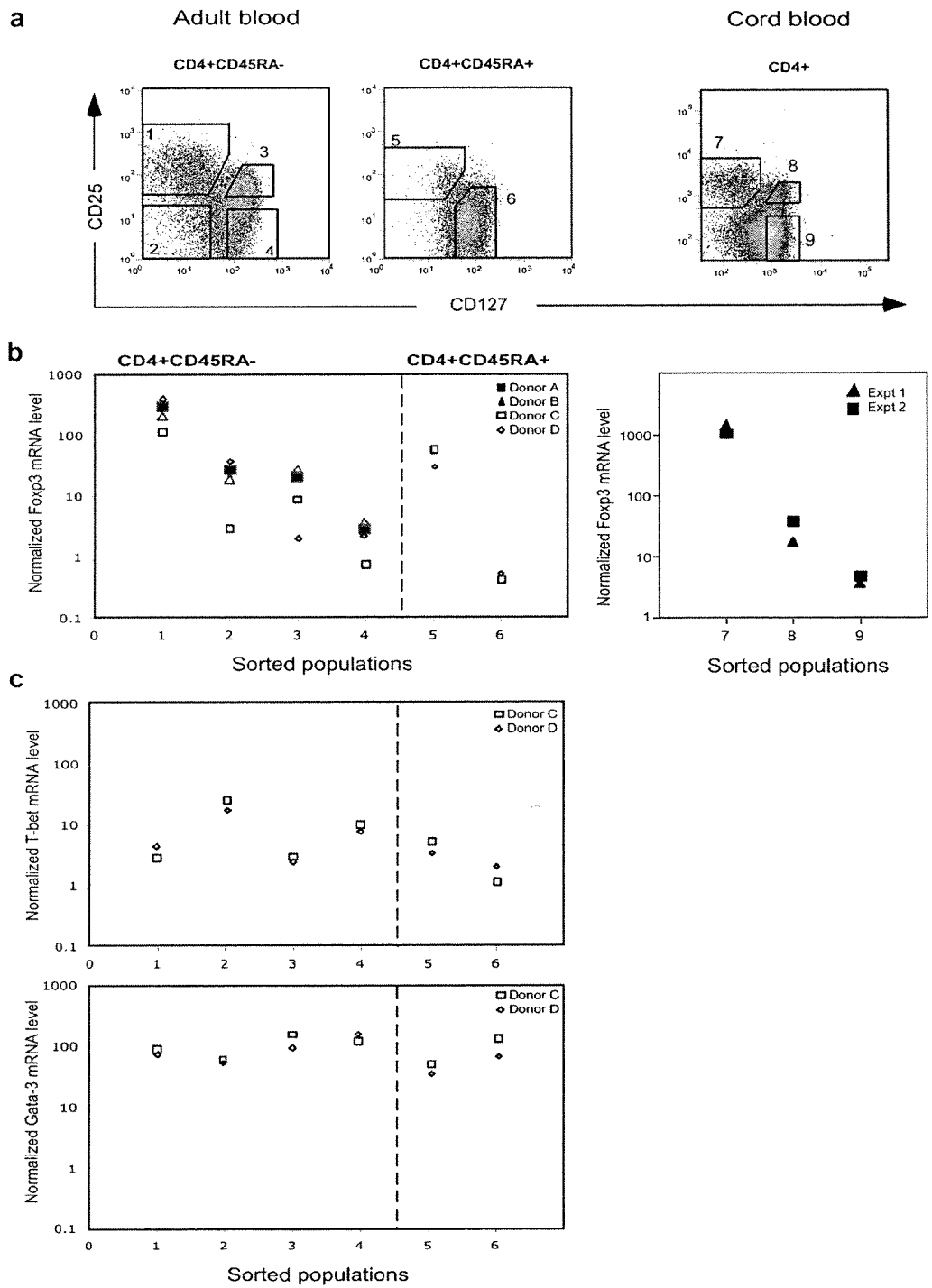
FIG. 5: Quantitative analysis of Foxp3 mRNA expression in sorted populations of CD4$^+$ T cells. (a) Sorting strategy for isolation of subsets of CD4$^+$ T cells from adult and cord blood. Dot plots are gated for lymphocytes expressing CD4, together with CD45RA in the case of adult blood. Numbered boxes indicate the placement of the flow sorting gates for each cell population. (b) RT qPCR for Foxp3 was performed in duplicate using RNA prepared from sorted cell populations. Sorted CD45RA$^-$ cells from 4 donors were compared, whereas sufficient CD45RA$^+$ cells were available from only 2 donors. (c) RT qPCR for T-bet and GATA3 using RNA prepared from sorted cell populations from 2 adult donors.

Measurement of mRNA for Transcription Factors in CD4$^+$ T Cell Subsets Sorted on the Basis of CD127 and CD25 Expression The inventors measured the level of Foxp3 mRNA within sorted subsets of peripheral blood CD4$^+$ T cells (FIG. 5a). CD25$^+$ CD45RA$^-$CD127$^{lo}$ cells (population 1) expressed 100-fold more Foxp3 mRNA than CD25$^-$CD45RA$^-$CD127$^{hi}$ cells (population 4, FIG. 5b). Intermediate levels of Foxp3 mRNA were present in CD25$^+$CD45RA$^-$CD127$^{hi}$ cells (population 3) and CD25$^-$CD45RA$^-$CD127$^{lo}$ cells (population 2). On the other hand, population 2 expressed the highest levels mRNA for T-bet, a master regulator of Th1 effector function, whereas GATA3 (a master regulator of Th2 function) was expressed equally by all populations (FIG. 5c). These results indicate that population 2 contains CD127$^{lo}$ effector cells. Within the CD45RA$^+$ fraction, CD25$^+$CD127$^{lo}$ cells expressed 100-fold more Foxp3 than naïve CD25$^-$ CD127$^{hi}$ cells (FIG. 5b).

In cord blood, CD25$^+$CD127$^{lo}$ cells expressed 500-fold more Foxp3 mRNA than the corresponding naïve CD4$^+$ CD25$^-$ cells (FIG. 5b, right panel). The CD25$^{int}$CD127$^{hi}$ population (population 8) of antigen-experienced T cells expressed an intermediate level of Foxp3, as demonstrated for the corresponding adult population (population 3, FIG. 5b).

Example 7

In vitro Suppression by Subsets Sorted on the Basis of CD127 Staining

Adult blood CD4$^+$ T cells divided into CD45RA$^+$ and CD45RA$^-$ subsets were sorted according to the gates illustrated in FIG. 6a (left panels). Autologous sorted CD45RA$^+$ CD25$^-$ cells (population 5) were used as responder cells in co-cultures to measure suppressive activity. Assays using either thymidine (FIG. 6b) or CFSE (not shown) as the indicator of cell proliferation showed that only the CD25$^+$CD127$^{lo}$ T cells within each CD45 subset (populations 1 and 3, FIG. 6b) mediated in vitro suppression. CD45RA$^+$ Treg were as potent as their CD45RA$^-$ counterparts. For cord blood assays, CD45 isoform expression was not used to subdivide cells, as the vast majority of cord blood cells express CD45RA to some extent. CD25$^+$CD127$^{lo}$ and CD25$^+$CD127$^{hi}$ subsets sorted according to the gates in FIG. 6a (right panel) were co-cultured with autologous responder CD4$^+$CD25$^-$CD127$^{hi}$ cells (population 8). Once again, both thymidine (FIG. 6b) and CFSE assays (not shown) indicated that the suppressive activity of CD4$^+$CD25$^+$ cells was confined to the CD127$^{lo}$ subset (population 6, FIG. 6b).

Previous reports have indicated that CD25$^{bright}$ but not CD25$^{int}$ cells have suppressive activity (19). However, in those studies the majority of cells in the CD25$^{int}$ gate would have been CD45RA$^-$ CD127$^{hi}$ conventional T cells (population 2, FIG. 6a, b), thereby compromising the efficiency of suppression in the assay. To compare the suppressive activity of CD45RA$^-$CD127$^{lo}$ cells expressing different levels of CD25, adult blood CD4$^+$ T cells divided into CD45RA$^+$ and CD45RA$^-$ subsets were sorted according to the gates illustrated in FIG. 6c. All three CD45RA$^-$CD25$^+$CD127$^{lo}$ populations (populations 9-11) manifested suppressive activity (FIG. 6d, lower left panel), consistent with their high level of FoxP3 expression (FIG. 2). In addition, all three populations suppressed IFNγ production by responder cells, and populations 10 and 11 secreted a small amount of IL-10. No secretion of IL-4 or IL-5 was detected in any cultures (data not shown). Interestingly, CD45RA$^-$ CD25$^-$CD127$^{lo}$ cells (population 12) showed some suppression of proliferation and IFNγ production, and secreted a detectable level of IL-10, although they did not express FoxP3 protein (FIGS. 2 and 3).

To test whether cell surface interaction between Treg and responder cells was required for suppression by CD25$^+$CD127$^{lo}$ cells, transwell cultures were performed (FIG. 6e). No suppression was seen when cell-cell contact between suppressor and responder cells was prevented, ruling out a role for soluble factors such as IL-10 in suppression by CD25$^+$CD127$^{lo}$ cells. Indeed, in the transwell cultures, the proliferation of responder cells was augmented when compared with the control cultures lacking suppressor cells (FIG. 6e).

Figure 6:
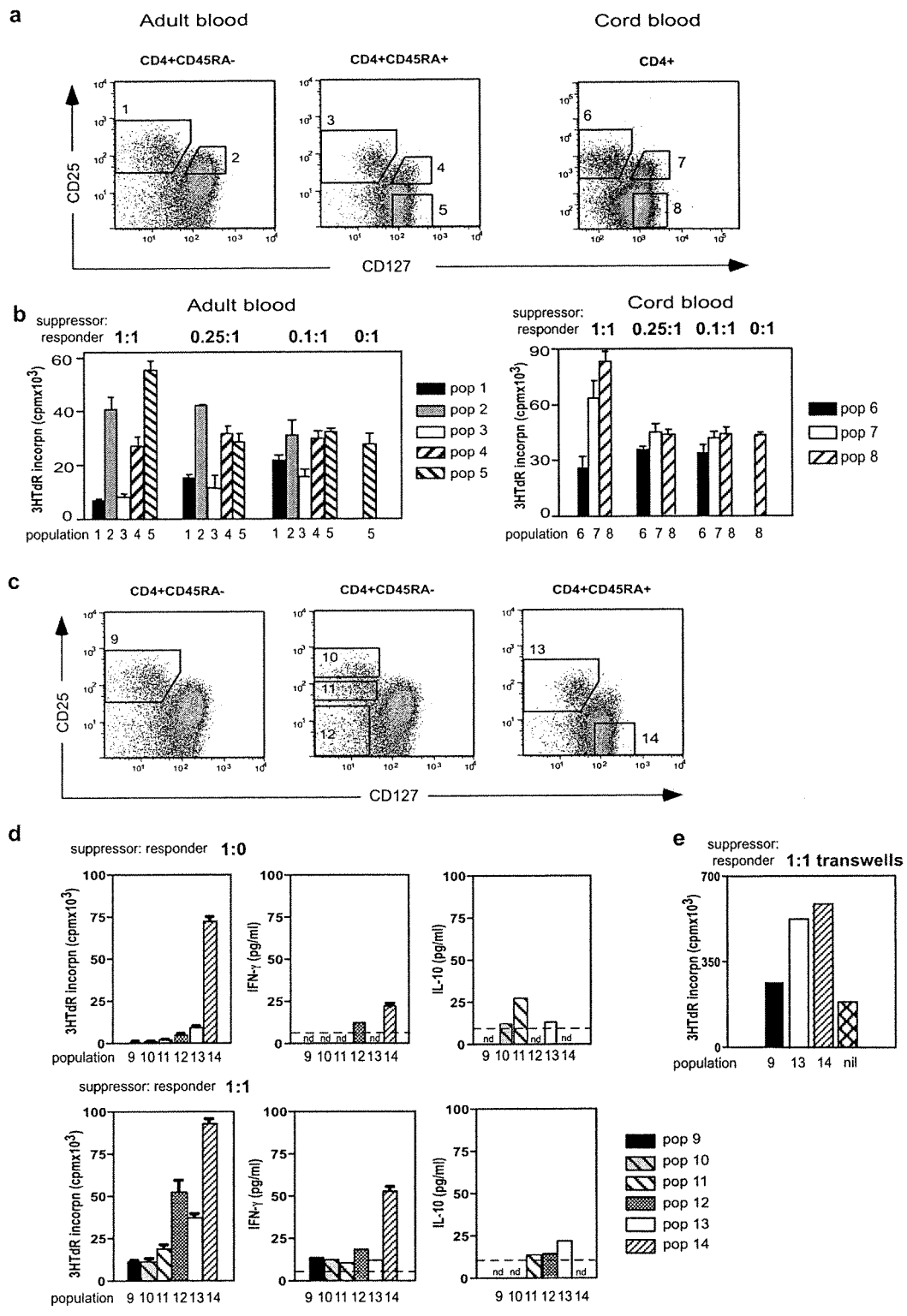
FIG. 6: Suppression of in vitro proliferation by Treg from adult and cord blood. (a) Sorting strategy for isolation of subsets of CD4$^+$ T cells. Dot plots are gated for lymphocytes expressing CD4, together with CD45RA in the case of adult blood. Numbered boxes indicate the placement of the flow sorting gates for each cell population. (b) Suppression by flow sorted populations (1-5) from adult blood and populations (6-8) from cord blood. Responder cells were sorted as autologous CD4$^+$CD45RA$^+$CD25$^-$ cells (population 5) for adult blood and autologous CD4$^+$ CD25$^-$ cells (population 8) for cord blood. Ratios of suppressor to responder cells are shown above the figure. Bars represent the mean+/−SEM of 3-4 replicate cultures. Assays of adult blood are representative of two independent experiments and the cord blood data are derived from a single experiment. (c) Strategy for isolation of subsets of CD4$^+$CD127$^{lo}$ T cells from adult blood, sorted on the basis of CD25 expression. (d) Suppression and cytokine production by flow sorted populations (9-14) from adult blood. Responder cells were sorted autologous CD4$^+$CD45RA$^+$CD25$^-$ cells (population 14). Limit of detection in the cytokine assays is indicated by the dotted line. nd: not detected. (e) Transwell cultures of flow sorted populations (9, 13-14 and nil) at a 1:1 ratio.

Taken together, these results indicate that suppressive activity was restricted to CD25$^+$CD127$^{lo}$ cells in both cord and adult blood. In contrast, markers such as HLA-DR, which splits CD4$^+$CD25$^+$ T cells into two populations, distinguish Treg subsets with different spectra of activity in vitro (28). A small proportion (less than 10%) of CD25$^+$FoxP3$^+$ cells retained high expression of CD127 (FIG. 3). The population of CD25$^+$CD127$^{hi}$ cells as a whole does not manifest suppressive activity in standard in vitro assays (FIG. 6). These data therefore indicate that expression of FoxP3 does not always confer obligatory suppressive function on human T cells.

Example 8

Comparison of Treg Numbers in IBD Patients and Control Subjects

Having shown that the CD4/CD25/CD127/CD45RA staining strategy provided added clarity in distinguishing Treg from activated T cells, the inventors applied the method to peripheral blood samples from a cohort of 43 control and 38 IBD patients (Table 1).

TABLE 1

| Subject characteristics | | | | | |
|---|---|---|---|---|---|
| Subject | Number | | | Age | |
| group | total | female | male | median | range |
| control | 43 | 15 | 28 | 29 | 21-65 |
| active CD | 12 | 6 | 6 | 32 | 17-65 |
| inactive CD | 7 | 3 | 4 | 41 | 22-72 |
| active UC | 9 | 4 | 5 | 35 | 24-54 |
| inactive UC | 10 | 4 | 6 | 54.5 | 30-71 |

Figure 7:
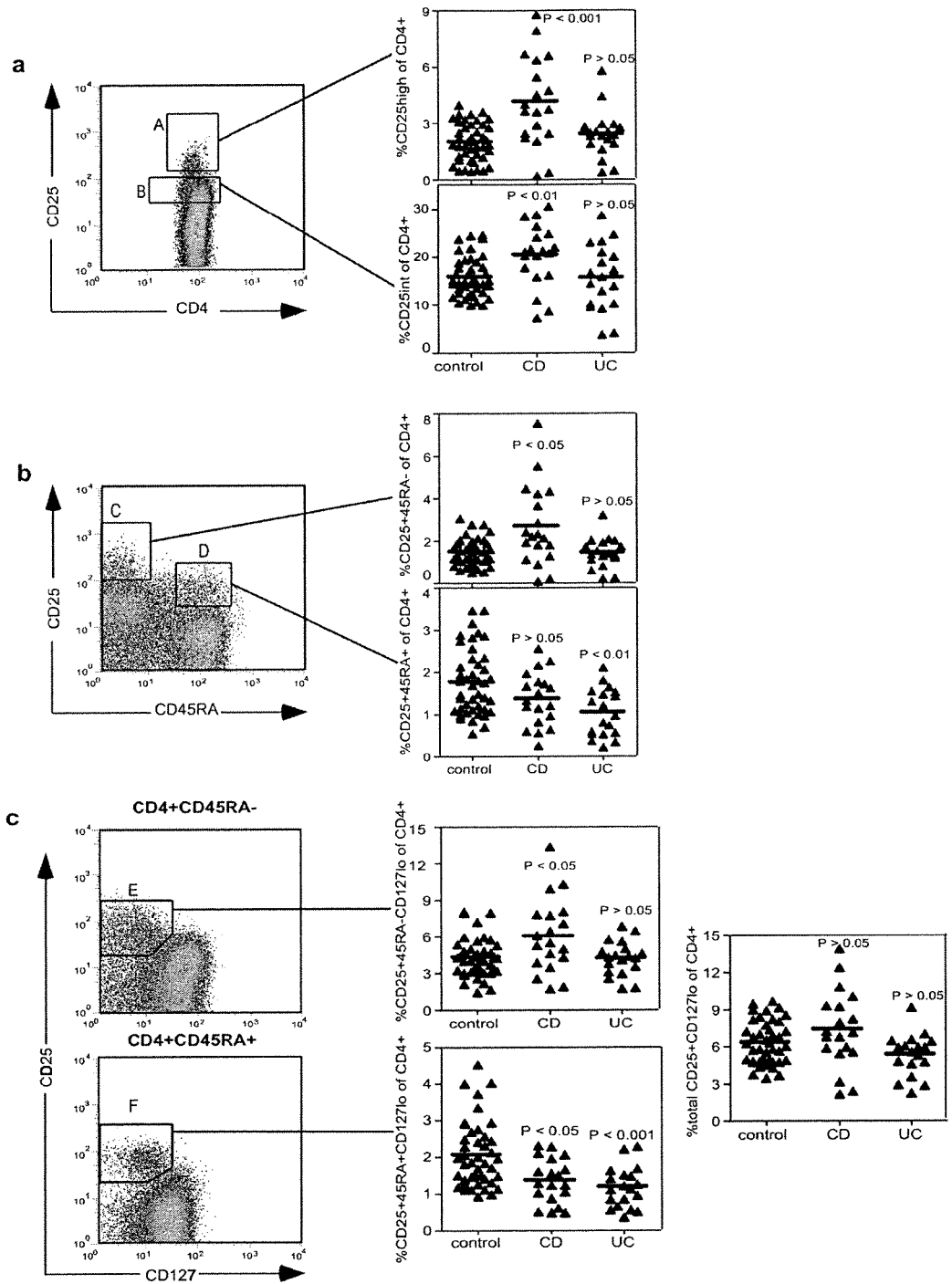
FIG. 7: Comparison of Treg numbers in controls and IBD patients using various gating strategies. PBMC from 43 control and 38 IBD patients (comprising 19 Crohn's disease (CD) patients and 19 ulcerative colitis (UC) patients) were purified from blood and stained with mAbs to CD4, CD25, CD127 and CD45RA. (a, b) Lymphocytes expressing CD4 were analysed according to gates A to D and the individual data points plotted as a percentage of CD4$^+$ T cells. (c) Lymphocytes expressing CD4 were subdivided into CD45RA$^+$ and CD45RA$^-$ populations, analysed according to gates E and F and the individual data points plotted as a percentage of CD4$^+$ T cells. The values in the far right box were derived by addition of the individual values derived from gates E and F. Horizontal bars represent the group means. Mean+/−SEM as % of CD4$^+$ T cells for gates E, F and E+F were as follows: naïve Treg (gate E), control 2.05+/−0.14, CD 1.34+/−0.14, UC 1.16+/−0.13; effector/memory Treg (gate F), control 4.29+/−0.24, CD 6.05+/−0.69, UC 4.19+/−0.32; total Treg (gates E+F), control 6.35+/−0.26, CD 7.39+/−0.72, UC 5.34+/−0.38. Statistical analysis of differences between groups used nonparametric Kruskal-Wallis and Dunn's Multiple Comparison tests, comparing the median values of CD and UC to control groups. P-values <0.05 were considered significant.

The flow cytometry data were analyzed using a number of gating strategies, to highlight the advantages in using the CD127-dependent method (FIG. 7). Both the conventional "CD25$^{bright}$" and the "CD25$^{int}$" strategies (labelled gates A and B, respectively in FIG. 7a) showed a wider range of values in IBD patients compared to controls, with a statistically significant increase in CD patients. The inventors had previously used a strategy based on differential expression of CD45 splice variants, in which the CD45RO gate (gate C, FIG. 7b) was similar to the CD25bright gate, while the CD45RA gate defined a novel subset of naïve Treg (gate D, FIG. 7b). The new CD4/CD25/CD45RA/CD127 staining strategy described here was applied as indicated by gates E and F (FIG. 7c). Once again, CD patients showed a significant increase in CD45RA$^-$ Treg numbers. Significant decreases in the percentage of naïve Treg were seen in both CD and UC patients.

Figure 8:
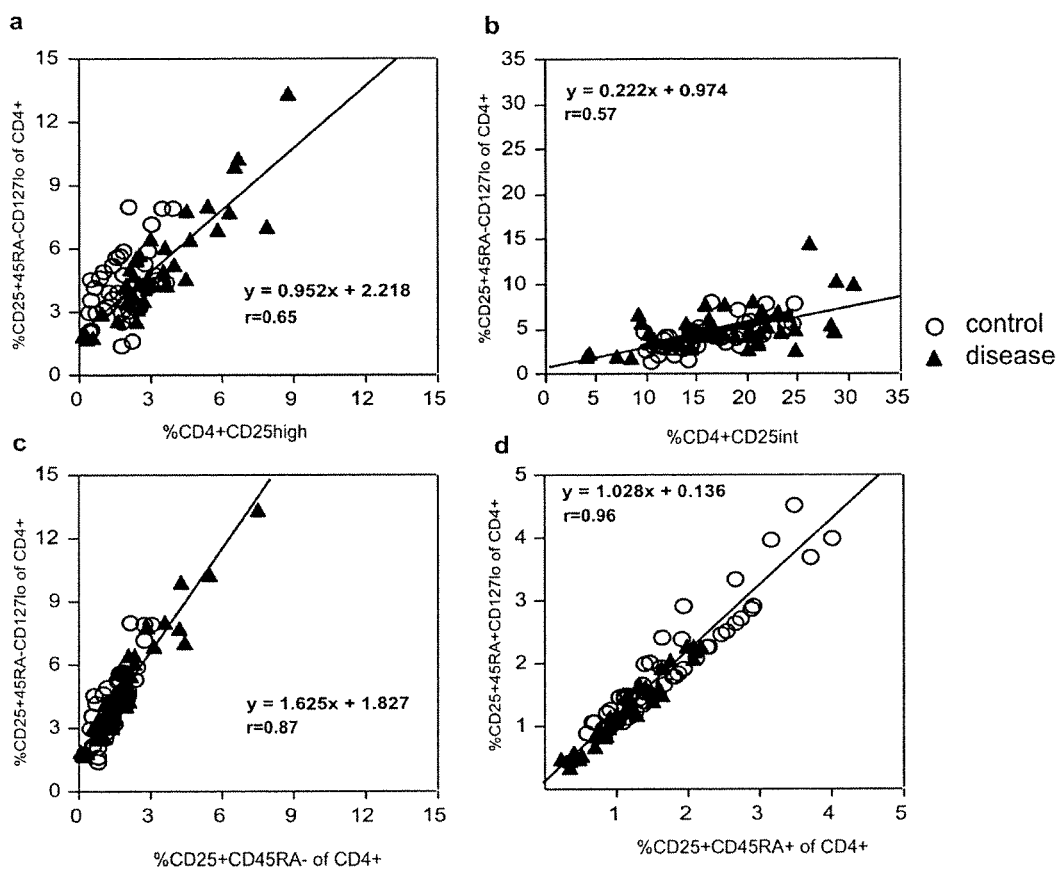
FIG. 8: Correlation of the different gating strategies for Tregs according to the gates shown in FIG. 7, using pooled data from 81 patients and controls. (a) gate A versus gate E. (b) gate B versus gate E. (c) gate C versus gate E. (d) gate D versus gate F. Linear regression equations are shown in each box. The significance of the correlation coefficients was estimated using a nonparametric Spearman test.

To illustrate the different estimates of Treg percentages for individual samples as a result of applying the gating strategies in FIG. 7, the inventors graphed the correlations between the various gates for the combined group of 81 patients and controls (FIG. 8). The best correlations (r>0.85) were between the data derived from the CD4/CD25/CD45RA strategy (gates C and D) and the new gates E and F, respectively. All gates except gate B underestimated the number of CD127$^{lo}$ Treg, due to exclusion of the Treg with the lowest expression of CD25, in an attempt to reduce contamination by conventional T cells. Gate B provided an overestimate because of contamination by CD127$^{hi}$CD25$^+$ T cells. Thus the data derived from the new strategy correlates with that from other gating strategies, although the numerical values are significantly different.

Example 9

Age-Related Changes in CD127$^{lo}$CD25$^+$ Treg in IBD Patients

Figure 9:
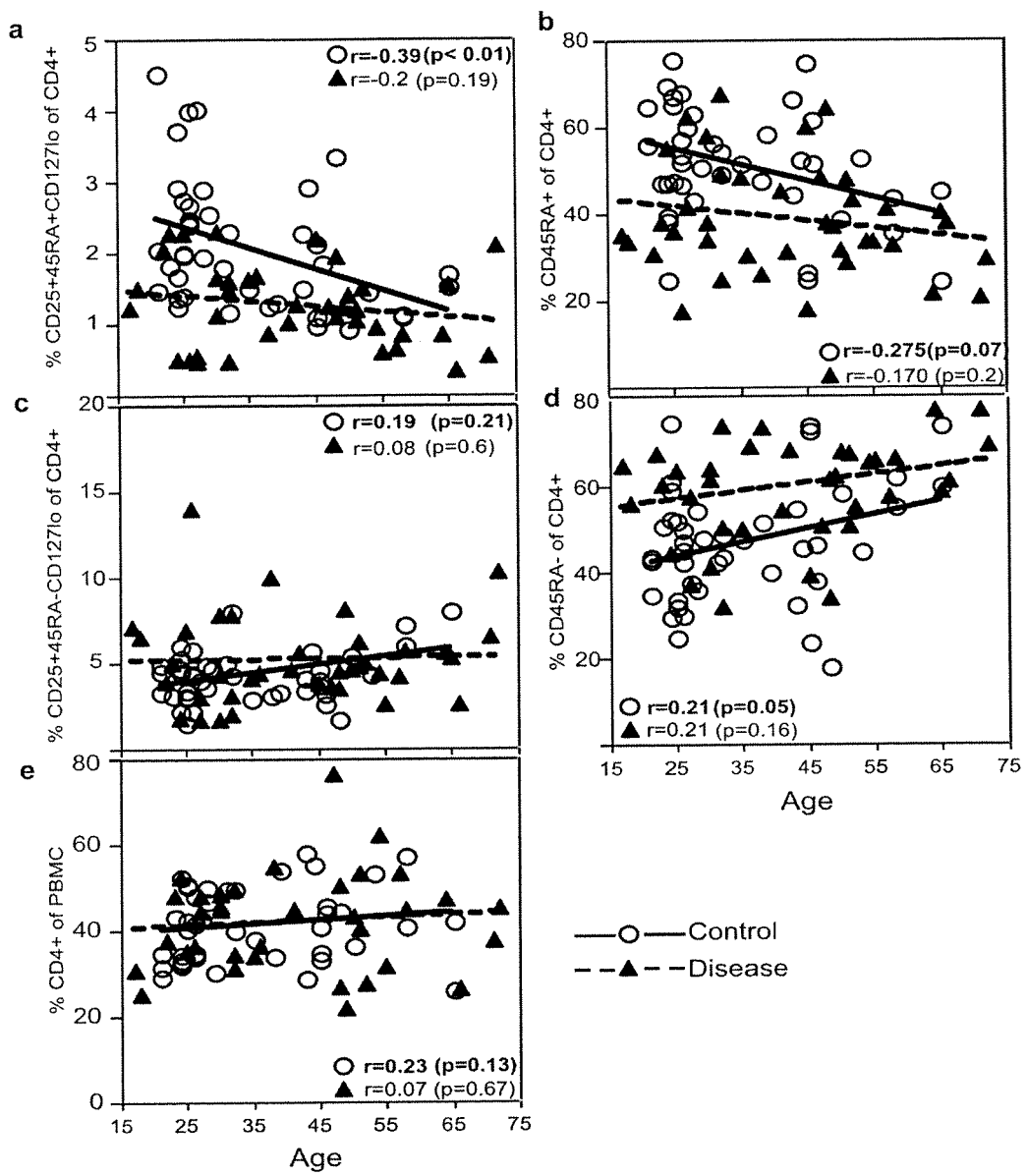
FIG. 9: Relationship between CD4$^+$ Treg and other subpopulations and age in control and IBD patients. Data are derived from the analysis presented in FIG. 7c. Linear regression was performed for control (N=43) and patient (N=38) groups. The significance of the correlation coefficients was estimated using a nonparametric Spearman test.

In contrast to previous reports asserting that the number of naïve Treg in peripheral blood declines as a function of age, the inventors have shown that naïve Treg percentages were essentially constant for IBD patients, so that the naïve Treg deficit in young patients was not apparent in the older patients (FIG. 9a). Part of the deficit in younger patients was due to a decrease in the percentage of CD4$^+$CD45RA$^+$ cells in patients compared to controls (FIG. 9b), whereas there was no difference in total percentages of CD4$^+$ cells (FIG. 9e).

In contrast to naïve Treg, the number of CD45RA$^-$ (RO$^+$) Treg was stable throughout adult life in both patients and controls (FIG. 9c). Because CD45RA$^-$ Treg comprise the majority of total Treg, numbers of total Treg were also stable throughout life. A reciprocal increase in CD4$^+$CD45RA$^-$ T cells was seen in patients compared to controls (FIG. 9d), reflective of a higher degree of overall immune activity in patients, and the percentage of CD45RA$^-$ T cells increased with age in both patients and controls.

FIG. 10 provides comparisons of Treg percentages in controls, CD and UC patients divided into 3 age cohorts, indicating that the deficit in naïve Treg reached statistical significance in CD patients between 15 and 45 years, and in UC patients between 15 and 30 years. In contrast, there was no significant difference in activated and total Treg numbers between patients and controls within any of the three cohorts.

Figure 11:
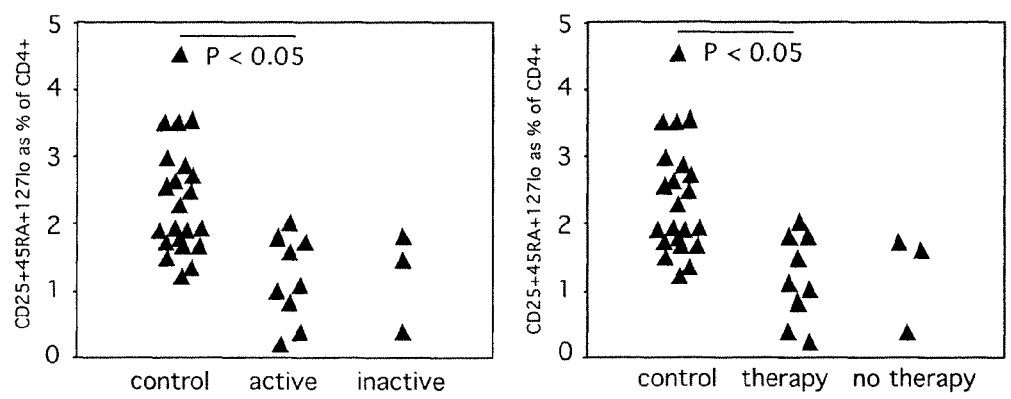
FIG. 11: No effect of disease activity or therapy on naïve Treg numbers in the 15-30y patient cohort. Data are derived from the experiment shown in FIG. 7. Patient samples were divided into those manifesting active versus inactive disease on the basis of macroscopic appearance at the time of colonoscopy or surgery, together with the histopathological examination. Therapy included treatments with corticosteroids, DNA analogues, aminosalicylates and/or antibiotics. Patients on "no therapy" were receiving no treatment at all.

As shown in FIG. 11, the deficit in naïve Treg was unrelated to disease activity, and was unaffected by therapy. Because it correlated with the young age peak of disease incidence, it may represent a primary abnormality that may predispose to development of disease.

Example 10

CD127$^{lo}$CD25$^+$Treg in Bowel Mucosa and Mesenteric Lymph Nodes of IBD Patients and Controls

In addition to studying blood, the inventors obtained mucosa and lymph nodes from freshly resected colonic specimens from patients with IBD or patients who had colons resected for diverticulosis or incontinence.

Figure 12:
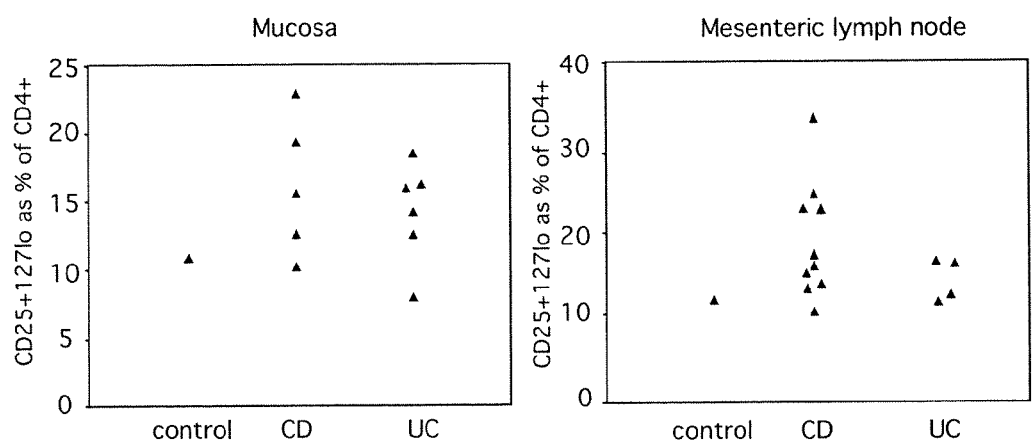
FIG. 12: No significant difference between the percentage of CD25+CD127lo Treg within CD4+ T cells in bowel mucosa and draining lymph nodes in CD and UC patients. The data indicate that the percentage of Treg in mucosa and lymph nodes is generally higher than in peripheral blood (compare with FIG. 4).

As shown in FIG. 12, no significant difference was observed between the percentage of CD25+CD127$^{lo}$ Treg within CD4$^+$ T cells in bowel mucosa and draining lymph nodes in CD and UC patients. The data indicate that the percentage of Treg in mucosa and lymph nodes is generally higher than in peripheral blood (as illustrated in FIG. 4).

Example 11

Comparison of Treg Number and Function in Cord Blood, Young Adult and Elderly Peripheral Blood

This study compared intracellular FoxP3 staining versus the CD4/CD25/CD127 combination to assess changes in the number of regulatory T cells from early infancy to late adulthood. The data, as shown in FIGS. 13-17, indicate that the pool of Treg cells is maintained within a narrow range throughout life, although the distribution between the CD45RA and CD45RO compartments shifts markedly. This shift parallels that of conventional T cells.

Peripheral blood from healthy adult donors (age-groups 20-25 and >60 years) was obtained by venous puncture and collected into Lithium-heparin tubes. Cord blood samples from healthy full-term neonates were acquired immediately after delivery from the clamped umbilical cord in the Nepean Hospital. Mononuclear cells were isolated by Ficoll-Hypaque (Amersham Pharmacia, Piscataway, N.J.) gradient centrifugation. The Ethics Committees of the Western Sydney Area Health Services approved the study.

Figure 13:
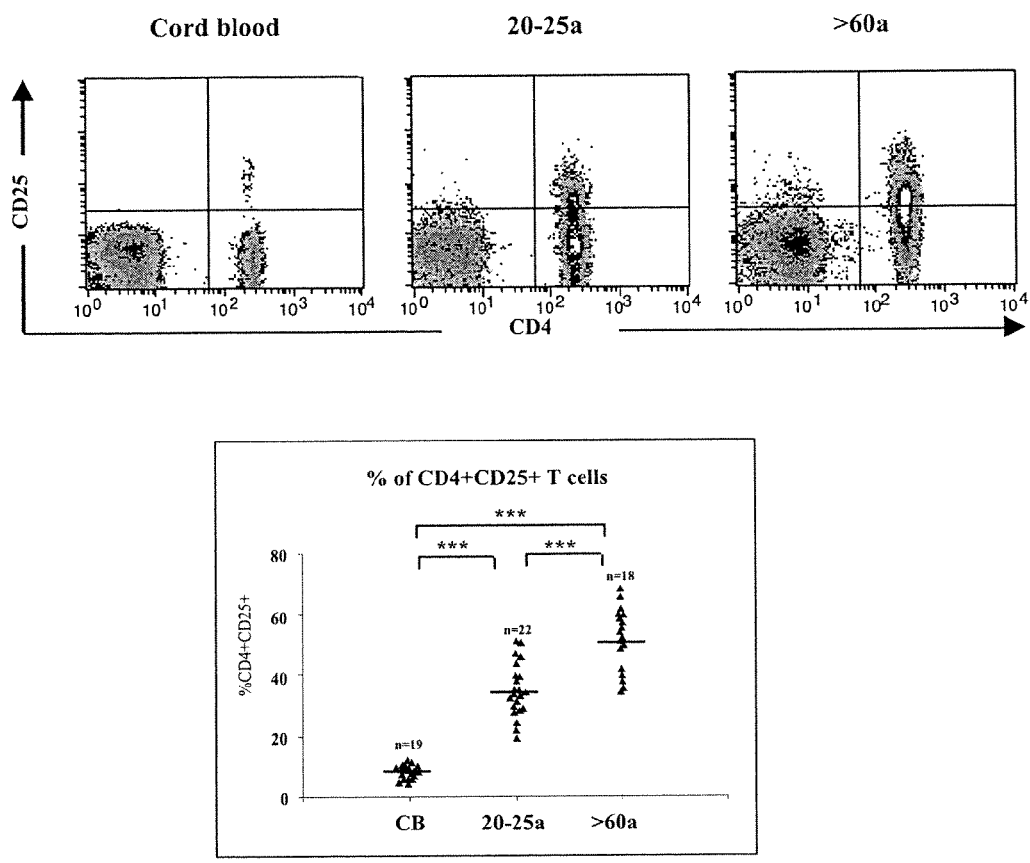
FIG. 13: Conventional gating strategy for distinguishing Treg in normal controls of different ages Upper panels: Example of staining with CD4 and CD25. Lower panel: increase in Treg numbers throughout life, as assessed using conventional CD4 and CD25 staining. *** $P<0.001$. CB=cord blood; 20-25a=controls between the ages of 20 and 25 years; >60a=controls over the age of 60 years.
Figure 14:
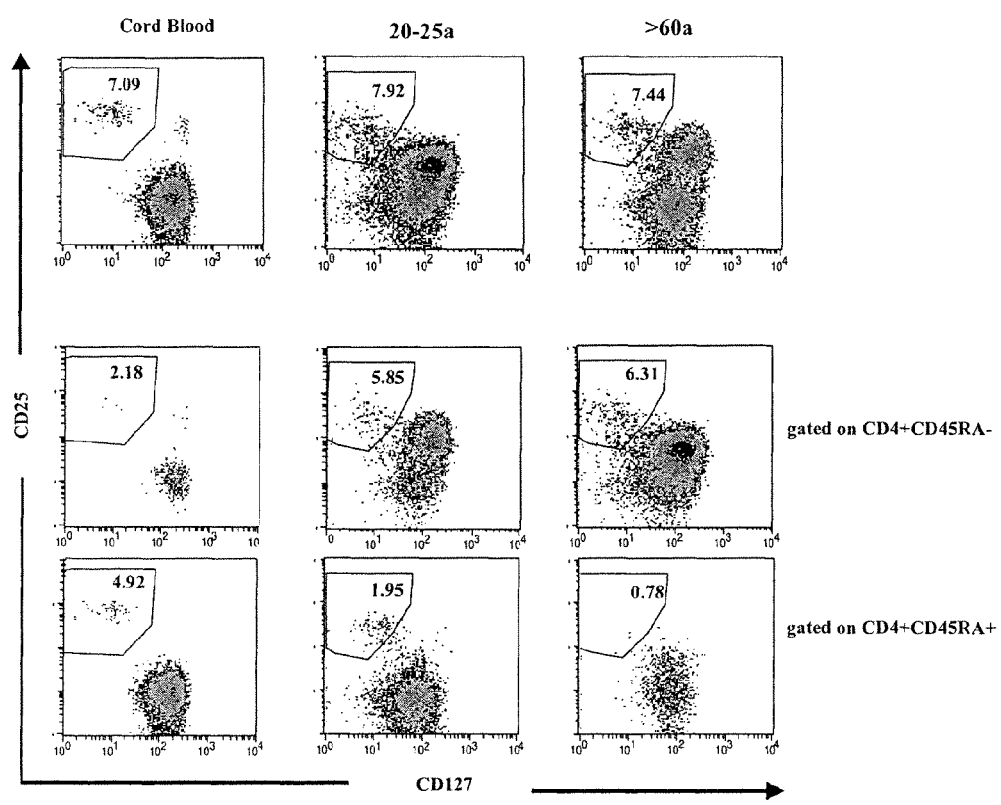
FIG. 14: Novel gating strategy for distinguishing Treg in normal controls of different ages, using staining with CD4, CD25, CD127 and CD45RA. Upper panels: gated on CD4+ cells. Lower panels: gated on CD4+CD45RA− or CD45RA+ cells.
Figure 15:
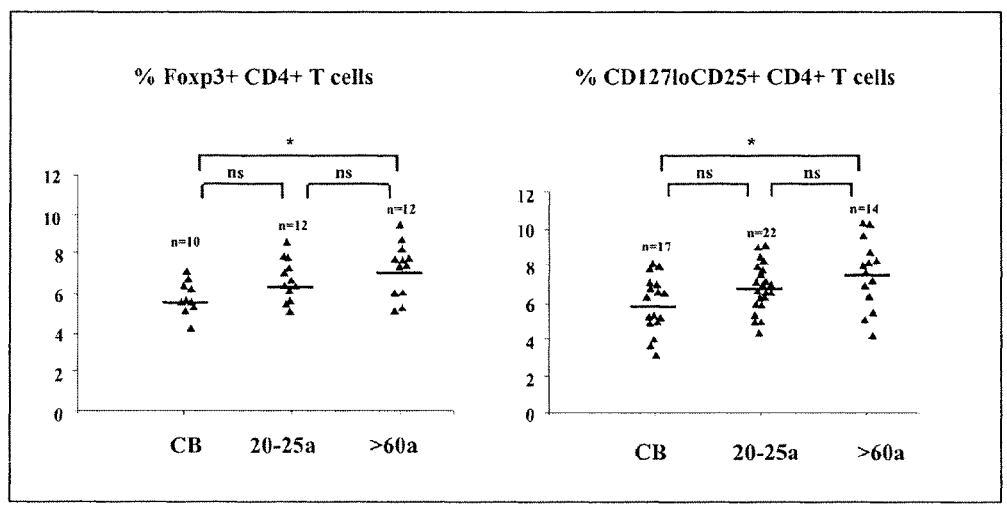
FIG. 15: Comparison of Treg numbers using gating for $CD25^+FoxP3^+$ cells compared with $CD25^+CD127^{lo}$ cells. Percentages of cells in cord blood and peripheral blood of adults in the 20-25 year and greater than 60 year age groups were calculated using the indicated gates. * $P<0.05$; ns, not statistically significant.
Figure 16:
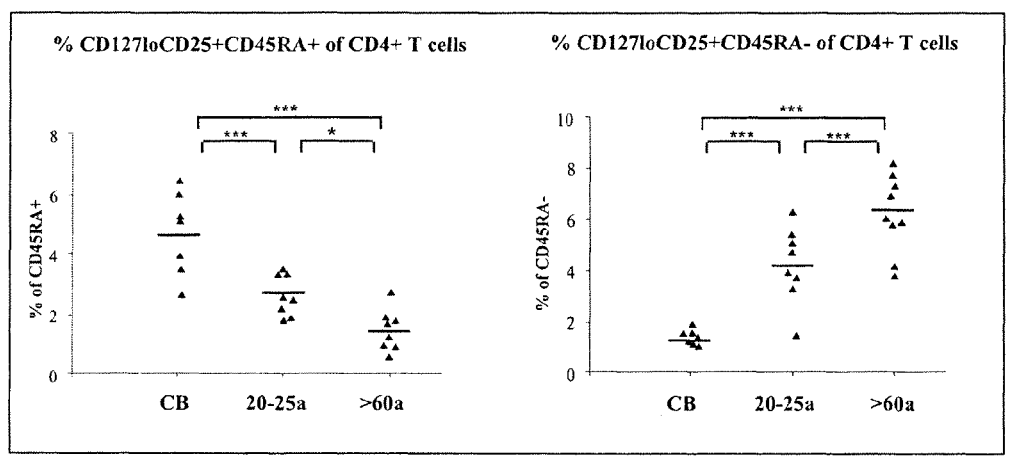
FIG. 16: Change in numbers of CD45RA+ and CD45RA− Treg numbers with age. Blood leukocyte samples were stained with antibodies to CD4, CD25 CD45RA and CD127, and gated as in FIG. 14, lower panels. A reciprocal decrease in CD45RA+ Treg and increase in CD45RA− Treg is apparent with age. *$P<0.001$, $P<0.01$, * $P<0.05$.

In FIG. 13, conventional gating for CD4$^+$CD25$^+$ cells was applied to samples of cord blood and peripheral blood from young (20-25 years) and old (>60 years) healthy donors. This analysis shows a significant increase in CD4$^+$CD25$^+$ Treg cells throughout life. Using the new marker combination, illustrated in FIG. 14 (upper panel), this increase was far less marked (FIG. 15, right panel) and was comparable to that seen with staining for CD4 and FoxP3 (FIG. 15, left panel). When CD45RA was included in the analysis, as illustrated in FIG. 14 lower panels, a reciprocal relationship between the number of CD45RA$^+$ and CD45RA$^-$ Tregs was apparent, with highly statistically significant differences in the numbers in the 3 age cohorts (FIG. 16).

Figure 17:
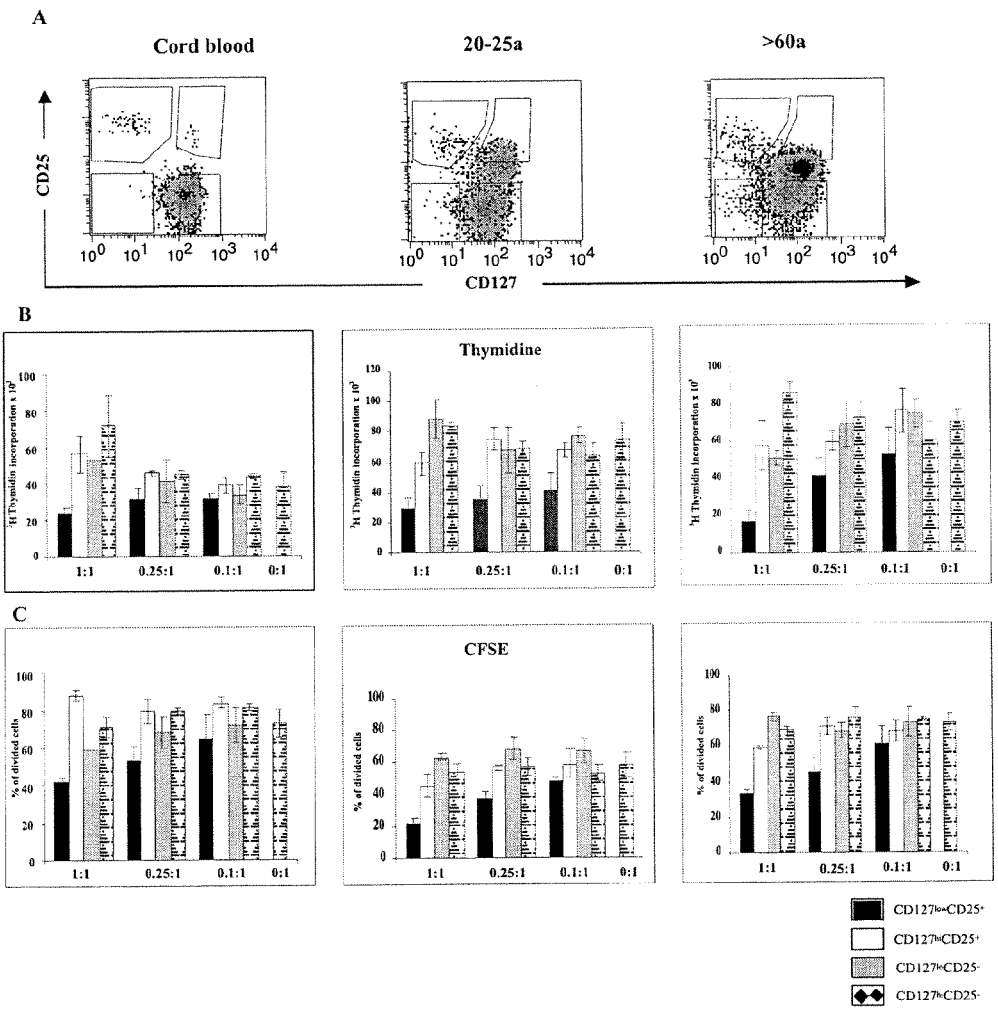
FIG. 17: Suppression is confined to CD4+CD25+CD127lo cells sorted from donors of all ages. A) Gating strategy for distinguishing Treg in normal controls of different ages, using staining with CD4, CD25 and CD127. B) Suppression by flow sorted populations from adult and cord blood. Responder cells were sorted autologous $CD4^+CD127^{hi}CD25^-$ cells. Ratios of suppressor to responder cells are shown below the figures. Cultures were pulsed with thymidine at 72 hrs and harvested 16 hrs later. Bars represent the mean+/−SEM counts per minute of 3-4 replicate cultures. C) Replicate cultures from the same sorted populations were set up using CFSE-labelled responder cells and the % proliferation was calculated relative to the mean number of divided cells in cultures containing only responder cells. Bars represent the mean+/−SEM counts per minute of 3-4 replicate cultures.

To test whether the suppressive function of Tregs changes throughout life, suppression assays were performed using cells sorted on the basis of staining with CD4/CD25 and CD127, as indicated in FIG. 17, upper panels. These assays indicated equivalent suppressive function for cells sorted from donors in each of the three age cohorts. Thus the shift from CD45RA expression to expression of a CD45RO$^+$RA$^-$ phenotype does not affect functional activity in vitro.

Example 12

Comparison of Circulating Treg Number in Healthy Elderly Versus Elderly Patients with Alzheimer's Disease

Peripheral blood Treg from 4 healthy individuals over the age of 75 years were compared with age-matched 5 individuals suffering from Alzheimer's disease. The study was performed at the Rush University Medical School with the approval of the Rush Institutional Review Board. Details of the study subjects are given in table 2.

TABLE 2

Subject Characteristics for Alzheimer's Disease Study

| ID | Sex | Age | Patient Group | % CD45RO$^-$CD127$^{lo}$ CD25$^+$ of CD4$^+$ | % CD45RO$^+$CD127$^{lo}$ CD25$^+$ of CD4$^+$ |
|---|---|---|---|---|---|
| 12 | M | 85 | NCI | 0.79 | 2.02 |
| 15 | F | 84 | NCI | 2.22 | 4.49 |
| 18 | F | 90 | NCI | 1.83 | 1.08 |
| 21 | M | 75 | NCI | 0.21 | 3.03 |
| 14 | M | 90 | AD | 1.27 | 5.03 |
| 16 | M | 93 | AD | 0.34 | 5.31 |
| 17 | F | 91 | AD | 0.76 | 2.01 |
| 19 | F | 92 | AD | 2.27 | 3.99 |
| 20 | M | 83 | AD | 0.63 | 1.00 |

NCI = No Cognitive Impairment
AD = Alzheimer's Disease

Figure 18:
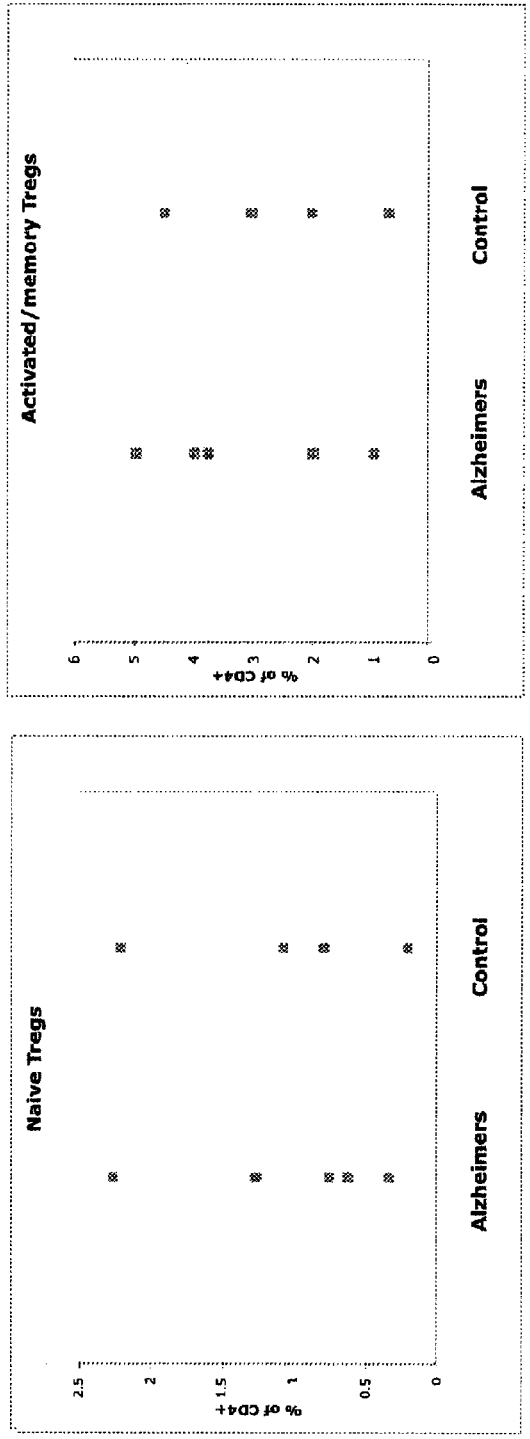
FIG. 18: Comparison of circulating Treg number in patients with Alzheimers disease versus healthy aged controls. Blood leukocyte samples were stained with antibodies to CD4, CD25 CD45RA and CD127, and gated as in FIG. 14 lower panels. The 4 control patients were between 75 and 90 years of age and had normal cognitive function. The 5 patients with Alzheimers disease were aged between 83 and 92 years of age. Naïve Tregs were gated on $CD4^+CD25^+CD127^{lo}CD45RO^-$, and activated/memory Tregs were gated as $CD4^+CD25^+CD127^{lo}CD45RO^+$. No significant difference was seen between the two groups.

As shown in FIG. 18, the number of T cells within the naïve Treg (CD4$^+$CD45RO$^-$ CD127$^{lo}$CD25$^+$) and activated/memory Treg (CD4$^+$CD45RO$^+$CD127$^{lo}$CD25$^+$) compartments in individuals over the age of 75 years was highly variable. No difference was seen between the 2 subject groups.

Example 13

Increase in Circulating Treg Number in Patients with Severe Atopic Eczema Versus Healthy Controls

Figure 19:
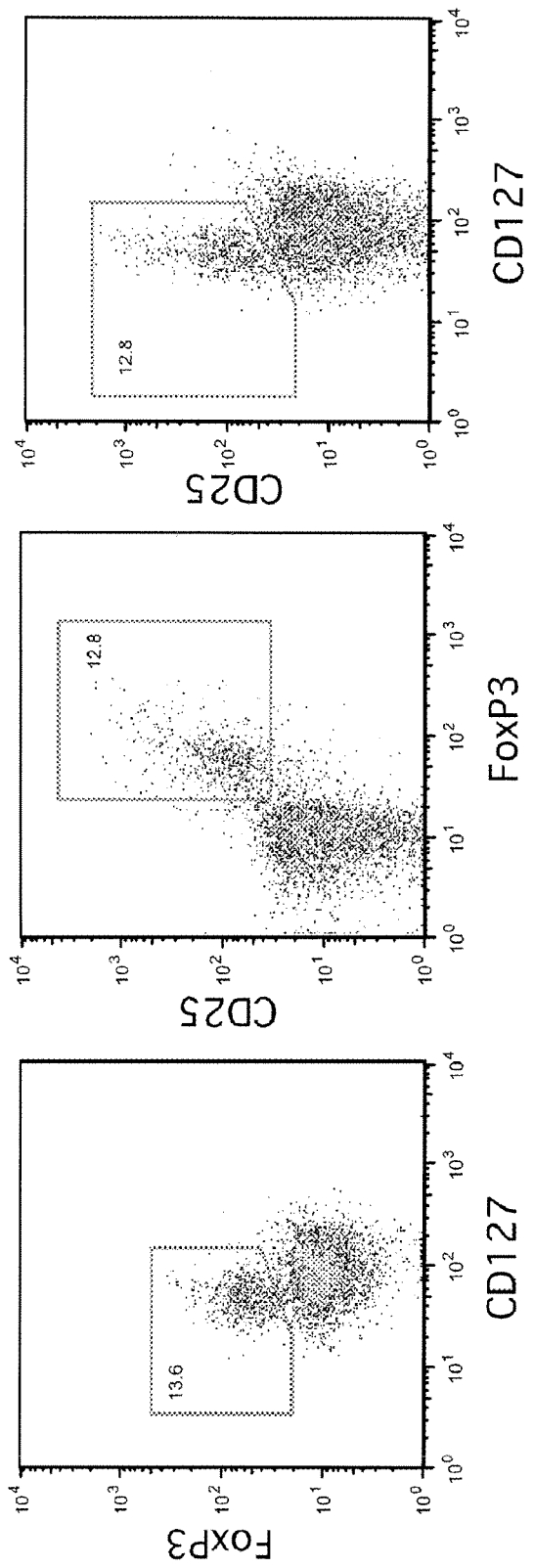
FIG. 19: Example of gating of Treg in PBL from an eczema patient, stained with CD4, CD25, CD127 and FoxP3. Dot plots are gated for CD4+ cells. The pattern of expression of FoxP3 and CD127 is similar to that in controls (for example, in FIG. 3). Thus, FoxP3+ cells are CD25+ and correspond to the $CD127^{lo}$ CD25+ population.
Figure 20:
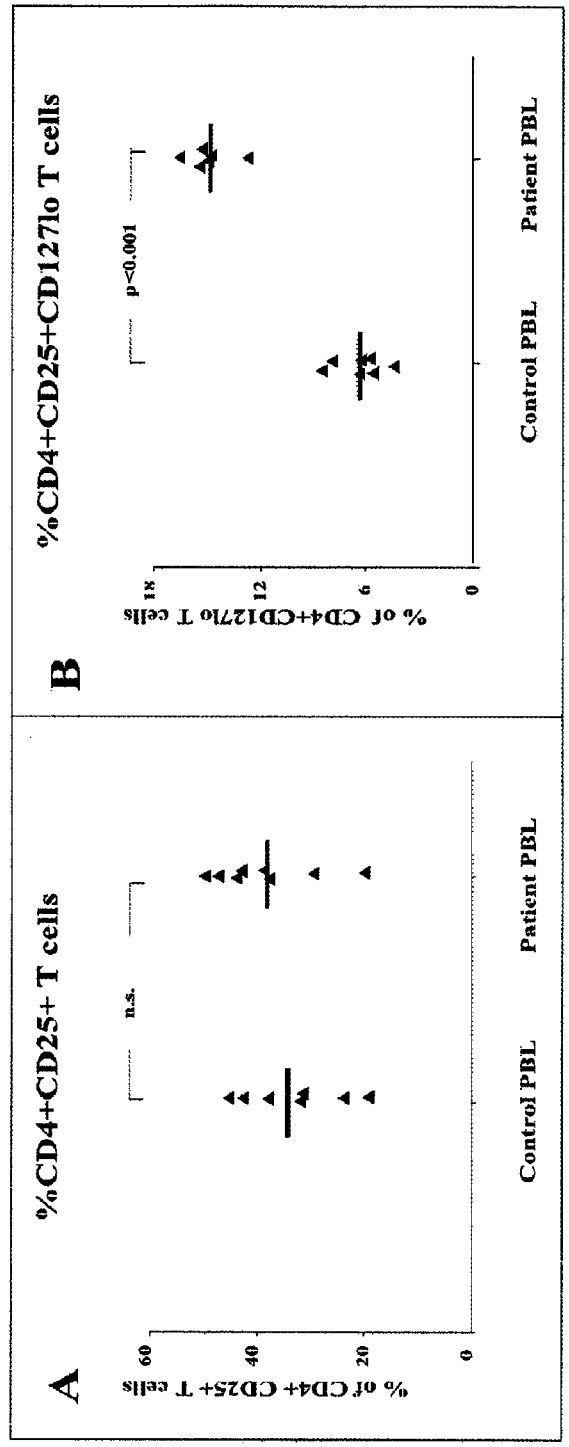
FIG. 20: Comparison of Treg numbers between eczema patients and healthy controls, using different gating strategies. (A) Conventional CD4+ CD25+ gate. The difference is not statistically significant. (B) $CD4^+CD25^+CD127^{lo}$ gate, as illustrated in FIG. 19. The results in (B) were confirmed using FoxP3 staining. The eczema patients have significantly more Treg than age-matched controls ($P<0.001$).

Peripheral blood from patients with severe atopic eczema attending the Westmead hospital, with a mean IgE level of 20,000 I.U., were stained with CD4/CD25/CD127/FoxP3. Comparison of staining with CD127 versus FoxP3 for one of the patients is shown in FIG. 19. As for healthy controls, there was a clear correlation between FoxP3 expression and the CD127$^{lo}$CD25$^+$ phenotype. FIG. 20 shows a comparison of the Treg numbers derived from conventional gating of CD4+ CD25+ cells versus CD4+CD25+CD127$^{lo}$ gating. While the former shows no difference between the healthy subjects and eczema patients, the new gating shows a highly significant increase in Treg cells in eczema patients.

Example 14

Comparison of Circulating Treg Number in Atopic Patients with Asthma Versus Healthy Controls Peripheral blood samples were obtained from individuals as shown in Table 3:

TABLE 3

Subject numbers for peripheral blood samples

|  | SPT− | SPT+ A− | SPT+ A+ |
|---|---|---|---|
| n | 7 | 31 | 24 |
| M/F | 0/7 | 16/15 | 8/16 |
| Age | 25-57 | 14-52 | 14-50 |

Figure 21:
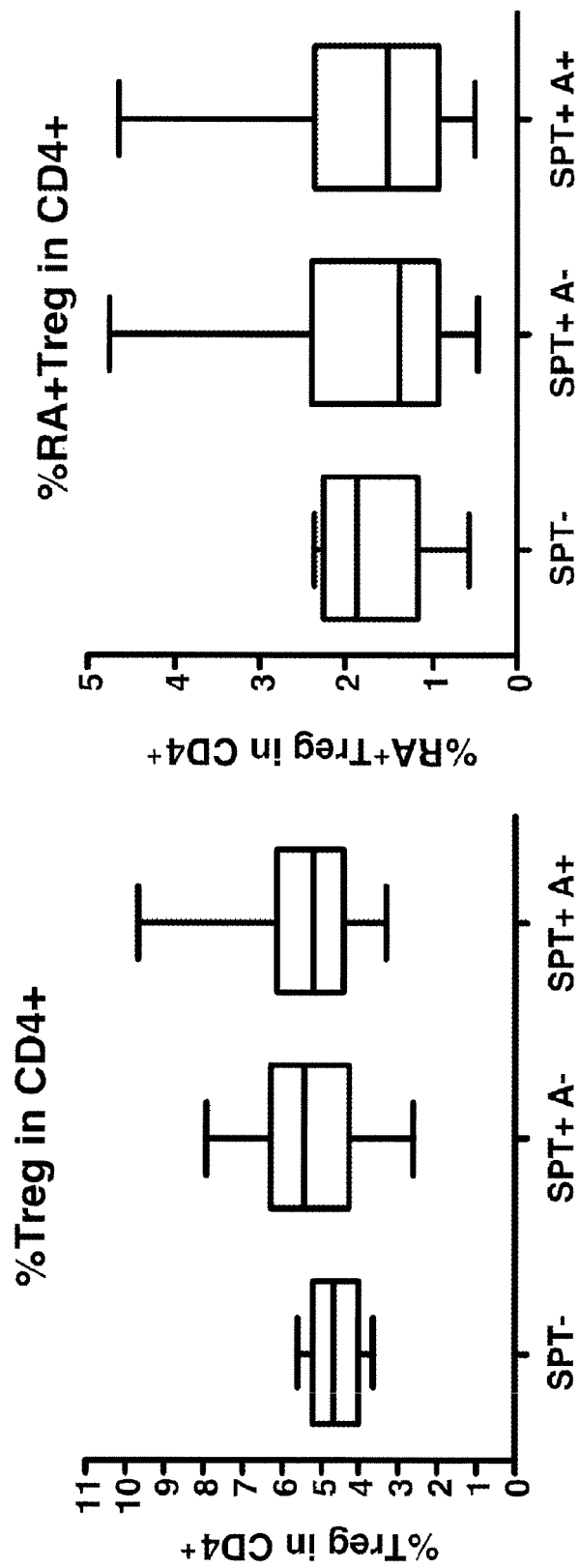
FIG. 21: Frequency of total Tregs ($CD4^+CD25^+CD127^{lo}$) and naïve Tregs ($CD4^+CD45RA^{+CD}25^+CD127^{lo}$) in the blood of non-atopic subjects, atopic subjects without asthma, and atopic subjects with asthma. Data are displayed as boxplots (between 25% and 75%) with median and range. There was no significant difference between the 3 groups.

SPT− Skin Prick Test Negative to all allergens tested
SPT+ Skin Prick Test Post (>3 mm wheal size) to any allergen tested
A− Non-asthmatic
A+ Doctor-diagnosed asthma As shown in FIG. 21, there was no significant difference in the percentage of total Treg (CD4+CD25+CD127$^{lo}$) or in the percentage of naïve CD4+CD25+CD127$^{lo}$ CD45RA+ treg in the three subject groups.

A further comparison was performed on patients derived from the cohort in FIG. 21 (ie the non-atopic control group is the same in both sets of data). Data relating to the amount of IL5 produced upon 48 hours of in vitro culture with house dust mite (HDM) was available for a subset of atopics (5 asthmatics in the IL5− group and 4 asthmatics in the IL5+ group), as shown in Table 4.

TABLE 4

Subject numbers for IL-5/HDM peripheral blood samples

|  | SPT− | SPT+HDM IL5− | SPT+HDM IL5+ |
|---|---|---|---|
| n | 7 | 17 | 9 |
| M/F | 0/7 | 7/10 | 2/7 |
| Age | 25-57 | 20-52 | 14-24 |

Figure 22:
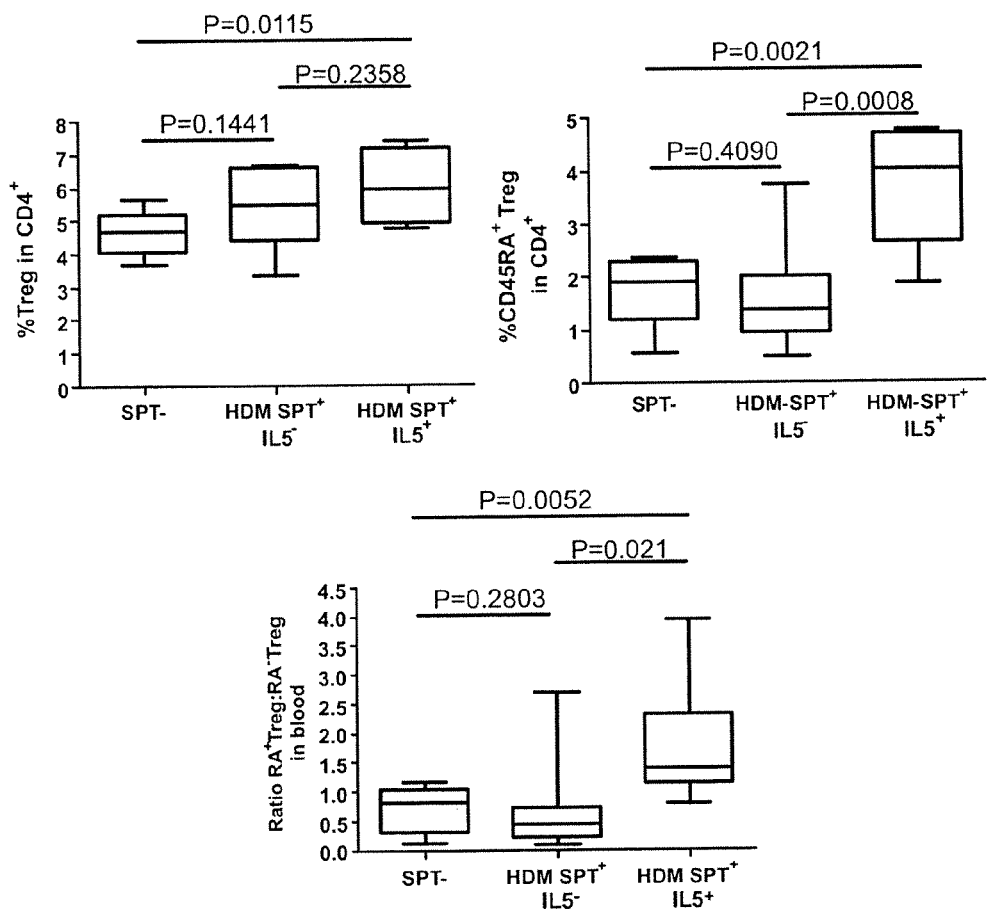
FIG. 22: Frequency of Tregs in the blood of non-atopic subjects (skin prick test negative (SPT-ve)) and atopic subjects split according to their IL5 response to house dust mite (HDM) in culture. Upper panels: Total Tregs ($CD4^+CD25^+CD127^{lo}$) and CD45RA+ Tregs ($CD4^+CD45RA^+CD25^+CD127^{lo}$). Lower panel: ratio of naïve CD45RA+ Tregs to activated/memory CD45RA− Tregs. Both the percentage of naïve Tregs and the ratio of naïve to effector/memory Tregs were significantly increased as a proportion of CD4+ T cells in patients making detectable IL-5 in response to HDM in culture whereas there was no overall increase in total Treg cells in this group.

SPT− Skin Prick Test Negative to all allergens tested
SPT+ Skin Prick Test Post (>3 mm wheal size) to house dust mite (HDM)
HDM IL5− Undetectable IL5 levels in PBMC culture after 48 hr stimulation with HDM
HDM IL5+ Detectable IL5 levels in PBMC culture after 48 hr stimulation with HDM As shown in FIG. 22, subdividing the asthmatic group into those that secreted detectable IL-5 after exposure to HDM in culture, and those that did not, resulted in no significant difference in the percentage of total Treg (CD4+CD25+ CD127$^{lo}$) between the 3 groups. However, both the naïve CD25+CD127$^{lo}$CD45RA+ Treg as a percentage of CD4+ T cells, and the ratio of CD25+CD127$^{lo}$CD45RA+ to CD25+ CD127$^{lo}$CD45RA− Treg were significantly increased in the IL5+ group compared to the 2 other groups. Thus HDM-reactive asthmatic patients show a significant increase in circulating naïve Treg cells, and an increase in the ratio of naïve to activated/memory Tregs in peripheral blood.

Example 15

Figure 23:
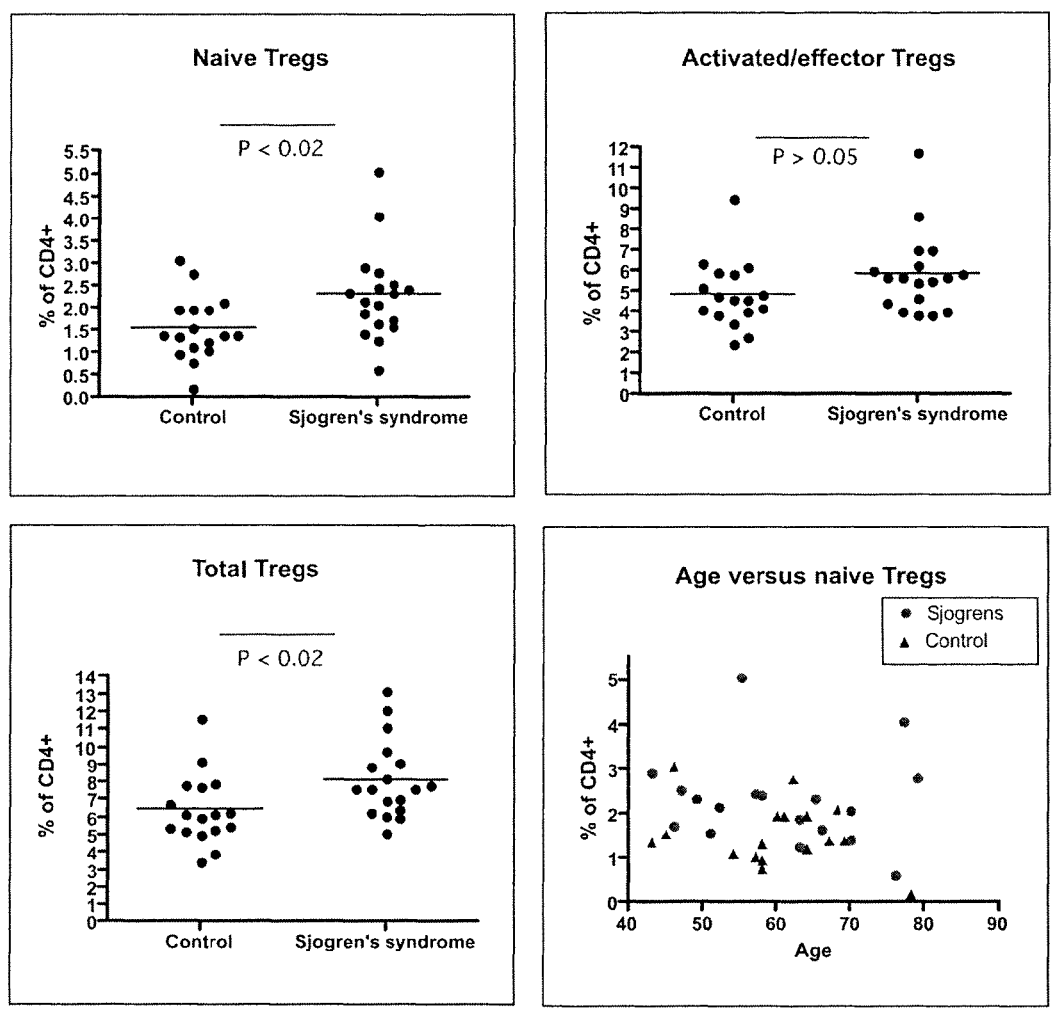
FIG. 23: Frequency of naïve, activated and total Tregs in the blood of patients with primary Sjogrens syndrome. Blood leukocyte samples were stained with antibodies to CD4, CD25, CD45RA and CD127, and gated as in FIG. 14 lower panels. Controls were age and sex matched. There was a significant increase in both naïve and total Tregs as a percentage of CD4+ T cells in the patient group, compared with age matched controls.

Comparison of Circulating Treg Number in Patients with Sjogren's Syndrome Versus Healthy Controls Peripheral blood from 18 primary Sjogrens syndrome patients (all female) and 17 age matched female healthy controls were stained with the CD4/CD25/CD127/CD45RA mAb combination. Primary Sjogrens syndrome was diagnosed according to the European criteria (29). As shown in FIG. 23, the percentages of naïve and total (but not activated) Treg cells were higher in Sjogrens syndrome patients. The increase was seen over the entire age distribution.

Example 16

Comparison of Circulating Treg Number in Patients at Different Stages of HIV Infection Peripheral blood was obtained from 28 HIV+ patients with advanced disease (Rush University Medical Center, Chicago, Ill.), 10 patients with primary infection (seroconverters, St Vincents Hospital, Darlinghurst, NSW, Australia) and 7 HIV+ patients who developed immune reconstitution disease (IRD) (St Vincent Hospital). All patients, except those with primary infection and 3 out of 28 with late stage disease, were under therapy with anti-retroviral agents. The study was carried out with the approval of the Central Area Health Services and the Rush Institutional Review Board.

Figure 24:
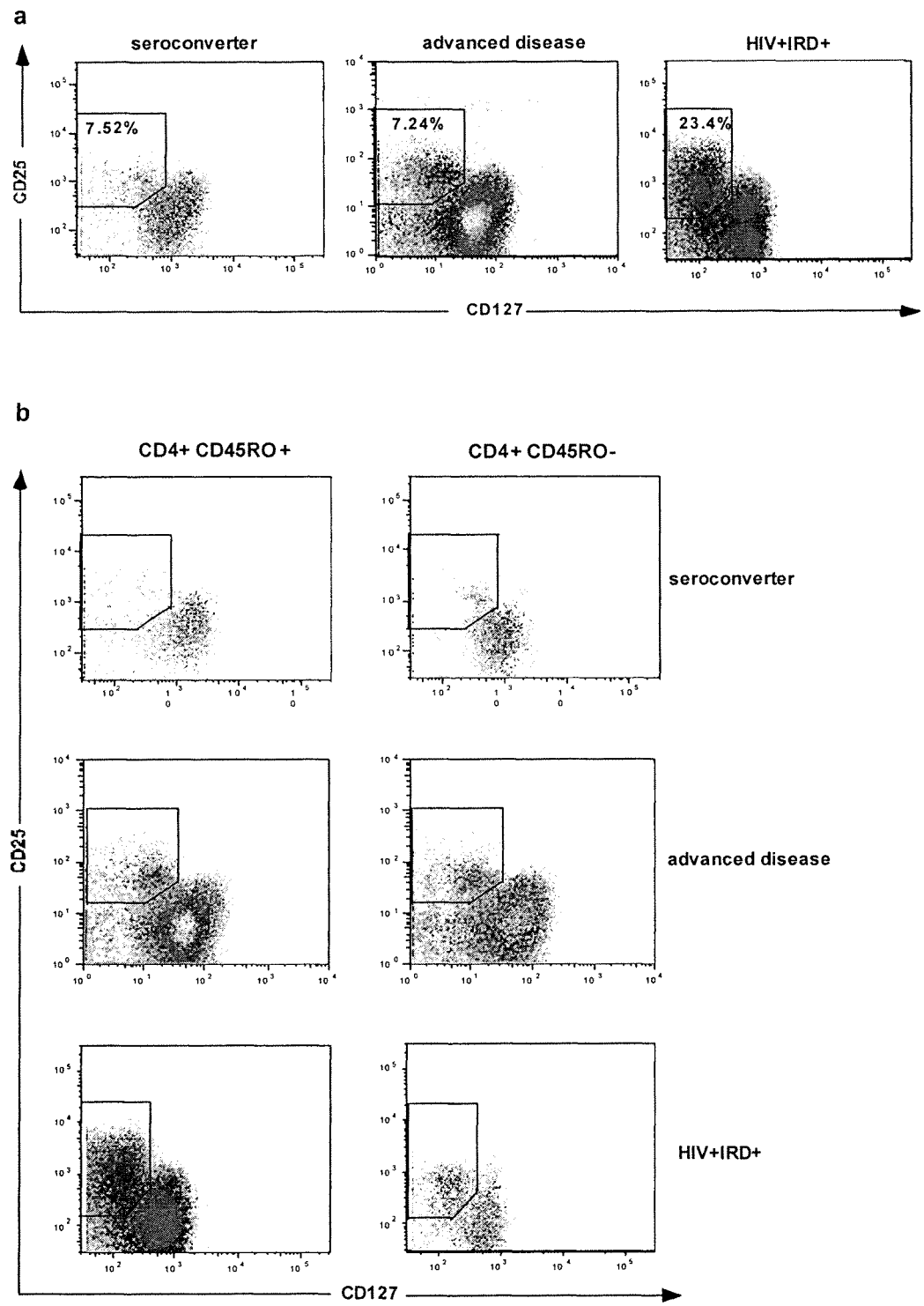
FIG. 24: An example of expression of CD127 in 3 different groups of patients with HIV. (a) Plots are gated for CD4+ CD8− T cells. $CD25^+CD127^{lo}$ cells are boxed and the % of cells in the box is shown. (b) Plots are gated for CD4+CD8− CD45RO+ or RO− T cells. $CD25^+CD127^{lo}$ cells are boxed. IRD=immune reconstitution disease.

Representative flow profiles are shown in FIG. 24. The pattern of CD25 and CD127 expression within CD4+ T cells was not altered in patients with HIV, apart from those with IRD, where there was a massive increase in CD25+CD127$^{low}$ cells. Subdivision on the basis of CD45RO expression indicated that the Treg increase in IRD patients was principally within the CD45RO+ subset of CD4+ T cells.

Figure 25:
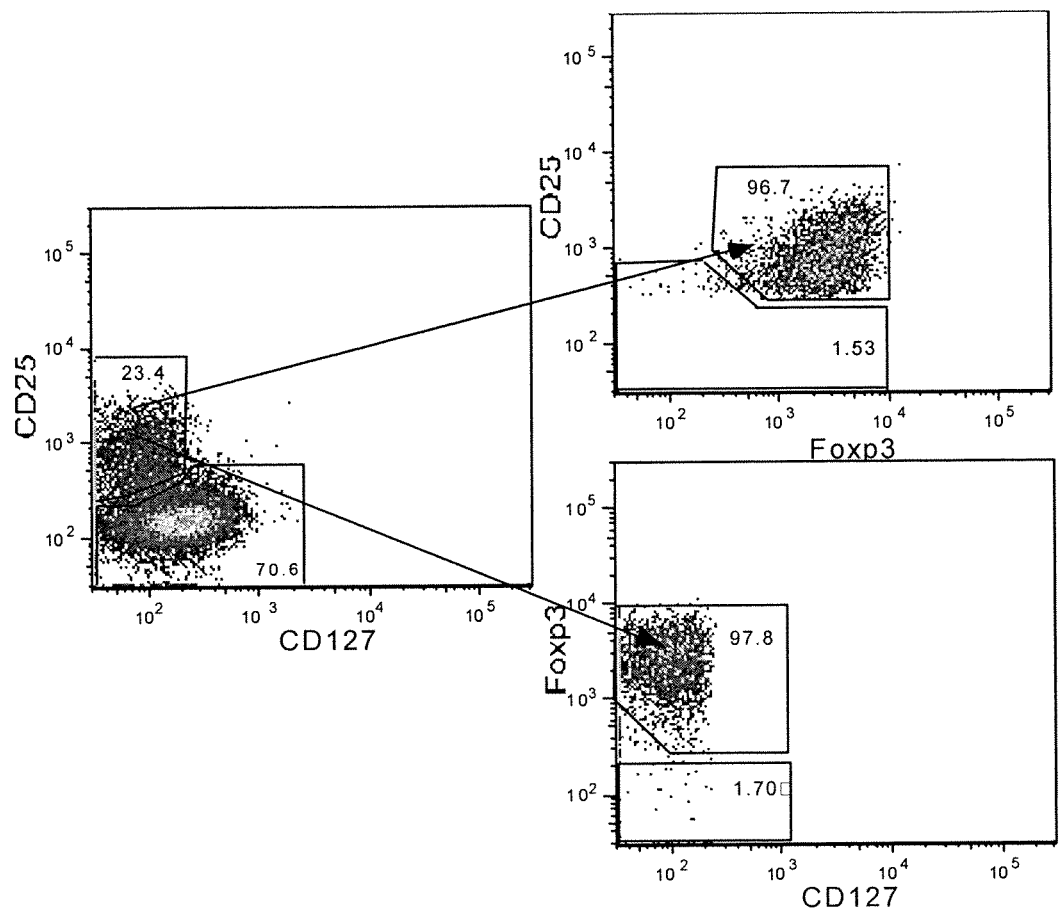
FIG. 25: Correlation between expression of FoxP3 and $CD127^{lo}$ phenotype in an HIV+ patient with IRD. PBMCs from a HIV+IRD+ patient were gated for CD3+CD4+ cells. $CD25^+CD127^{lo}$ cells are boxed and correlation between the percentages of $CD25^+Foxp3^+$ and $CD127^{lo}FoxP3^+$ cells within the same gate are shown.

To measure expression of Foxp3 within the CD25+ CD127$^{lo}$ population, cells from a patient with IRD were stained with a combination of monoclonal antibodies to CD4, CD25, Foxp3 and CD127. 96.7% and 97.8% of CD4+ CD127$^{low}$CD25+ cells (FIG. 25, left panel) fell within the CD25+Foxp3+ gate and 97.8% of CD4+CD127$^{lo}$Foxp3+ gate respectively (FIG. 25, right panels). Thus there was a high rate of concordance between the CD127$^{lo}$ phenotype and expression of Foxp3 protein within CD4+CD25+ cells.

Figure 26:
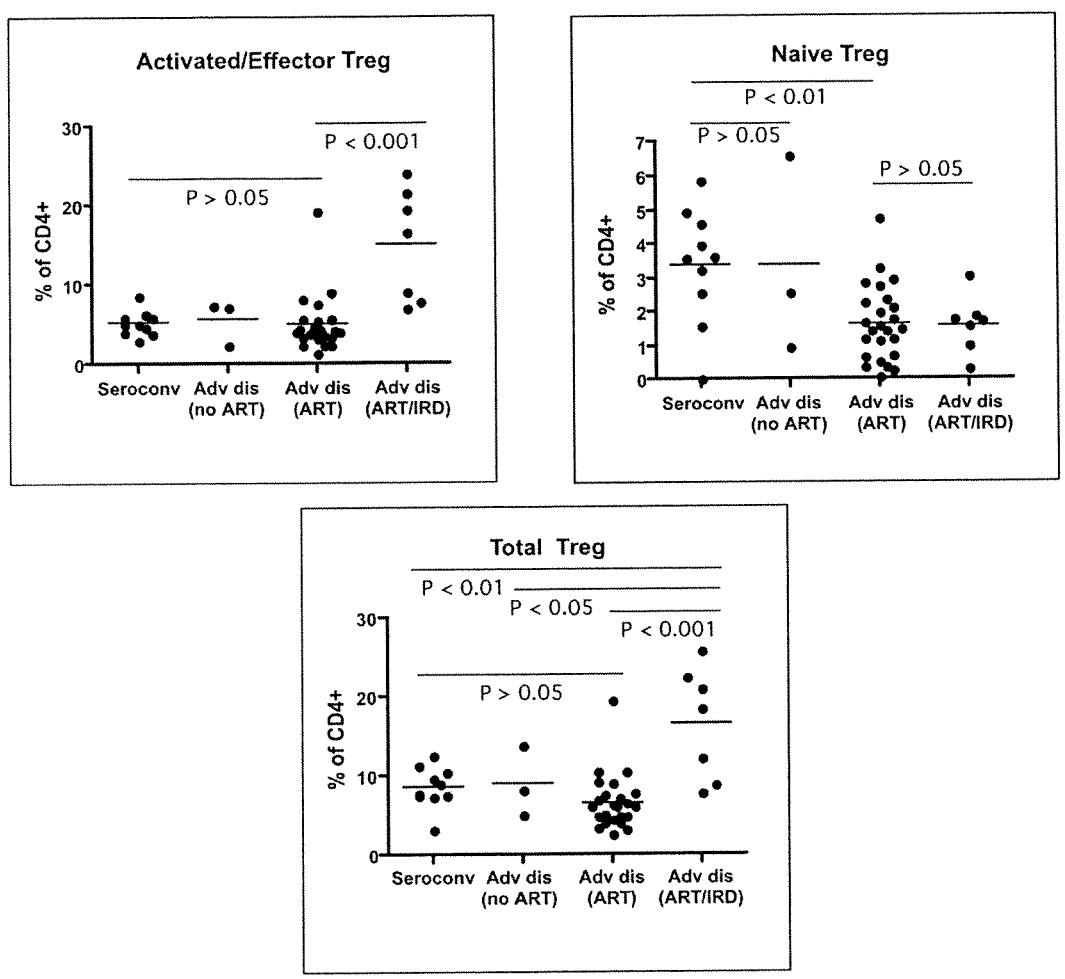
FIG. 26: Treg numbers in HIV+ patients, divided into seroconverters, patients with advanced disease (+/−anti-retroviral therapy), and patients with advanced disease, anti-retroviral therapy and immune reconstitution disease. The mean number of total Tregs in seroconverters was 8.68+/−0.83% (mean+/−SEM), in patients with advance disease with or without therapy was 6.68+/−0.68 and 8.78+/−2.3% respectively and in patients with IRD was 16.64+/−2.66%. IRD patients had a significantly higher percentage of CD45RO+ Treg and total Treg cells whereas the number of naive Tregs was significantly increased in seroconverters compared with chronic HIV treated with ART.

As shown in FIG. 26, CD45RO+ Treg were significantly increased in HIV+ patients with IRD. Compared to seroconverters, chronic HIV patients generally had fewer naïve Treg and the difference reached statistical significance in the group with advanced disease being treated with ART.

Example 17

Measurement of Circulating Treg Number in Patients with Melanoma

In studies conducted at the Ludwig Institute for Cancer Research at the Austin Hospital in Melbourne, Treg were enumerated in peripheral blood from patients with melanoma. The 6 patients shown in Table 5 were not enrolled on a vaccine trial but were bled 3 times per week over a number of weeks, to assess day-to-day fluctuations in Treg numbers within an individual.

TABLE 5

Figure 27:
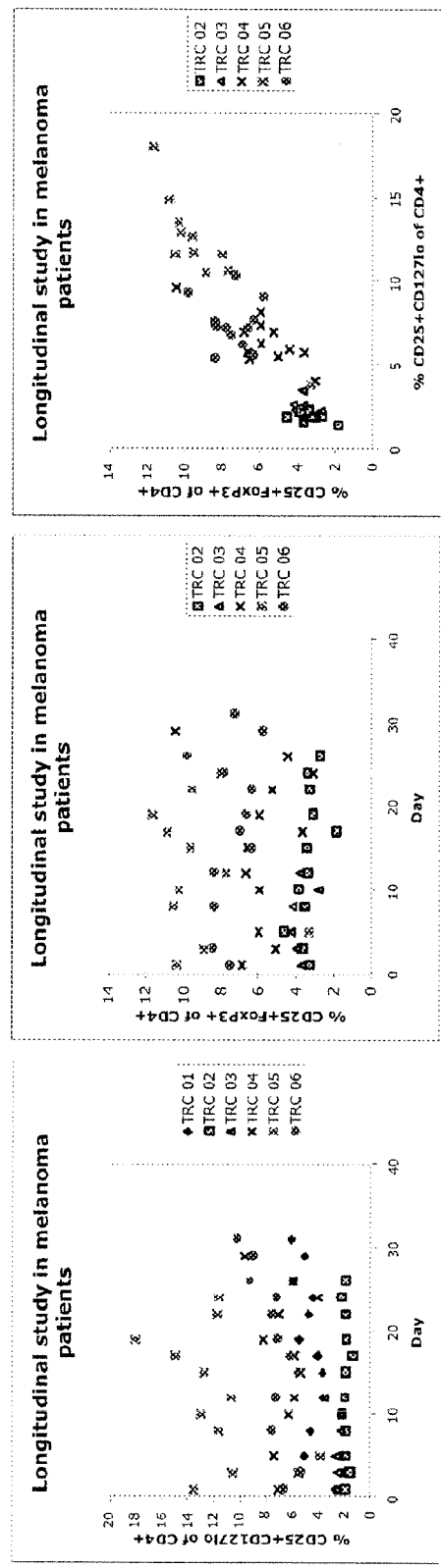
FIG. 27: Longitudinal study of Treg numbers in melanoma patients, comparing CD127/CD25/CD4 staining with FoxP3/CD25/CD4 staining for thrice weekly bleeds. The number of Tregs was generally stable using either technique, with a good correlation between the two methods (right hand panel).

Patient information for data shown in FIG. 27

| Patient | Sex | Age |
|---|---|---|
| TRC 01 | M | 82 |
| TRC 02 | F | 33 |
| TRC 03 | M | 70 |
| TRC 04 | F | 67 |

TABLE 5-continued

Patient information for data shown in FIG. 27

| Patient | Sex | Age |
|---|---|---|
| TRC 05 | M | 49 |
| TRC 06 | M | 77 |

As shown in FIG. 27, there was a good correlation between the Treg numbers derived from staining with CD4/CD127/CD25 and those from CD4/FoxP3 analysis (right panel). Treg numbers were generally stable over periods of more than a month, with patients with generally higher Treg numbers showing more longitudinal variation (left and centre panels).

The patients shown in Table 6 were enrolled in the LUD2002-013 trial (vaccination with NY-ESO-1+ISCOMA-TRIX). All 12 patients had advanced metastatic melanoma.

TABLE 6

Figure 28:
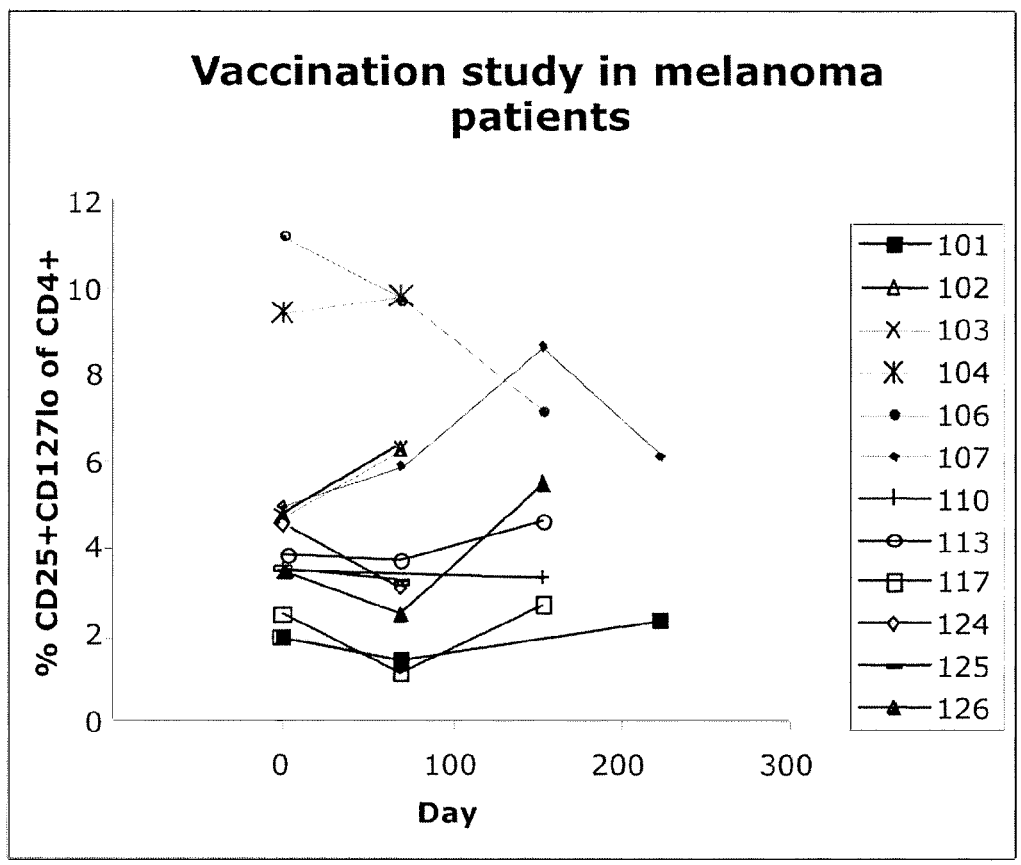
FIG. 28: Vaccination study in melanoma patients. Patients were bled before the first vaccination and then after each subsequent vaccination. There were no significant changes in Treg numbers with vaccination.

Patient information for data shown in FIG. 28

| Patient | Sex | Age |
|---|---|---|
| 101 | M | 59 |
| 102 | F | 62 |
| 103 | F | 53 |
| 104 | F | 79 |
| 106 | M | 46 |
| 107 | M | 86 |
| 110 | M | 64 |
| 113 | M | 49 |
| 117 | M | 72 |
| 124 | M | 67 |
| 125 | M | 41 |
| 126 | F | 67 |

As shown in FIG. 28, the variation in Treg numbers after vaccination was no more than was apparent in the longitudinal study shown in FIG. 27. The variation was essentially random, with the values rising in some patients (eg 107) and falling in others (eg 106)

Example 18

Measurement of Circulating Treg Number in Renal Transplant Patients Versus Those in Chronic Renal Failure, with or without Dialysis A group of 60 patients with chronic renal failure (CRF) was enrolled at the Prince of Wales Hospital, Sydney. Details of the patients are given in Table 7.

TABLE 7

Patients in renal disease study of Tregs in peripheral blood

| Patient ID | Age | Sex | Group |
|---|---|---|---|
| 3 | 26 | Male | CRF |
| 43 | 35 | Female | CRF |
| 8 | 37 | Female | CRF |
| 31 | 49 | Female | CRF |
| 30 | 56 | Male | CRF |
| 13 | 60 | Male | CRF |
| 14 | 65 | Female | CRF |
| 39 | 66 | Male | CRF |
| 27 | 69 | Male | CRF |
| 37 | 70 | Male | CRF |
| 7 | 75 | Male | CRF |
| 41 | 75 | Male | CRF |
| 10 | 77 | Female | CRF |
| 28 | 77 | Female | CRF |
| 11 | 77 | Male | CRF |
| 26 | 77 | Male | CRF |
| 29 | 77 | Male | CRF |
| 16 | 82 | Male | CRF |
| 20 | 82 | Male | CRF |
| 51 | 90 | Male | CRF |
| 45 | 22 | Female | Dialysis |
| 55 | 23 | Female | Dialysis |
| 42 | 42 | Male | Dialysis |
| 59 | 44 | Female | Dialysis |
| 18 | 44 | Male | Dialysis |
| 53 | 44 | Male | Dialysis |
| 24 | 52 | Female | Dialysis |
| 36 | 52 | Female | Dialysis |
| 23 | 58 | Female | Dialysis |
| 48 | 58 | Female | Dialysis |
| 47 | 60 | Female | Dialysis |
| 52 | 64 | Male | Dialysis |
| 54 | 64 | Male | Dialysis |
| 32 | 72 | Female | Dialysis |
| 19 | 72 | Male | Dialysis |
| 50 | 76 | Male | Dialysis |
| 25 | 77 | Female | Dialysis |
| 22 | 80 | Female | Dialysis |
| 21 | 80 | Male | Dialysis |
| 46 | 81 | Female | Dialysis |
| 15 | 24 | Male | Transplant |
| 60 | 33 | Female | Transplant |
| 34 | 38 | Female | Transplant |
| 57 | 43 | Female | Transplant |
| 49 | 43 | Male | Transplant |
| 44 | 48 | Female | Transplant |
| 40 | 52 | Male | Transplant |
| 4 | 53 | Male | Transplant |
| 5 | 53 | Male | Transplant |
| 58 | 54 | Male | Transplant |
| 35 | 55 | Male | Transplant |
| 1 | 59 | Female | Transplant |
| 9 | 60 | Female | Transplant |
| 6 | 60 | Male | Transplant |
| 17 | 60 | Male | Transplant |
| 38 | 62 | Female | Transplant |
| 56 | 64 | Female | Transplant |
| 12 | 65 | Male | Transplant |
| 2 | 67 | Male | Transplant |
| 33 | 69 | Female | Transplant |

(CRF = chronic renal failure not severe enough to require dialysis, Dialysis = haemodialysis for chronic renal failure, Transplant = recipient of renal transplant)

Peripheral blood leukocytes from the 20 patients in each group were stained with CD4/CD25/CD127/CD45RA and gated as indicated in FIG. 4A.

As shown in FIG. 29, the number of activated/memory Tregs was highest in the dialysis group and lowest in the transplantation group, and the difference was statistically significant. The reduction in number was probably a result of the immunosuppressive therapy used to prevent graft rejection. The naïve Treg numbers did not vary significantly within the 3 groups.

Example 19

Use of the Anti-Human CD4/CD25/CD127/CD45RO mAb Cocktail to Detect Treg in Macaques Peripheral blood was obtained from 32 macaques as part of a vaccination study carried out with the approval of the University of Melbourne and CSIRO Livestock Industries Animal Experimentation and Ethics Committees. There were 3 different groups: controls (11 subjects), a group treated with Gag protein (10 subjects) and a group treated with Gag, Env, Pol and RTNVVV (10 subjects).

The following mouse mAbs with primary specificity for human molecules were used in this study: anti-CD3, -CD4, -CD8, -CD45RO (PharMingen, San Diego, Calif.), -CD25 (BD Biosciences, San Jose, Calif.) -CD127 (Immunotech, Marseille, France).

Figure 30:
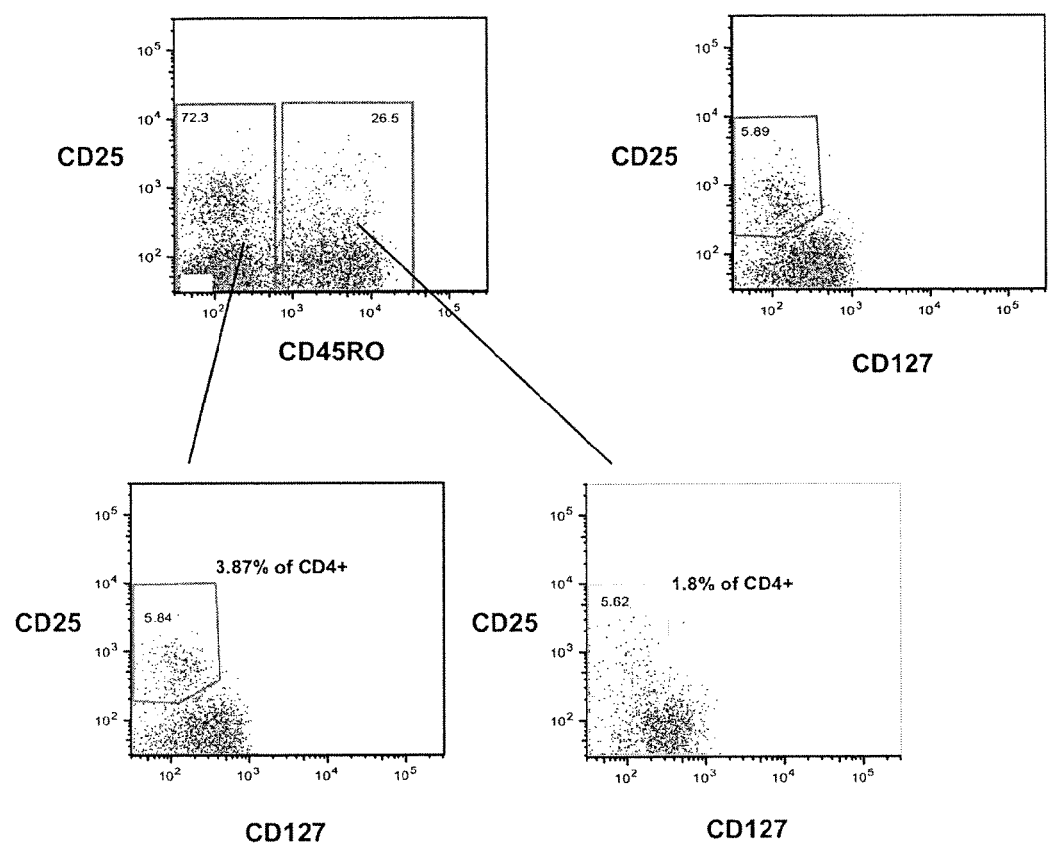
FIG. 30: Example of Treg gating in macaque, using anti-human antibodies that cross-react with macaque antigens. Upper panels: Dot plots of CD4⁺ T cells showing gating for expression of CD25 versus CD45RO and CD127. Percentages of cells within the gates are indicated. Lower panels: Gating for CD25⁺CD127$^{lo}$ cells within CD45RO⁻ and CD45RO⁺ cells, as indicated. The boxes represent the gates and the percentage is indicated within the gate. In addition, the percentage of Tregs is calculated as a percentage of total CD4⁺ T cells (indicated in bold text).
Figure 31:
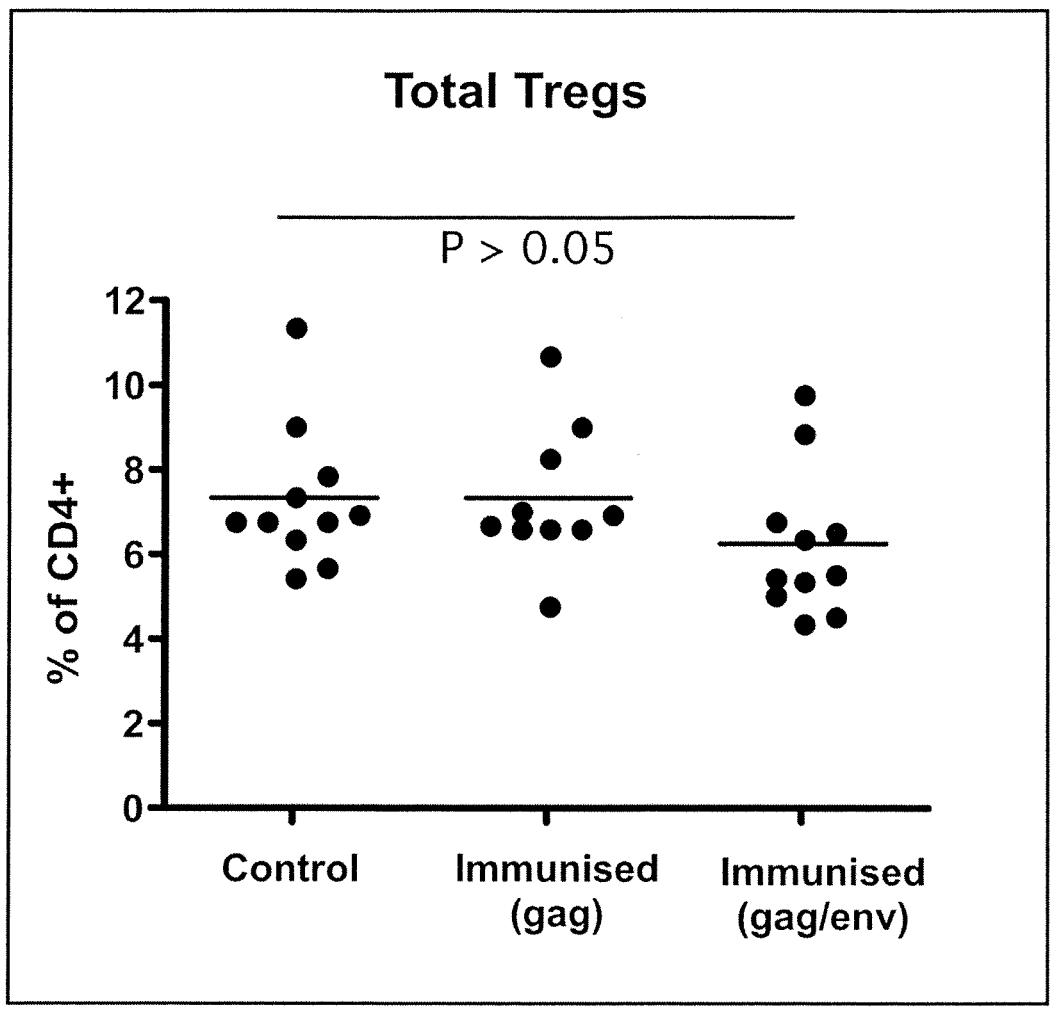
FIG. 31: Treg subsets in peripheral blood of macaques, gated as in FIG. 30. The range of total Tregs was between 4.39% and 11.42% and there were no significant changes following immunisation.

As shown in FIG. 30, expression of CD25, CD45R0 and CD127 in the peripheral blood leukocytes of macaques was similar to that in man, so that the same gating strategy could be employed to identify CD4$^+$CD25$^+$CD127$^{lo}$ cells. FIG. 31 shows that the percentage of Tregs in the peripheral blood of macaques is essentially the same as in humans, and that vaccination did not affect the numbers.

REFERENCES

1. Sakaguchi, S. 2004. Naturally arising CD4$^+$ regulatory T cells for immunologic self-tolerance and negative control of immune responses. *Annu. Rev. Immunol.* 22:531-562.
2. Kriegel, M. A., T. Lohmann, C. Gabler, N. Blank, J. R. Kalden, and H. M. Lorenz. 2004. Defective suppressor function of human CD4$^+$ CD25$^+$ regulatory T cells in autoimmune polyglandular syndrome type II. *J. Exp. Med.* 199:1285-1291.
3. Crispin, J. C., A. Martinez, and J. Alcocer-Varela. 2003. Quantification of regulatory T cells in patients with systemic lupus erythematosus. *J. Autoimmun.* 21:273-276.
4. Cao, D., R. van Vollenhoven, L. Klareskog, C. Trollmo, and V. Malmstrom. 2004. CD25$^{bright}$CD4$^+$ regulatory T cells are enriched in inflamed joints of patients with chronic rheumatic disease. *Arthritis Res. Ther.* 6:R335-346.
5. Ehrenstein, M. R., J. G. Evans, A. Singh, S. Moore, G. Warnes, D. A. Isenberg, and C. Mauri. 2004. Compromised function of regulatory T cells in rheumatoid arthritis and reversal by anti-TNFalpha therapy. *J. Exp. Med.* 200:277-285.
6. Sugiyama, H., R. Gyulai, E. Toichi, E. Garaczi, S. Shimada, S. R. Stevens, T. S. McCormick, and K. D. Cooper. 2005. Dysfunctional blood and target tissue CD4$^+$ CD25$^{high}$ regulatory T cells in psoriasis: mechanism underlying unrestrained pathogenic effector T cell proliferation. *J. Immunol.* 174:164-173.
7. Viglietta, V., C. Baecher-Allan, H. L. Weiner, and D. A. Hafler. 2004. Loss of functional suppression by CD4$^+$ CD25$^+$ regulatory T cells in patients with multiple sclerosis. *J. Exp. Med.* 199:971-979.
8. Furuno, K., T. Yuge, K. Kusuhara, H. Takada, H. Nishio, V. Khajoee, T. Ohno, and T. Hara. 2004. CD25$^+$CD4$^+$ regulatory T cells in patients with Kawasaki disease. *J. Pediatr.* 145:385-390.
9. Maul, J., C. Loddenkemper, P. Mundt, E. Berg, T. Giese, A. Stallmach, M. Zeitz, and R. Duchmann. 2005. Peripheral and intestinal regulatory CD4$^+$CD25$^{high}$ T cells in inflammatory bowel disease. *Gastroenterology* 128:1868-1878.
10. Karlsson, M. R., J. Rugtveit, and P. Brandtzaeg. 2004. Allergen-responsive CD4$^+$CD25$^+$ regulatory T cells in children who have outgrown cow's milk allergy. *J. Exp. Med.* 199:1679-1688.
11. Ling, E. M., T. Smith, X. D. Nguyen, C. Pridgeon, M. Dallman, J. Arbery, V. A. Carr, and D. S. Robinson. 2004. Relation of CD4$^+$CD25$^+$ regulatory T-cell suppression of allergen-driven T-cell activation to atopic status and expression of allergic disease. *Lancet* 363:608-615.
12. Bennett, C. L., J. Christie, F. Ramsdell, M. E. Brunkow, P. J. Ferguson, L. Whitesell, T. E. Kelly, F. T. Saulsbury, P. F. Chance, and H. D. Ochs. 2001. The immune dysregulation, polyendocrinopathy, enteropathy, X-linked syndrome (IPEX) is caused by mutations of FOXP3. *Nat. Genet.* 27:20-21.
13. Ormandy, L. A., T. Hillemann, H. Wedemeyer, M. P. Manns, T. F. Greten, and F. Korangy. 2005. Increased populations of regulatory T cells in peripheral blood of patients with hepatocellular carcinoma. *Cancer Res.* 65:2457-2464.
14. Schaefer, C., G. G. Kim, A. Albers, K. Hoermann, E. N. Myers, and T. L. Whiteside. 2005. Characteristics of CD4$^+$ CD25$^+$ regulatory T cells in the peripheral circulation of patients with head and neck cancer. *Br J Cancer* 92:913-20.
15. Baecher-Allan, C., J. A. Brown, G. J. Freeman, and D. A. Hafler. 2001. CD4$^+$CD25$^{high}$ regulatory cells in human peripheral blood. *J. Immunol.* 167:1245-1253.
16. Kukreja, A., G. Cost, J. Marker, C. Zhang, Z. Sun, K. Lin-Su, S. Ten, M. Sanz, M. Exley, B. Wilson, S. Porcelli, and N. Maclaren. 2002. Multiple immuno-regulatory defects in type-1 diabetes. *J. Clin. Invest.* 109:131-140.
17. Cao, D., V. Malmstrom, C. Baecher-Allan, D. Hafler, L. Klareskog, and C. Trollmo. 2003. Isolation and functional characterization of regulatory CD25$^{high}$CD4$^+$ T cells from the target organ of patients with rheumatoid arthritis. *Eur. J. Immunol.* 33:215-223.
18. Huang, Y. M., R. Pirskanen, R. Giscombe, H. Link, and A. K. Lefvert. 2004. Circulating CD4$^+$CD25$^+$ and CD4$^+$ CD25$^-$ T cells in myasthenia gravis and in relation to thymectomy. *Scand. J. Immunol.* 59:408-414.
19. Putheti, P., A. Pettersson, M. Soderstrom, H. Link, and Y. M. Huang. 2004. Circulating CD4$^+$CD25$^+$ T regulatory cells are not altered in multiple sclerosis and unaffected by disease-modulating drugs. *J. Clin. Immunol.* 24:155-61.
20. van Amelsfort, J. M., K. M. Jacobs, J. W. Bijlsma, F. P. Lafeber, and L. S. Taams. 2004. CD4$^+$CD25$^+$ regulatory T cells in rheumatoid arthritis: differences in the presence, phenotype, and function between peripheral blood and synovial fluid. *Arthritis Rheum.* 50:2775-2785.
21. Seddiki, N., B. Santner-Nanan, S. G. Tangye, S. I. Alexander, M. Solomon, S. Lee, R. Nanan, and B. Fazekas de St Groth. 2006. Persistence of naïve CD45RA$^+$ regulatory T cells in adult life. *Blood* 107:2830-2838.
22. Seddiki, N., W. Selby, M. Solomon, S. Lee, P. McKenzie, and B. Fazekas de St Groth. 2006. Young patients with inflammatory bowel disease display primary defects in regulatory T cells. submitted for publication
23. Ruprecht, C. R., M. Gattorno, F. Ferlito, A. Gregorio, A. Martini, AntonioLanzavecchia, and F. Sallusto. 2005. Coexpression of CD25 and CD27 identifies FoxP3$^+$ regulatory T cells in inflamed synovia. *J. Exp. Med.* 201:1793-1803.
24. Morgan, M. E., J. H. van Bilsen, A. M. Bakker, B. Heemskerk, M. W. Schilham, F. C. Hartgers, B. G. Elferink, L. van der Zanden, R. R. de Vries, T. W. Huizinga, T. H. Ottenhoff, and R. E. Toes. 2005. Expression of FOXP3 mRNA is not confined to CD4$^+$CD25$^+$ T regulatory cells in humans. *Hum. Immunol.* 66:13-20.
25. Cozzo, C., J. Larkin, 3rd, and A. J. Caton. 2003. Self-peptides drive the peripheral expansion of CD4$^+$CD25$^+$ regulatory T cells. *J. Immunol.* 171:5678-5682.
26. Gavin, M. A., S. R. Clarke, E. Negrou, A. Gallegos, and A. Rudensky. 2002. Homeostasis and anergy of CD4$^+$CD25$^+$ suppressor T cells in vivo. *Nat. Immunol.* 3:33-41.

27. Godfrey, W. R., D. J. Spoden, Y. G. Ge, S. R. Baker, B. Liu, B. L. Levine, C. H. June, B. R. Blazer, and S. B. Porter. 2005. Cord blood CD4+CD25+-derived T regulatory cell lines express FoxP3 protein and manifest potent suppressor function. *Blood* 105:750-758.
28. Baecher-Allan, C., E. Wolf, and D. A. Hafler. 2006. MHC class II expression identifies functionally distinct human regulatory T cells. *J. Immunol.* 176:4622-4631.
29. Vitali, C., S. Bombardieri, R. Jonsson, H. M. Moutsopoulos, E. L. Alexander, S. E. Carsons, T. E. Daniels, P. C. Fox, R. I. Fox, S. S. Kassan, S. R. Pillemer, N. Talal, and M. H. Weisman. 2002. Classification criteria for Sjogren's syndrome: a revised version of the European criteria proposed by the American-European Consensus Group. *Ann. Rheum. Dis.* 61:554-8.

The invention claimed is:

1. A kit for identifying in a primate subject a regulatory T cell or a population of regulatory T cells, the kit comprising:
   at least one antibody for determining a level of cellular expression of CD127, at least one antibody for determining a level of cellular expression of CD4 and at least one antibody for determining a level of cellular expression of CD25 in a primate subject,
   wherein a determined expression level of $CD127^{low}CD4^+CD25^+$ is indicative of a regulatory T cell or a population of regulatory T cells.

2. The kit according to claim 1, further comprising at least one antibody for determining in a primate subject a level of cellular expression of at least one additional cellular polypeptide.

3. The kit according to claim 2, wherein the at least one additional cellular polypeptide is CD45RA, CD45RO, Foxp3, CTLA-4 or CD95.

4. A kit for quantifying a population of regulatory T cells in a subject in need thereof, the kit comprising:
   (1) at least one antibody for determining a level of cellular expression of CD127, at least one antibody for determining a level of cellular expression of CD4 and at least one antibody for determining a level of cellular expression of CD25 in a primate subject,
   wherein a determined expression level of $CD127^{low}CD4^+CD25^+$ is indicative of a regulatory T cell or a population of regulatory T cells.

5. A kit for use in the diagnosis of:
   (a) the over-production or under-production of regulatory T cells in a primate subject;
   (b) an autoimmune, immunoinflammatory or allergic disease, or predisposition thereto in a primate subject; and/or
   (c) a disease that is associated with a change in the quantity of regulatory T cells in a primate subject, wherein said kit comprises:

at least one antibody for determining a level of cellular expression of CD127, at least one antibody for determining a level of cellular expression of CD4 and at least one antibody for determining a level of cellular expression of CD25 in a primate subject,
   wherein a determined expression level of $CD127^{low}CD4^+CD25^+$ expression is indicative of a regulatory T cell or a population of regulatory T cells.

6. The kit according to claim 5, further comprising at least one antibody for determining a level of cellular expression of at least one additional cellular polypeptide.

7. A kit for use in monitoring the quantity of regulatory T cells in a primate subject during the course of a disease state, infection or therapy, wherein said kit comprises:
   at least one antibody for determining a level of cellular expression of CD127, at least one antibody for determining a level of cellular expression of CD4 and at least one antibody for determining a level of cellular expression of CD25 in a primate subject,
   wherein a determined expression level of $CD127^{low}CD4^+CD25^+$ is indicative of a regulatory T cell or a population of regulatory T cells.

8. The kit according to claim 7, further comprising at least one antibody for determining a level of cellular expression of at least one additional cellular polypeptide.

9. A kit for use in predicting a response to therapy for a disease state or infection in a primate subject based on the quantity of regulatory T cells in the subject, wherein said kit comprises:
   at least one antibody for determining a level of cellular expression of CD127, at least one antibody for determining a level of cellular expression of CD4 and at least one antibody for determining a level of cellular expression of CD25 in a primate subject,
   wherein a determined expression level of $CD127^{low}CD4^+CD25^+$ is indicative of a regulatory T cell or a population of regulatory T cells.

* * * * *